United States Patent
Trabanco-Suárez et al.

(10) Patent No.: US 9,840,507 B2
(45) Date of Patent: Dec. 12, 2017

(54) 5,6-DIHYDRO-IMIDAZO[1,2-A]PYRAZIN-8-YLAMINE DERIVATIVES USEFUL AS INHIBITORS OF BETA-SECRETASE (BACE)

(75) Inventors: Andrés Avelino Trabanco-Suárez, Toledo (ES); Francisca Delgado-Jiménez, Toledo (ES); Juan Antonio Vega Ramiro, Toledo (ES); Gary John Tresadern, Toledo (ES); Henricus Jacobus Maria Gijsen, Beerse (BE); Daniel Oehlrich, Beerse (BE)

(73) Assignee: Janssen Pharmaceutica, NV, Beerse (BE)

( * ) Notice: Subject to any disclaimer, the term of this patent is extended or adjusted under 35 U.S.C. 154(b) by 0 days.

(21) Appl. No.: 13/995,523

(22) PCT Filed: Dec. 21, 2011

(86) PCT No.: PCT/EP2011/073522
§ 371 (c)(1),
(2), (4) Date: Jun. 19, 2013

(87) PCT Pub. No.: WO2012/085038
PCT Pub. Date: Jun. 28, 2012

(65) Prior Publication Data
US 2013/0274266 A1 Oct. 17, 2013

(30) Foreign Application Priority Data
Dec. 22, 2010 (EP) .................................... 10196568

(51) Int. Cl.
*A61K 31/4985* (2006.01)
*C07D 487/04* (2006.01)

(52) U.S. Cl.
CPC ................. *C07D 487/04* (2013.01)

(58) Field of Classification Search
CPC ........................ A61K 31/4985; C07D 487/04
USPC .......................................... 514/249; 544/350
See application file for complete search history.

(56) References Cited

U.S. PATENT DOCUMENTS

| | | | |
|---|---|---|---|
| 4,188,389 | A | 2/1980 | Jirkovsky |
| 5,292,732 | A | 3/1994 | Rover |
| 8,207,164 | B2 | 6/2012 | Holzer |
| 2005/0282825 | A1 | 12/2005 | Malamas |
| 2007/0005404 | A1 | 1/2007 | Raz |
| 2007/0225372 | A1 | 9/2007 | Bueno Melendo |
| 2008/0051420 | A1 | 2/2008 | Berg |
| 2009/0082560 | A1 | 3/2009 | Kobayashi |
| 2011/0009395 | A1 | 1/2011 | Audia et al. |
| 2012/0238557 | A1 | 9/2012 | Masui et al. |
| 2012/0277244 | A1 | 11/2012 | Tintelnot-Blomley |
| 2014/0256715 | A1 | 9/2014 | Hurth et al. |
| 2016/0152581 | A1 | 6/2016 | Trabanco-Suarez et al. |

FOREIGN PATENT DOCUMENTS

| | | |
|---|---|---|
| CA | 2825620 | 9/2012 |
| EP | 2147914 | 1/2010 |
| EP | 2 518 059 | 10/2012 |
| JP | 2013-513563 | 4/2013 |
| JP | 2012-147763 | 7/2014 |
| JP | 2014-505688 | 3/2015 |
| WO | WO 1998/057641 | 12/1998 |
| WO | WO2003089434 | 10/2003 |
| WO | WO2004026877 | 4/2004 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
Vippagunta, et al. Advanced Drug Delivery Reviews, 48, 2001, 18.*
Esterhazy et al_Cell Metabolism, "Bace2 is a βCell-Enriched Protease that Regulates Pancreatic βCell Function and Mass",_2011_14_365-377.
Fleck et al. 2012, Curr. Alzheimer Res., "BacelDependent Neuregulin Processing: review" 9, 178-183.
Hackam, et al. Jama, "Translation of Research Evidence From animals to Humans", 296(14), 2006, 1731-1732.
Haniu et al., 2000, J. Biol. Chem., "Protein Structure and folding: Characterization of Alzheimer's β-secretase protein BACE: a Pepsin Family member with Unusual Properties", 275, 21099-21106.

(Continued)

*Primary Examiner* — Douglas M Willis
(74) *Attorney, Agent, or Firm* — Yuriy P. Stercho

(57) ABSTRACT

The present invention relates to novel 5,6-dihydro-imidazo[1,2-a]pyrazin-8-ylamine inhibitors of beta-secretase, having the structure shown in Formula (I)

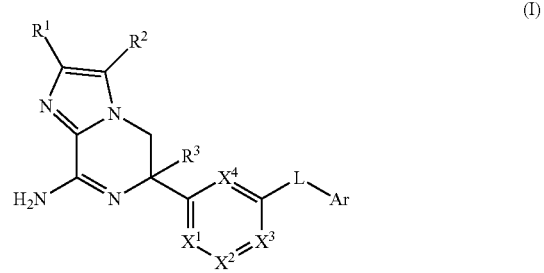

wherein $R^1$, $R^2$, $R^3$, $R^4$, $X^1$, $X^2$, $X^3$, $X^4$, L and Ar are defined in the specification. The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, cerebrovascular amyloid angiopathy, multi-infarct dementia, Down's syndrome, dementia associated with stroke, dementia associated with Parkinson's disease or dementia associated with beta-amyloid.

7 Claims, No Drawings

(56) References Cited

FOREIGN PATENT DOCUMENTS

| | | |
|---|---|---|
| WO | WO2004058176 | 7/2004 |
| WO | WO2005037832 | 4/2005 |
| WO | WO2006034093 A2 | 3/2006 |
| WO | WO2006076284 | 7/2006 |
| WO | WO2006/138265 | 12/2006 |
| WO | WO2007058583 A2 | 5/2007 |
| WO | WO2007114771 A1 | 10/2007 |
| WO | WO2007138265 A2 | 12/2007 |
| WO | WO2009022961 A1 | 2/2009 |
| WO | WO2009058300 A1 | 5/2009 |
| WO | WO2009097278 A1 | 8/2009 |
| WO | WO2009102468 A1 | 8/2009 |
| WO | WO2009134617 A1 | 11/2009 |
| WO | WO2007/005404 | 1/2010 |
| WO | WO2011002409 A1 | 1/2011 |
| WO | WO2011009943 A1 | 1/2011 |
| WO | WO2011020806 A1 | 2/2011 |
| WO | WO 2011/069934 | 6/2011 |
| WO | WO2011071135 A1 | 6/2011 |
| WO | WO2011080176 A1 | 7/2011 |
| WO | WO 2011/154374 | 12/2011 |
| WO | WO2011154431 A1 | 12/2011 |
| WO | WO 2012/000933 | 1/2012 |
| WO | WO 2012/038438 | 3/2012 |
| WO | WO2012057247 A1 | 5/2012 |
| WO | WO 2012/085038 * | 6/2012 |
| WO | WO2012085038 A1 | 6/2012 |
| WO | WO 2012/095463 | 7/2012 |
| WO | WO 2012/098064 | 7/2012 |
| WO | WO2012117027 A1 | 9/2012 |
| WO | WO2012120023 A1 | 9/2012 |
| WO | WO 2012/147763 | 11/2012 |
| WO | WO 2013/083556 | 6/2013 |
| WO | WO 2013/083557 | 6/2013 |
| WO | WO 2014/099794 | 6/2014 |
| WO | WO 2014/198851 | 12/2014 |
| WO | WO 2014/198853 | 12/2014 |
| WO | WO 2014/198854 | 12/2014 |
| WO | WO 2016/096979 | 6/2016 |

OTHER PUBLICATIONS

Hemming et al. 2009, PLS ONE, "Identification of β-Secretase (BACE1) Substrates using Quantitative Proteomics", 4, e8477.
Hong et al, 2000, Science, "Structure of the Protease domain of memapsin 2(β-Secretase) Complexed with Inhibitor" 290, 150-153.
Jonsson et al. 2012, Nature, "A mutation in APP protects against Alzheimer's disease and age-related cognitive decline", 488, 96-99.
Kim et al. 2011, J. Biol. Chem. "Molecular Bases of Disease: Reduced Sodium Channel Nav1.1 Levels in BACE1-null Mice", 286, 8106-8116.
Koike H et al.,J Biochem., "Thimet Oligopeptidase Cleaves the Full-Length Alzheimer Amyloid Precursor Protein at a β-Secretase Cleavage Site in COS Cells" 1999, 126, 235-42.
Kondoh et al. Breast Cancer Res.Treat., "A novel aspartic protease gene, ALP56, is up-regulated in human breast cancer independently from the cathepsin D gene", 2003, vol. 78, pp. 37-44.
Kuhn et al. 2012, EMBO J. "Secretome protein enrichment identifies physiological BACE1protease substrates in neurons" 31, 3157-3168.
Kuhn et al. J. Biol. Chem."Protein Synthesis, Post-translation Modification, and Degradation: Regulated Intramembrane Proteolysis of the Interleukin-1 receptor II by α-,β-, and γ-Secretase", 2007, vol. 282, No. 16, pp. 11982-11995.
Luo et al., 2001, Nat. Neurosci, "Mice deficient in Bace!, the Alzheimer's β-secretase, have normal phenotype and abolished β-amyloid generation", 4, 231-232.
Naus et al. 2004, J. Biol. Chem.,"Enzyme Catalysis and Regulation: Extodomain Shedding of the Neural Recognition Molecule CHL1 by the Metalloprotease-disintegrin ADAM8 Promotes Neurite Outgrowth and Suppresses Neuronal Cell Death", 279, 16083-16090.
Ostermann et al, 2006, Journal of molecular biology, "Crystal Structure of Human BACE2 in Complex with a Hydroxyethylamine transition-state Inhibitor", 355, (2), 249-61.
Patani et al, Chem.Rev., "Bioisosterism: a Rational Approach in Drug Design", 1996, 96, 3147-3176.
Roberds et al., 2001, Hum. Mol. Genet, "BACE knockout mice are healthy despite lacking the primary β-secretase activity in the brain: implications for Alzheimer's disease therapeutics",10, 1317-1324.
Rochin et al. Pnas, "BACE2 processes PMEL to form the melanosome amyloid matrix in pigment cells", Jun. 25, 2013, vol. 110, No. 26, pp. 10658-10663.
Silvestri Medicinal Research Reviews, "Boom in the development of Non-Peptidic β-secretase (BACE1) Inhibitors for the Treatment of Alzheimer's Disease", 295-238 2009.
Stutzer et al. 2013, J. Biol. Chem., "Systematic Proteomic Analysis Identifies β-Site Amyloid Precursor Protein Cleaving Enzyme 2 and 1 (BACE2 and BACE1) Substrates in Pancreatic β-Cells" 288, 10536-10547.
Cheret et al. 2013 EMBO Journal, "Bacel and Neuregulin-1 cooperate to control formation and maintenance of muscle spindles", (2013), 32(14), 2015-2028.
Jordan, V. C. Nature Reviews: Drug Discovery,"Tamoxifen: a Most Unlikely Pioneering Medicine", 2, 2003, 205.
Vassar et al., J. Neurochem., "Function, therapeutic potential and cell biology of BACE proteases: current status and future prospects", (2014) 10.1111/jnc.12715.
Vippagunta, et al. Advanced Drug Delivery Reviews, "Crystalline Solids", 48, 2001, 18.
Wang et al. Trends in Pharmacological Sciences, Apr, "β-Secretase: its biology as a therapeutic target in diseases", 2013, vol. 34, No. 4, pp. 215-225.
Willem et al. 2009, Semin. Cell Dev. Biol., Function, regulation and therapeutic properties of β-secretase (BACE1) 20, 175-182.
Yan and Vassar Lancet Neurol. "Targeting the βsecretase BACE1 for Alzheimer's disease therapy", 2014, vol. 13, pp. 319-329.
Yan et al. J Alzheimers Dis. "Can BACE! Inhibition Mitigate Early Axonal Pathology in Neurological Diseases?", 2014, 30 vol. 38, No. 4, pp. 705-718.
Sheridan, et al., "The Most Common Chemical Replacements in Drug-Like Compounds", J. Chem. Inf. Comput. Sci., 2002 vol. 42, pp. 103-108.
J.G. Cannon Chapter Nineteen in Burger's Medicinal Chemistry and Drug discovery, Fifth Edition, vol. I; Principles and Practice, Wiley-Interscience 1995, pp. 783-802, 784.
Zhou et al. 2012, J. Biol. Chem. "The Neural Cell Adhesion Molecules L1 and CHL1 are Cleaved by BACE1 Protease in Vivo", 287, 25927-25940.
Hilpert, et al., "β-Secretase (BACE1) Inhibitors with High in vivo efficacy Suitable for Clinical Evaluation in Alzheimer's Disease", Journal of Medicinal Chemistry, vol. 56, No. 10, pp. 3980-3995, 2013.
Woltering, et al., "BACE Inhibitors: A head group scan on a series of amides:", Biorganic & Medicinal Chemistry Letters, vol. 23, pp. 4239-4243, 2013.
Ginman, et al., "Core refinement toward Permeable β-Secretase (BACE-1) Inhibitors with Low HERG Activity", Journal of Medicinal Chemistry, vol. 56, pp. 4181-4205, 2013.
Purser, et al., "Flourine in Medicinal Chemistry", Chemical Society Reviews, 2008, vol. 37, pp. 320-330.
Park, et al., "Metabolism of Fluorine-Containing Drugs", Annual Ref. Pharmacol. Toxicol. 2001, vol. 41, pp. 443-470.
Park, et al., Effects of Flourine Substitution on Drug Metabolism: Pharmacological and Toxicological Implicants*, Drug metabolism reviews, vol. 26(3), 1994, pp. 605-643.
Wang, et al., Fluroine in Pharmaceutical Industry: Flourine-Containing Drugs Introduced to the Market in the Last Decade (2001-2011).
Zhang, et al, "Application of Amybidbeta Protein in the Diagnosis of Alzheimer's Disease", vol. 29, No. 1, 2008.
Martic-Kehl et al., Eur J. Nucl Med Mol Imaging (2012) 39:1492-1496.
Mateu et al., Chem. Eur. J. 2015, 21, 11719-11726.

(56) References Cited

OTHER PUBLICATIONS

Oehlrich et al. The evolution of amidine-based brain penetrant BACE1 inhibitors_Bioorganic & Medicinal Chemistry Letters, 2014, vol. 24, pp. 2033-2045.

NIH National Institute on Aging, Aug. 2016, https://www.nia.nih.gov/alzheimers/publication/alheimers-disease-fact-sheet, NIH Publication No. 16-AG-6423.

* cited by examiner

5,6-DIHYDRO-IMIDAZO[1,2-A]PYRAZIN-8-YLAMINE DERIVATIVES USEFUL AS INHIBITORS OF BETA-SECRETASE (BACE)

FIELD OF THE INVENTION

The present invention relates to novel 5,6-dihydro-imidazo[1,2-a]pyrazin-8-ylamine derivatives as inhibitors of beta-secretase, also known as beta-site amyloid cleaving enzyme, BACE, BACE1, Asp2, or memapsin2. The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, cerebral amyloid angiopathy, multi-infarct dementia, Down's syndrome, dementia associated with stroke, dementia associated with Parkinson's disease or dementia associated with beta-amyloid.

BACKGROUND OF THE INVENTION

Alzheimer's Disease (AD) is a neurodegenerative disease associated with aging. AD patients suffer from cognition deficits and memory loss as well as behavioral problems such as anxiety. Over 90% of those afflicted with AD have a sporadic form of the disorder while less than 10% of the cases are familial or hereditary. In the United States, about 1 in 10 people at age 65 have AD while at age 85, 1 out of every two individuals are affected with AD. The average life expectancy from the initial diagnosis is 7-10 years, and AD patients require extensive care either in an assisted living facility which is very costly or by family members. With the increasing number of elderly in the population, AD is a growing medical concern. Currently available therapies for AD merely treat the symptoms of the disease and include acetylcholinesterase inhibitors to improve cognitive properties as well as anxiolytics and antipsychotics to control the behavioral problems associated with this ailment.

The hallmark pathological features in the brain of AD patients are neurofibillary tangles which are generated by hyperphosphorylation of tau protein and amyloid plaques which form by aggregation of beta-amyloid 1-42 (Abeta 1-42) peptide. Abeta 1-42 forms oligomers and then fibrils, and ultimately amyloid plaques. The oligomers and fibrils are believed to be especially neurotoxic and may cause most of the neurological damage associated with AD. Agents that prevent the formation of Abeta 1-42 have the potential to be disease-modifying agents for the treatment of AD. Abeta 1-42 is generated from the amyloid precursor protein (APP), comprised of 770 amino acids. The N-terminus of Abeta 1-42 is cleaved by beta-secretase (BACE), and then gamma-secretase cleaves the C-terminal end. In addition to Abeta 1-42, gamma-secretase also liberates Abeta 1-40 which is the predominant cleavage product as well as Abeta 1-38 and Abeta 1-43. These Abeta forms can also aggregate to form oligomers and fibrils. Thus, inhibitors of BACE would be expected to prevent the formation of Abeta 1-42 as well as Abeta 1-40, Abeta 1-38 and Abeta 1-43 and would be potential therapeutic agents in the treatment of AD.

SUMMARY OF THE INVENTION

The present invention is directed to a compound of Formula (I)

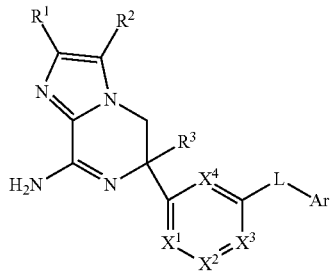

or a tautomer or a stereoisomeric form thereof, wherein
$R^1$ and $R^2$ are independently selected from the group consisting of hydrogen, halo, cyano, $C_{1-3}$alkyl, mono- and polyhalo-$C_{1-3}$alkyl, and $C_{3-6}$cycloalkyl;
$R^3$ is selected from the group consisting of hydrogen, $C_{1-3}$alkyl, $C_{3-6}$cycloalkyl, mono- and polyhalo-$C_{1-3}$alkyl, homoaryl and heteroaryl;
$X^1, X^2, X^3, X^4$ are independently $C(R^4)$ or N, provided that no more than two thereof represent N; each $R^4$ is selected from the group consisting of hydrogen, halo, $C_{1-3}$alkyl, mono- and polyhalo-$C_{1-3}$alkyl, cyano, $C_{1-3}$alkyloxy, mono- and polyhalo-$C_{1-3}$alkyloxy;
L is a bond or —N($R^5$)CO—, wherein $R^5$ is hydrogen or $C_{1-3}$alkyl;
Ar is homoaryl or heteroaryl;
wherein homoaryl is phenyl or phenyl substituted with one, two or three substituents selected from the group consisting of halo, cyano, $C_{1-3}$alkyl, $C_{1-3}$alkyloxy, mono- and polyhalo-$C_{1-3}$alkyl;
heteroaryl is selected from the group consisting of pyridyl, pyrimidyl, pyrazyl, pyridazyl, furanyl, thienyl, pyrrolyl, pyrazolyl, imidazolyl, triazolyl, thiazolyl, isothiazolyl, thiadiazolyl, oxazolyl, and oxadiazolyl, each optionally substituted with one, two or three substituents selected from the group consisting of halo, cyano, $C_{1-3}$alkyl, $C_{1-3}$alkyloxy, mono- and polyhalo-$C_{1-3}$alkyl; or
an addition salt or a solvate thereof.

Illustrative of the invention is a pharmaceutical composition comprising a pharmaceutically acceptable carrier and any of the compounds described herein. An illustration of the invention is a pharmaceutical composition made by mixing any of the compounds described herein and a pharmaceutically acceptable carrier. Illustrating the invention is a process for making a pharmaceutical composition comprising mixing any of the compounds described herein and a pharmaceutically acceptable carrier.

Exemplifying the invention are methods of treating a disorder mediated by the beta-secretase enzyme, comprising administering to a subject in need thereof a therapeutically effective amount of any of the compounds or pharmaceutical compositions described herein.

Further exemplifying the invention are methods of inhibiting the beta-secretase enzyme, comprising administering to a subject in need thereof a therapeutically effective amount of any of the compounds or pharmaceutical compositions described herein.

An example of the invention is a method of treating a disorder selected from the group consisting of Alzheimer's disease, mild cognitive impairment, senility, dementia, dementia with Lewy bodies, cerebral amyloid angiopathy, multi-infarct dementia, Down's syndrome, dementia associated with stroke, dementia associated with Parkinson's disease and dementia associated with beta-amyloid, preferably Alzheimer's disease, comprising administering to a subject in need thereof, a therapeutically effective amount of any of the compounds or pharmaceutical compositions described herein.

Another example of the invention is any of the compounds described herein for use in treating: (a) Alzheimer's Disease, (b) mild cognitive impairment, (c) senility, (d) dementia, (e) dementia with Lewy bodies, (f) Down's syndrome, (g) dementia associated with stroke, (h) dementia associated with Parkinson's disease and (i) dementia associated with beta-amyloid, in a subject in need thereof.

DETAILED DESCRIPTION OF THE INVENTION

The present invention is directed to compounds of formula (I) as defined hereinbefore and pharmaceutically acceptable salts and solvates thereof. The compounds of formula (I) are inhibitors of the beta-secretase enzyme (also known as beta-site cleaving enzyme, BACE, BACE1, Asp2 or memapsin 2), and are useful in the treatment of Alzheimer's disease, mild cognitive impairment, senility, dementia, dementia associated with stroke, dementia with Lewy bodies, Down's syndrome, dementia associated with Parkinson's disease and dementia associated with beta-amyloid, preferably Alzheimer's disease, mild cognitive impairment or dementia, more preferably Alzheimer's disease.

In an embodiment of the present invention, $R^1$ and $R^2$ are independently selected from the group consisting of hydrogen, halo, cyano, $C_{1-3}$alkyl, mono- and polyhalo-$C_{1-3}$alkyl, and $C_{3-6}$cycloalkyl;
$R^3$ is selected from the group consisting of hydrogen, $C_{1-3}$alkyl, $C_{3-6}$cycloalkyl, mono- and polyhalo-$C_{1-3}$alkyl, homoaryl and heteroaryl;
$X^1$, $X^2$, $X^3$, $X^4$ are independently $C(R^4)$ or N, provided that no more than two thereof represent N; each $R^4$ is selected from the group consisting of hydrogen, halo, $C_{1-3}$alkyl, mono- and polyhalo-$C_{1-3}$alkyl, cyano, $C_{1-3}$alkyloxy, mono- and polyhalo-$C_{1-3}$alkyloxy;
L is a bond or —N($R^5$)CO—, wherein $R^5$ is hydrogen or $C_{1-3}$alkyl;
Ar is homoaryl or heteroaryl;
wherein homoaryl is phenyl or phenyl substituted with one, two or three substituents selected from the group consisting of halo, cyano, $C_{1-3}$alkyl, $C_{1-3}$alkyloxy, mono- and polyhalo-$C_{1-3}$alkyl;
heteroaryl is selected from the group consisting of pyridyl, pyrimidyl, pyrazyl, pyridazyl, furanyl, thienyl, pyrrolyl, pyrazolyl, imidazolyl, triazolyl, thiazolyl, thiadiazolyl, oxazolyl, and oxadiazolyl, each optionally substituted with one, two or three substituents selected from the group consisting of halo, cyano, $C_{1-3}$alkyl, $C_{1-3}$alkyloxy, mono- and polyhalo-$C_{1-3}$alkyl; or
an addition salt or a solvate thereof.

In an embodiment of the present invention, $R^1$ and $R^2$ are independently selected from hydrogen and $C_{1-3}$alkyl;
$R^3$ is $C_{1-3}$alkyl;
$X^1$, $X^2$, $X^3$, $X^4$ are independently $C(R^4)$ wherein each $R^4$ is selected from hydrogen and halo;
L is a bond or —N($R^5$)CO—, wherein $R^5$ is hydrogen;
Ar is homoaryl or heteroaryl;
wherein homoaryl is phenyl or phenyl substituted with one or two substituents selected from the group consisting of halo, cyano, $C_{1-3}$alkyl, and $C_{1-3}$alkyloxy; heteroaryl is selected from the group consisting of pyridyl, pyrimidyl, pyridazyl, and pyrazyl, each optionally substituted with one or two substituents selected from the group consisting of halo, cyano, $C_{1-3}$alkyl, and $C_{1-3}$alkyloxy; or
an addition salt or a solvate thereof.

In another embodiment of the present invention, $R^1$ and $R^2$ are hydrogen; $R^3$ is methyl;
$X^1$, $X^2$, $X^3$, $X^4$ are CH or CF;
L is a bond or —N($R^5$)CO—, wherein $R^5$ is hydrogen;
Ar is homoaryl or heteroaryl;
wherein homoaryl is phenyl substituted with chloro; heteroaryl is selected from the group consisting of pyridyl, pyrazyl, pyridazyl, and pyrimidyl, each optionally substituted with one or two substituents selected from the group consisting of chloro, fluoro, cyano, methyl, and methoxy; or
an addition salt or a solvate thereof.

In another embodiment $R^1$ and $R^2$ are independently selected from the group consisting of hydrogen, mono-, di- and trifluoromethyl, chloro, bromo and cyano;
$R^3$ is $C_{1-3}$alkyl or mono-, di- and trifluoromethyl;
$X^1$ and $X^3$ are independently CH or CF; $X^2$ and $X^4$ are CH;
L is —N($R^5$)CO—, wherein $R^5$ is hydrogen;
Ar is homoaryl or heteroaryl;
wherein homoaryl is phenyl substituted with one or two substituents selected from the group consisting of halo, cyano, $C_{1-3}$alkyl, and $C_{1-3}$alkyloxy;
heteroaryl is selected from the group consisting of pyridyl, pyrimidyl, pyridazyl, pyrazolyl, oxazolyl and isothiazolyl, each optionally substituted with one or two substituents selected from the group consisting of halo, cyano, $C_{1-3}$alkyl, $C_{1-3}$alkyloxy, mono-, di- and trifluoromethyl; or
an addition salt or a solvate thereof.

In another embodiment $R^1$ is hydrogen, mono-, di-, or trifluoromethyl, chloro, bromo or cyano;
$R^2$ is hydrogen, chloro, cyano, mono-, di- or trifluoromethyl;
$R^3$ is methyl, mono- di-, or trifluoromethyl;
$X^1$ is CF; $X^2$, $X^3$, $X^4$ are CH;
L is —N($R^5$)CO—, wherein $R^5$ is hydrogen;
Ar is heteroaryl;
wherein heteroaryl is selected from the group consisting of pyridyl, pyrazyl and pyrazolyl, each substituted with one or two substituents selected from the group consisting of chloro, fluoro, cyano, methyl, methoxy, ethoxy, mono-, di-, and trifluoromethyl; or
an addition salt or a solvate thereof.

In another embodiment $R^1$ and $R^2$ are independently selected from the group consisting of hydrogen, mono-, di- and trifluoromethyl, chloro, bromo and cyano;
$R^3$ is $C_{1-3}$alkyl or mono-, di- and trifluoromethyl;
$X^1$ and $X^3$ are independently CH or CF; $X^2$ and $X^4$ are CH;
L is —N($R^5$)CO—, wherein $R^5$ is hydrogen;
Ar is heteroaryl;
wherein heteroaryl is selected from the group consisting of 5-chloro-2-pyridyl, 5-fluoro-2-pyridyl, 5-cyano-2-pyridyl, 3,5-dichloro-2-pyridyl, 3-fluoro-5-chloro-2-pyridyl, 3-fluoro-5-cyano-2-pyridyl, 3-chloro-5-cyano-2-pyridyl, 5-methoxy-2-pyrazyl, 5-ethoxy-2-pyrazyl, 1-difluoromethyl-3-pyrazolyl, 2-methyl-4-oxazolyl, 2,5-dimethyl-4-oxazolyl, 2-methyl-5-trifluoromethyl-4-oxazolyl, 3-isothiazolyl, or
an addition salt or a solvate thereof.

In another embodiment, the carbon atom substituted with $R^3$ has the R-configuration.

Definitions

"Halo" shall denote fluoro, chloro and bromo; "$C_{1-3}$alkyl" shall denote a straight or branched saturated alkyl group having 1, 2 or 3 carbon atoms, e.g. methyl, ethyl, 1-propyl and 2-propyl; "$C_{1-3}$alkyloxy" shall denote an ether radical wherein $C_{1-3}$alkyl is as defined before; "mono- and polyhalo$C_{1-3}$alkyl" shall denote $C_{1-3}$alkyl as defined before, substituted with 1, 2 3 or where possible with more halo atoms as denied before; "mono- and polyhalo$C_{1-3}$alkyloxy" shall denote an ether radical wherein mono- and polyhalo $C_{1-3}$alkyl is as defined before; "$C_{3-6}$cycloalkyl" shall denote cyclopropyl, cyclobutyl, cyclopentyl and cyclohexyl; "$C_{3-6}$cycloalkanediyl" shall denote a bivalent radical such as cyclopropanediyl, cyclobutanediyl, cyclopentanediyl and cyclohexanediyl.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

It will be appreciated that some of the compounds according to formula (I) and the addition salts, hydrates and solvates thereof may contain one or more centers of chirality and exist as stereoisomeric forms.

Hereinbefore and hereinafter, the term "compound of formula (I)" is meant to include the addition salts, the solvates and the stereoisomers thereof.

The terms "stereoisomers" or "stereochemically isomeric forms" hereinbefore or hereinafter are used interchangeably.

The invention includes all stereoisomers of the compound of Formula (I) either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. If a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

The compounds of Formula (I) co-exist in a dynamic equilibrium with the tautomers of Formula (I-a).

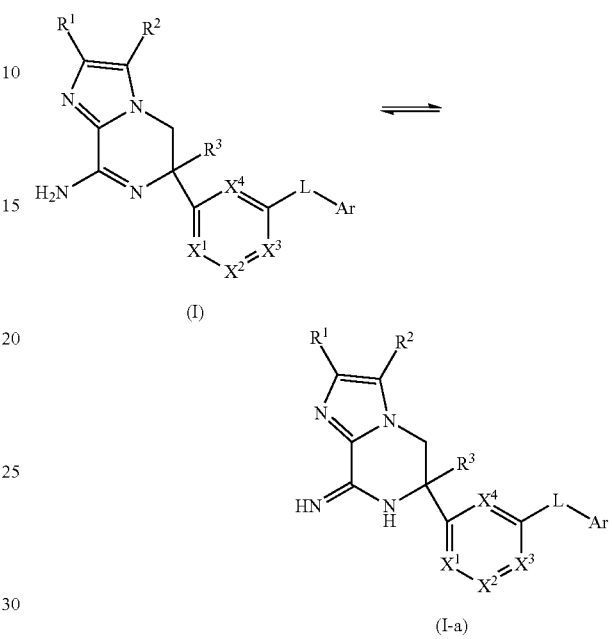

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid. Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006) or according to the nomenclature rules agreed upon by the International Union of Pure and Applied Chemistry (IUPAC) using Advanced Chemical Development, Inc., software (ACD/Name product version 10.01.0.14105, October 2006). In case of tautomeric forms, the name of the depicted tautomeric form of the structure was generated. The other non-depicted tautomeric form is also included within the scope of the present invention.

A. Preparation of the Final Compounds

Experimental Procedure 1

The final compounds according to Formula (I), can be prepared by reacting an intermediate compound of Formula (II) with an appropriate source of ammonia such as, for example, ammonium chloride or aqueous ammonia, according to reaction scheme (1), a reaction that is performed in a suitable reaction-inert solvent, such as, for example, water or methanol, under thermal conditions such as, for example, heating the reaction mixture at 60 to 90° C., for example for 6 to 100 hours. In reaction scheme (1), all variables are defined as in Formula (I).

Reaction Scheme 1

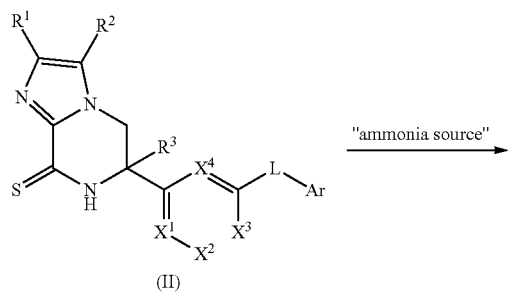

Experimental Procedure 2

The final compounds according to Formula (I-a) wherein L is —N(R$^5$)CO—, can be prepared by reacting an intermediate compound of Formula (III-a) with an intermediate of Formula (IV) according to reaction scheme (2), a reaction that is performed in a suitable reaction-inert solvent, such as, for example, N,N-dimethylformamide, in the presence of a suitable base, such as, for example, K$_3$PO$_4$, a copper catalyst such as, for example, CuI and a diamine such as for example (1R,2R)-(−)-1,2-diaminocyclohexane, under thermal conditions such as, for example, heating the reaction mixture at 180° C., for example for 135 minutes under microwave irradiation. In reaction scheme (2), all variables are defined as in Formula (I) and W is halo.

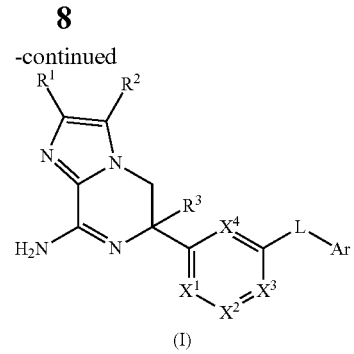

Reaction Scheme 2

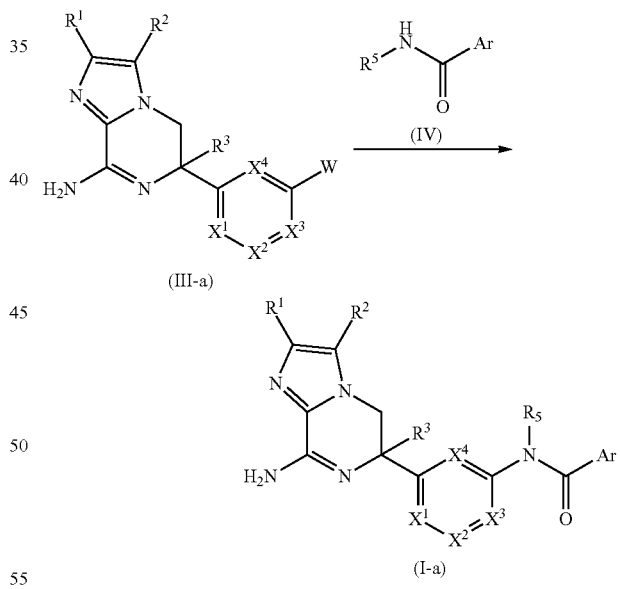

Experimental Procedure 3

Additionally, the final compounds according to Formula (I-a), can be prepared by reacting an intermediate compound of Formula (III-b) with an intermediate of Formula (V) according to reaction scheme (3), a reaction that is performed in a suitable reaction-inert solvent, such as, for example, dichloromethane or methanol, optionally in the presence of a suitable base, such as, for example, N,N-diisopropylethyl amine, and in the presence of a condensation agent such as for example 2-(1H-7-aza-benzotriazol-1-yl)-N,N,N',N'-tetramethyl uronium hexafluorophosphate [HATU, CAS 148893-10-1] or 4-(4,6-dimethoxy-1,3,5-triazin-2-yl)-4-methylmorpholinium chloride [DMTMM, CAS 3945-69-5], under thermal conditions such as, for example, stirring the reaction mixture at 25° C., for example for 2 to 18 hours. In reaction scheme (3), all variables are defined as in Formula (I).

Reaction Scheme 3

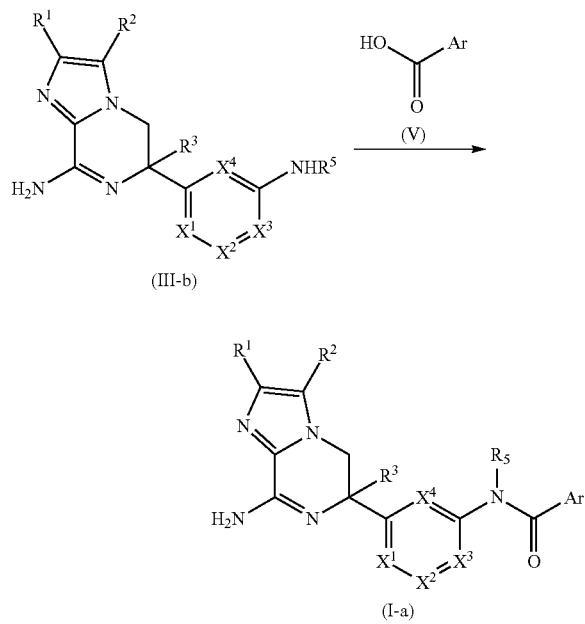

(I-a)

Experimental Procedure 4

Additionally, the final compounds according to Formula (I-a), can be prepared by reacting an intermediate compound of Formula (III-b) with an intermediate of Formula (VI) according to reaction scheme (4), a reaction that is performed in a suitable reaction-inert solvent, such as, for example, dichloromethane, in the presence of a suitable base, such as, for example, pyridine, under thermal conditions such as, for example, stirring the reaction mixture at 25° C., for example for 2 hours. In reaction scheme (4), all variables are defined as in Formula (I) and Y is halo.

Reaction Scheme 4

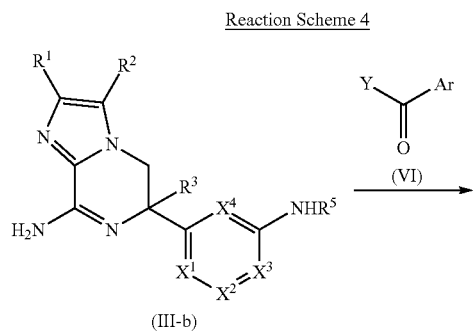

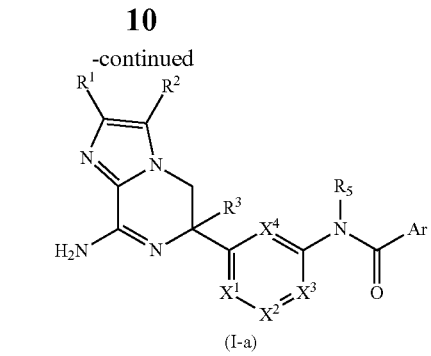

(I-a)

Experimental Procedure 5

The final compounds according to Formula (I-b) wherein L is a bond, can be prepared by reacting an intermediate compound of Formula (III-a) with an intermediate of Formula (VII) according to reaction scheme (5), a reaction that is performed in a suitable reaction-inert solvent, such as, for example, mixtures of inert solvents such as, for example, 1,4-dioxane/ethanol, in the presence of a suitable base, such as, for example, $K_2CO_3$, a Pd-complex catalyst such as, for example, tetrakis(triphenyl-phosphine)palladium (0) [CAS 14221-01-3] under thermal conditions such as, for example, heating the reaction mixture at 80° C., for example for 20 hours or for example, heating the reaction mixture at 150° C., for 10 minutes to 30 minutes under microwave irradiation. In reaction scheme (5), all variables are defined as in Formula (I) and W is, halo. $R^6$ and $R^7$ may be hydrogen or alkyl, or may be taken together to form for example a bivalent radical of formula —$CH_2CH_2$—, —$CH_2CH_2CH_2$—, or —$C(CH_3)_2C(CH_3)_2$—.

Reaction Scheme 5

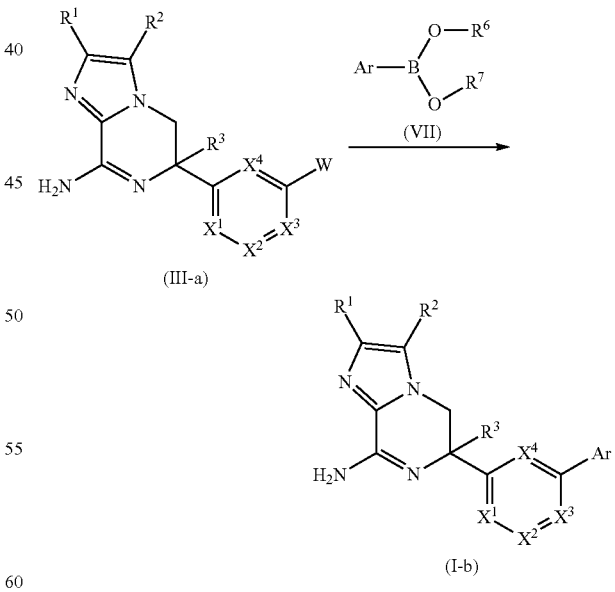

A number of intermediates and starting materials in the foregoing preparations are known compounds which may be prepared according to art-known methodologies of preparing said or similar compounds and some intermediates are new. A number of such preparation methods will be described hereinafter in more detail.

Experimental Procedure 6

Additionally, the final compounds according to Formula (I-a) wherein $R^1$ is CN, hereby named a compound of Formula (I-d), can be prepared by reacting an compound of Formula (I-c), wherein Y is Br or I with zinc cyanide and sodium cyanide according to reaction scheme (6), a reaction that is performed in a suitable reaction-inert solvent, such as, for example, a mixture of dimethylformamide and toluene, in the presence of a suitable coupling reagent, such as, for example, tetrakis(triphenylphosphine)-palladium(0), under thermal conditions such as, for example, heating the reaction mixture at 110° C., for example for 16 to 21 hours. In reaction scheme (6), all variables are defined as in Formula (I) and $Z^1$ is a protecting group of amines such as, for example, tert-butoxycarbonyl group.

Reaction Scheme 6

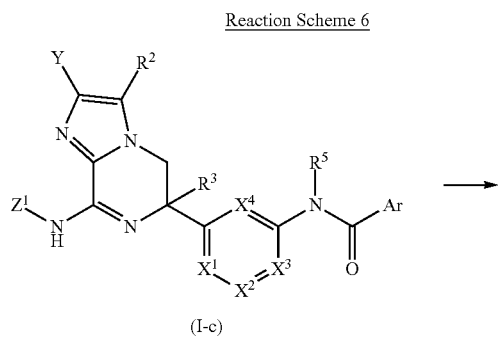

Experimental Procedure 7

Additionally, the final compounds according to Formula (I-a), can be prepared by deprotection of an intermediate compound of Formula (I-e) with an appropriate acid such as, for example trifluoroacetic acid, according to reaction scheme (7), a reaction that is performed in a suitable reaction-inert solvent, such as, for example, dichloromethane, under thermal conditions such as, for example, stirring the reaction mixture at 25° C., for example for 30 minutes. In reaction scheme (7), all variables are defined as in Formula (I) and $Z^1$ is a protecting group of amines such as, for example, tert-butoxycarbonyl group.

Reaction Scheme 7

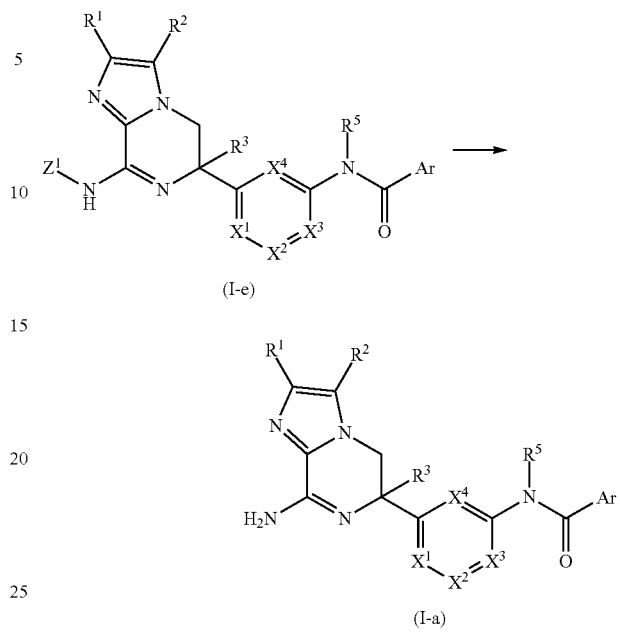

B. Preparation of the Intermediate Compounds

Experimental Procedure 8

The intermediates according to Formula (II) can be prepared by reacting an intermediate compound of Formula (VIII) with a suitable sulphur donating reagent for the synthesis of thioamides such as, for example, phosphorous pentasulfide or 2,4-bis-(4-methoxyphenyl)-1,3-dithia-2,4-diphosphetane 2,4-disulfide [Lawesson's reagent, CAS 19172-47-5] according to reaction scheme (8), a reaction that is performed in a reaction inert solvent, such as for example, tetrahydrofuran or toluene, optionally in the presence of a suitable base such as, for example, pyridine, under thermal conditions such as, for example, heating the reaction mixture at 90° C., for example for 18 hours. In reaction scheme (6), all variables are defined as in Formula (I).

Reaction Scheme 8

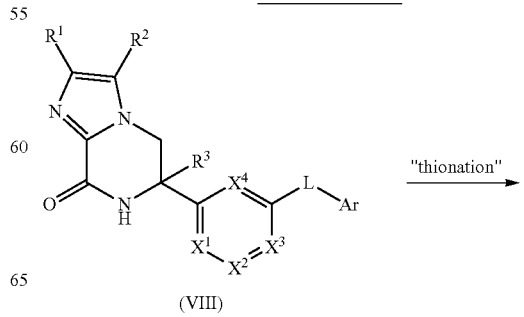

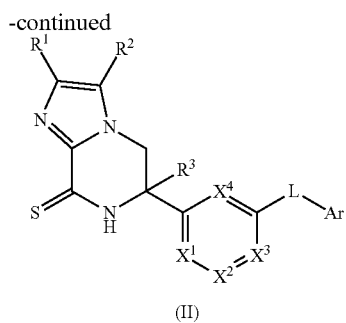

(II)

Experimental Procedure 9

The intermediates according to Formula (VIII) wherein L is a bond, hereby named an intermediate of formula (VIII-a) can be prepared by reacting an intermediate compound of Formula (IX-a) with an intermediate of Formula (VII) according to reaction scheme (9), a reaction that is performed in a suitable mixture of inert solvents such as, for example, 1,4-dioxane/water, in the presence of a suitable base, such as, for example, aqueous $Na_2CO_3$, a Pd-complex catalyst such as, for example, tetrakis(triphenylphosphine) palladium (0) [CAS 14221-01-3] under thermal conditions such as, for example, heating the reaction mixture at 80° C., for example for 20 hours or for example, heating the reaction mixture at 150° C., for example for 15 to 30 minutes under microwave irradiation. In reaction scheme (7), all variables are defined as in Formula (I) and W is halo. $R^6$ and $R^7$ may be hydrogen or alkyl, or may be taken together to form for example a bivalent radical of formula —$CH_2CH_2$—, —$CH_2CH_2CH_2$—, or —$C(CH_3)_2C(CH_3)_2$—.

Reaction Scheme 9

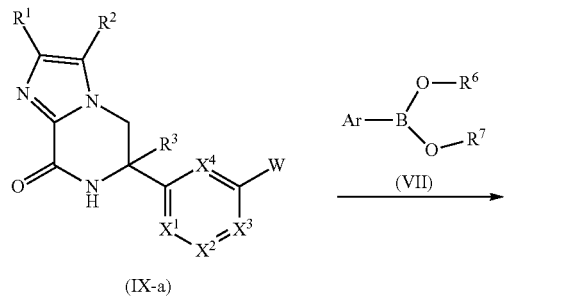

Experimental Procedure 10

The intermediates according to Formula (III-b) can be prepared from the corresponding intermediate compounds of Formula (III-a) following art-known Buchwald-Hartwig type coupling procedures according to reaction scheme (10). Said coupling may be conducted by treatment of intermediate compounds of Formula (III-a) with an intermediate of Formula (X-a) in a suitable reaction-inert solvent, such as, for example, ethanol or mixtures of inert solvents such as, for example, 1,2-dimethoxy-ethane/water/ethanol, in the presence of a suitable base, such as, for example, aqueous $K_3PO_4$ or $Cs_2CO_3$, a Pd-complex catalyst such as, for example, [1,1'-bis(diphenyl-phosphino)ferrocene]-dichloro-palladium(II) [CAS 72287-26-4] or trans-bis(dicyclo-hexylamine)palladium diacetate [DAPCy, CAS 628339-96-8] under thermal conditions such as, for example, heating the reaction mixture at 80° C., for example for 20 hours or for example, heating the reaction mixture at 130° C., for example for 10 minutes under microwave irradiation. In reaction scheme (8), all variables are defined as in Formula (I) and W is halo. $R^5$ is hydrogen or $C_{1-3}$alkyl.

Reaction Scheme 10

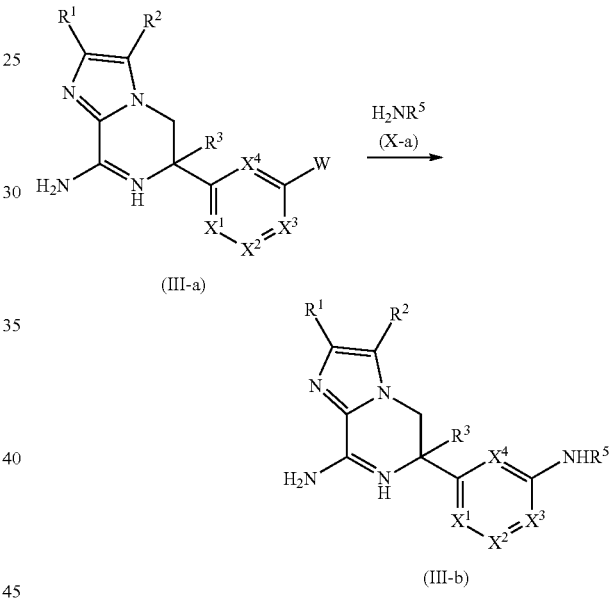

Experimental Procedure 11

Additionally, the intermediates according to Formula (III-b) wherein $R^5$ is hydrogen can be prepared from the corresponding intermediates of Formula (III-c) following art-known nitro-to-amino reduction procedures according to reaction scheme (11). Said reduction may conveniently be conducted following art-known catalytic hydrogenation procedures. For example, said reduction may be carried out by stirring the reactants under a hydrogen atmosphere and in the presence of an appropriate catalyst such as, for example, palladium-on-charcoal, platinum-on-charcoal, Raney-nickel and the like catalysts. Suitable solvents are, for example, water, alkanols, e.g. methanol, ethanol and the like, esters, e.g. ethyl acetate and the like. In order to enhance the rate of said reduction reaction it may be advantageous to elevate the temperature and/or the pressure of the reaction mixture. Undesired further hydrogenation of certain functional groups in the reactants and the reaction products may be prevented by the addition of a catalyst poison such as, for example, thiophene and the like, to the reaction mixture. In reaction scheme (11), all variables are defined as in Formula (I).

Reaction Scheme 11

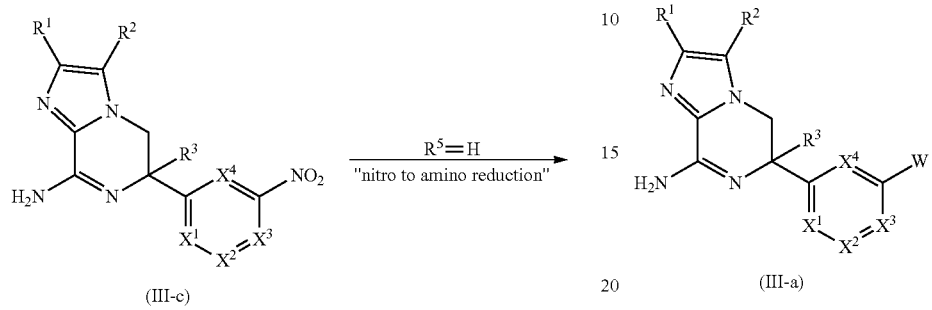

(III-c)

(III-b)

Experimental Procedure 12

The intermediates according to Formula (III-b) can be prepared from the corresponding intermediate of Formula (III-a) following art-known Buchwald-Hartwig type coupling procedures between an intermediate of formula (III-a) and (X-b) to give an intermediate of Formula (III-d), followed by hydrolysis of (III-d) to give (III-a) according to reaction scheme (12). Said Buchwald-Hartwig coupling may be conducted by treatment of intermediate compounds of Formula (III-a) with an intermediate of Formula (X-b) in a suitable reaction-inert solvent, such as, for example, toluene, in the presence of a suitable base, such as, for example, sodium tert-butoxide, a Pd-complex catalyst such as, for example, tris(dibenzylideneacetone)dipalladium(0) [Pd$_2$(dba)$_3$, CAS 51364-51-3], a phosphine-ligand such as, for example, racemic-2,2'-bis(diphenylphosphino)-1,1'-binaphthyl [rac-BINAP, CAS 98327-87-8] under thermal conditions such as, for example, heating the reaction mixture at 90° C., for example for 18 hours. The hydrolysis of (III-d) to (III-a) can be carried out under acidic conditions, for example by treatment with HCl in 2-propanol at room temperature for 1-4 hours. In reaction scheme (12), all variables are defined as in Formula (I) and W is halo. R$^5$ is diphenylmethylidene.

Reaction Scheme 12

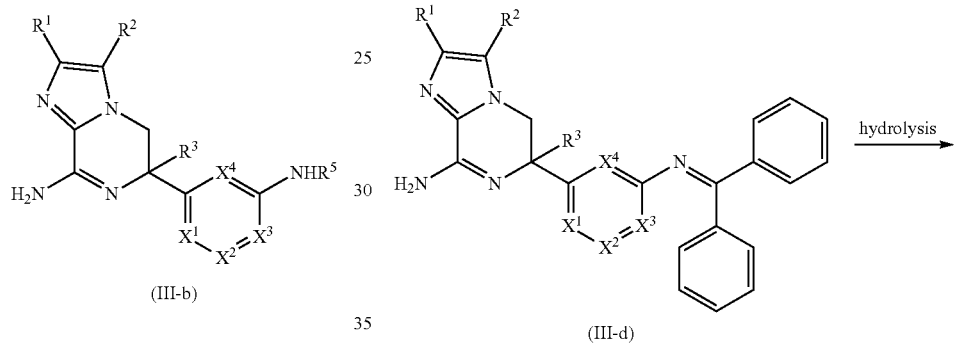

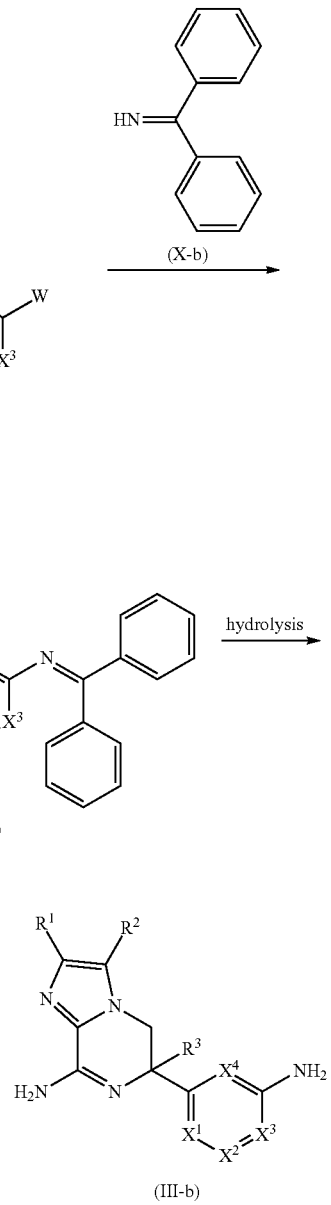

(III-b)

Experimental Procedure 13

The intermediates according to Formula (III-b) can be prepared from the corresponding intermediate compounds of Formula (III-a) according to reaction scheme (13), a reaction that is performed in a suitable reaction-inert solvent, such as, for example, dimethyl sulfoxide, in the presence of sodium azide [CAS 26628-22-8], a suitable copper salt such as, for example copper (I) iodide [CAS 7681-65-4], a suitable base such as, for example, Na$_2$CO$_3$, and a suitable diamine ligand such as, for example, N,N'-dimethylethylenediamine [CAS 110-70-3] under thermal conditions such as, for example, heating the reaction mixture at 110° C., for example for 3 to 6 hours. In reaction scheme (13), all variables are defined as in Formula (I) and W is halo.
Reaction Scheme 13
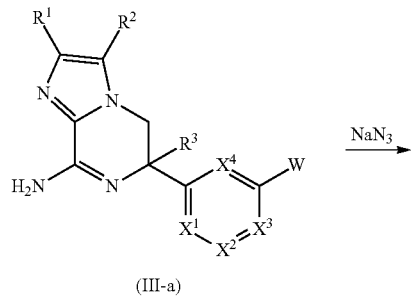
(III-a)
-continued
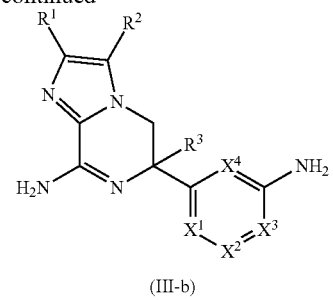
(III-b)
Experimental Procedure 14
The intermediate compounds of Formula (III-a) and (III-c) can generally be prepared following the reaction steps shown in the reaction schemes (14) and (15) below.
Reaction Scheme 14
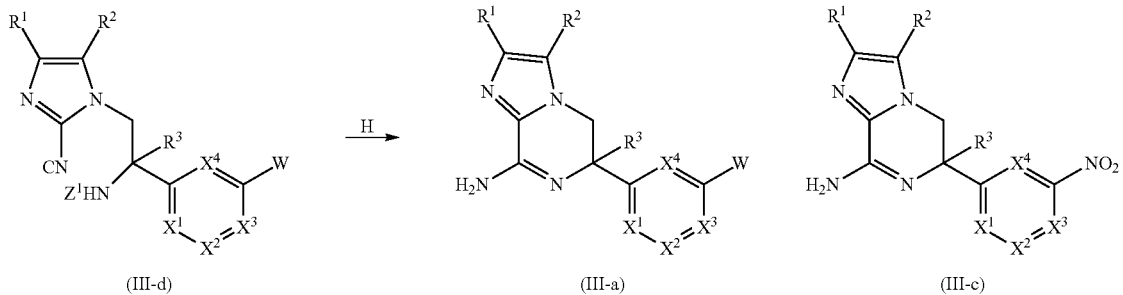
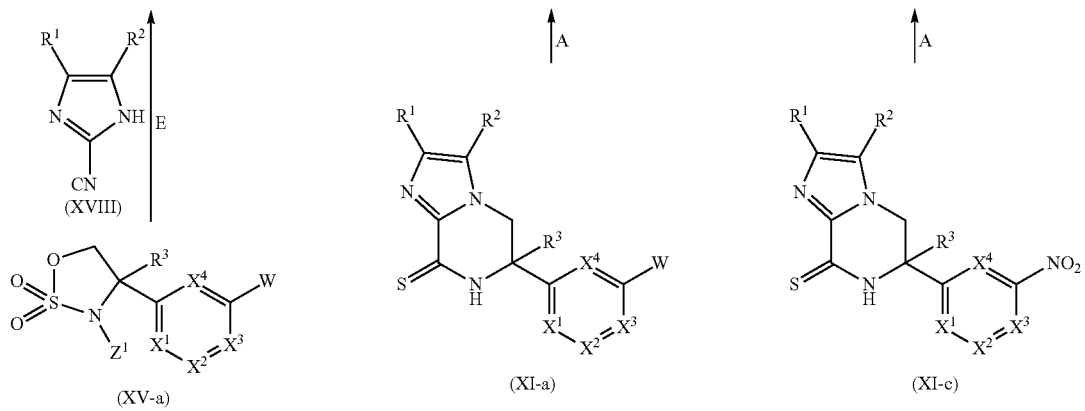

-continued

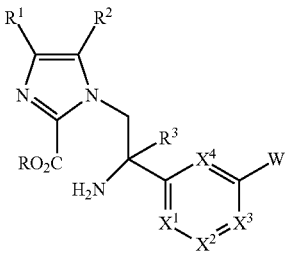

(XII-a)

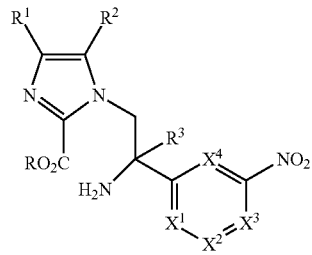

(XII-c)

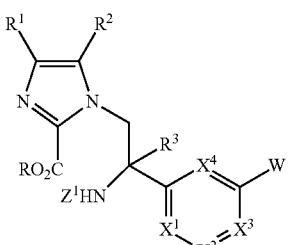

(XIII-a)

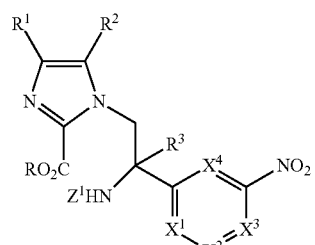

(XIII-c)

A: Thioamide-to-amidine conversion
B: Amide-to-thioamide conversion (thionation)
C and H: Cyclization
D: Removing any N-protecting groups $Z^1$.
E: Alkylation The amidine derivatives in the above reaction scheme (14) may be conveniently prepared from the corresponding thioamide derivatives following art-known thioamide-to-amidine conversion procedures (reaction step A). Said conversion may conveniently be conducted by treatment of the said thioamides with an ammonia source such as, for example, ammonium chloride or aqueous ammonia, in a suitable reaction-inert solvent such as, for example, water or methanol and the like, under thermal conditions such as, for example, heating the reaction mixture at 60 to 90° C., for example for 6 to 100 hours.

Alternatively, the amidine derivatives in the above reaction scheme (14) can be prepared from the corresponding intermediate compounds of Formula (XIII-d) following art-known cyclization procedures (reaction step H). Said cyclization may conveniently be conducted by treatment of intermediate compounds of Formula (XIII-d) with a suitable acid, such as hydrochloric acid 4 M in dioxane, or TFA under thermal conditions such as, for example, heating the reaction mixture between 25° C. and 70° C. for example for 2 to 5 hours.

The thioamide derivatives in the above reaction scheme (14) can be prepared from amide derivatives following art-known thionation procedures (reaction step B). Said conversion may conveniently be conducted by treatment of the said amides with a thionation agent such as, for example, phosphorous pentasulfide or 2,4-bis-(4-methoxyphenyl)-1,3-dithia-2,4-diphosphetane 2,4-disulfide [Lawesson's reagent, CAS 19172-47-5], in a reaction inert solvent such as, for example, tetrahydrofuran or 1,4-dioxane and the like, in the presence of a suitable base like pyridine under thermal conditions such as, for example, heating the reaction mixture at 50 to 100° C., for example for 24 hours.

The amide derivatives of Formula (IX-a) and (IX-c) in the above reaction scheme (14) can be prepared from the corresponding intermediate compounds of Formula (XII-a) and (XII-c) following art-known cyclization procedures (reaction step C). Said cyclization may conveniently be conducted by treatment of intermediate compounds of Formula (XII-a) and (XII-c) with a suitable base, such as sodium methoxide or potassium carbonate, in a suitable reaction solvent, such as for example methanol and the like, at −80° C. to 100° C., preferably −15° C. to 60° C. for 30 minutes to 100 hours, preferably 1 hour to 24 hours. Alternatively, standard conditions for amide formation from esters can be used, by treatment of intermediate compounds of Formula (XII-a) and (XII-c) with a Lewis acid, such as for example, trimethylaluminium in a suitable inert solvent, such as for example tetrahydrofuran under thermal conditions, such as for example, heating the reaction at 120° C. for 30 minutes, under microwave irradiation.

The intermediate compounds of Formula (XII-a) and (XII-c) in the above reaction scheme (14) can be prepared from the corresponding intermediate compounds of Formula (XIII-a) and (XIII-c) by removal of the protecting group $Z^1$ being carried out according to processes known in the art.

Reaction Scheme 15

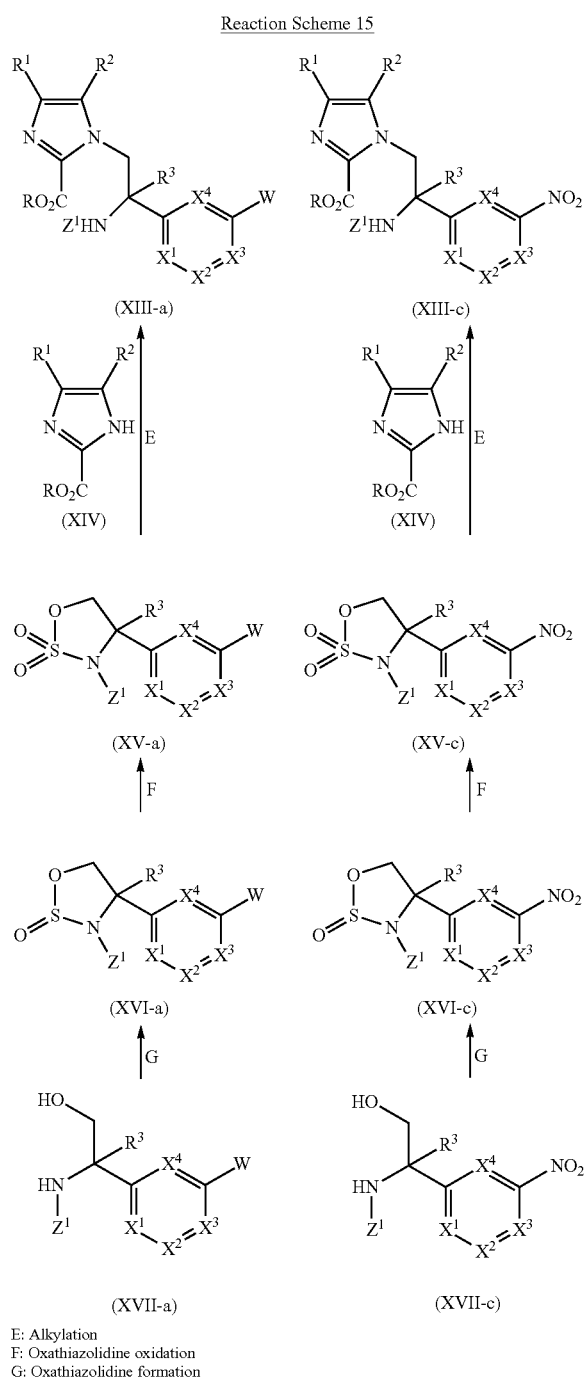

E: Alkylation
F: Oxathiazolidine oxidation
G: Oxathiazolidine formation

The intermediates according to Formula (XIII-a), (XIII-c) and (XIII-d) in the above reaction schemes (14) and (15) can be prepared from the corresponding intermediate compounds of Formula (XV-a) and (XV-c), wherein $Z^1$ is a protecting group of amines such as, for example, the tert-butoxycarbonyl group, following art-known alkylation procedures (reaction step E). Said alkylation may conveniently be conducted by treatment of XIV or XVIII with the corresponding intermediate compounds of Formula (XV-a) and (XV-c) with a suitable base such as, for example, sodium hydride, cesium carbonate, potassium carbonate or 1,8-diazabicyclo[5.4.0]-undec-7-ene, in a suitable inert solvent such as, for example, N,N-dimethyl formamide, acetonitrile or tetrahydrofuran, at low temperature such as, for example, 0° C. for 30 minutes and then at a temperature such as, for example, 60° C. to 100° C. for 24 hours to 100 hours or for example, heating the reaction mixture at 130° C., for example for 30 minutes to 45 minutes under microwave irradiation.

The intermediates according to Formula (XV-a) and (XV-c) in the above reaction scheme (15) can be prepared by reacting the intermediate compounds of Formula (XVI-a) and (XVI-c) following art-known oxidation procedures (reaction step F). Said oxidation may conveniently be conducted by treatment of the corresponding intermediate compounds of Formula (XVI-a) and (XVI-c) with an oxidant agent such as, for example, sodium periodate in a suitable inert solvent such as, for example, acetonitrile/water, in the presence of ruthenium (III) chloride [CAS: 10049-08-8] at a temperature such as, for example, 25° C., for example for 2 hour.

The intermediates according to Formula (XVI-a) and (XVI-c) in the above reaction scheme (15) can be prepared by reacting the intermediate compounds of Formula (XVII-a) and (XVII-c) following art-known sulfamidate formation procedures (reaction step G). Said transformation may conveniently be conducted by treatment of the corresponding intermediate compounds of Formula (XVII-a) and (XVII-c) with thionyl chloride, in the presence of a base such as, for example, pyridine, in a suitable reaction-inert solvent, such as, for example, acetonitrile, at low temperature such as, for example, −40° C., for example for 30 minutes and then at a temperature such as, for example, 25° C., for example for 24 to 72 hour.

The intermediates compounds of Formula (XVII-a) and (XVII-c), wherein $Z^1$ is a protecting group of amines such as, for example, the tert-butoxycarbonyl group, can generally be prepared following art-known Strecker type procedures described in literature.

Experimental Procedure 16

The intermediate compounds of Formula (XVIII) can generally be prepared following the reaction steps shown in the reaction scheme (16) below.

Reaction Scheme 16

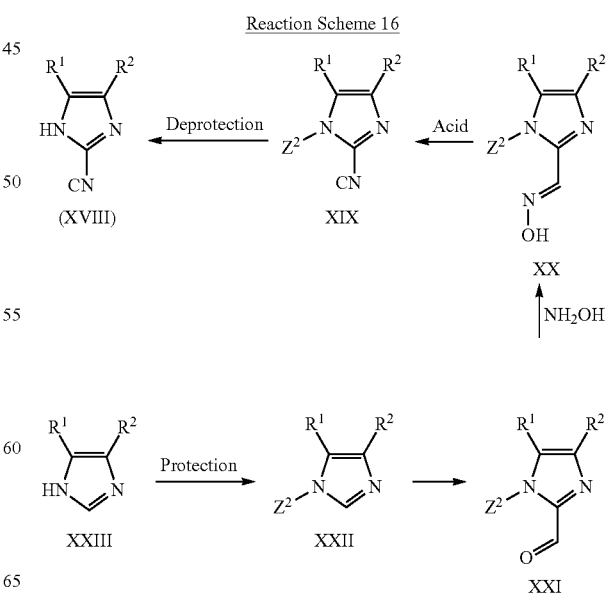

The cyano derivatives of formula (XVIII) in the above reaction scheme (16) may be conveniently prepared by deprotection of the intermediate compounds of Formula (XIX) (wherein $Z^2$ is a protecting group of imidazoles such as, for example, 2-(trimethylsilyl)ethoxymethyl) following art-known procedures. Said deprotection may conveniently be conducted by treatment with tetrabutylammonium fluoride, under thermal conditions such as, for example, heating the reaction mixture at 65° C., for example for 4 hours.

The intermediates according to formula (XIX) in the above reaction scheme (16) can be prepared by reacting the intermediate compounds of formula (XX) with a suitable acid such as for example, acetic anhydride, under thermal conditions such as, for example, heating the reaction mixture at 140° C. for example for 6 hours.

The intermediates according to formula (XX) in the above reaction scheme (16) can be prepared by reacting the intermediate compounds of formula (XXI) with hydroxylamine hydrochloride, in the presence of a suitable reaction-inert solvent, such as, for example, distilled water, under thermal conditions such as, for example, heating the reaction mixture at 70° C. for example for 1 hour.

The intermediates according to formula (XXI) in the above reaction scheme (16) can be prepared by reacting the intermediate compounds of formula (XXII) following art-known carbonylating procedures. Said carbonylation may conveniently be conducted by treatment of the corresponding intermediate of Formula (XXII) with dimethylformamide, in the presence of a base such as, for example, butyllithium or lithium diisoprpylamide, in a suitable reaction-inert solvent, such as, for example, tetrahydrofuran, under thermal conditions such as, for example, cooling the reaction mixture at −78° C. for example for 1 to 2 hours.

The intermediates according to formula (XXII) in the above reaction scheme (16) can be prepared by protection of the intermediate compounds of formula (XXIII). Said protection may conveniently be conducted by treatment of the corresponding intermediate of Formula (XXIII) with 2-(trimethylsilyl)ethoxymethyl chloride in a suitable reaction-inert solvent, such as, for example, tetrahydrofuran, under thermal conditions such as, for example, stirring the reaction mixture at 25° C. for example for 30 minutes.

The intermediates according to formula (XIII) in the above reaction scheme (16) can be obtained commercially.

Experimental Procedure 17

The intermediate compounds of Formula (III-b), wherein $R^{1A}$ is H or Cl, and $R^2$ is CN, hereby named as intermediate of formula (III-e), which can generally be prepared following the reaction steps shown in the reaction scheme (17) below.

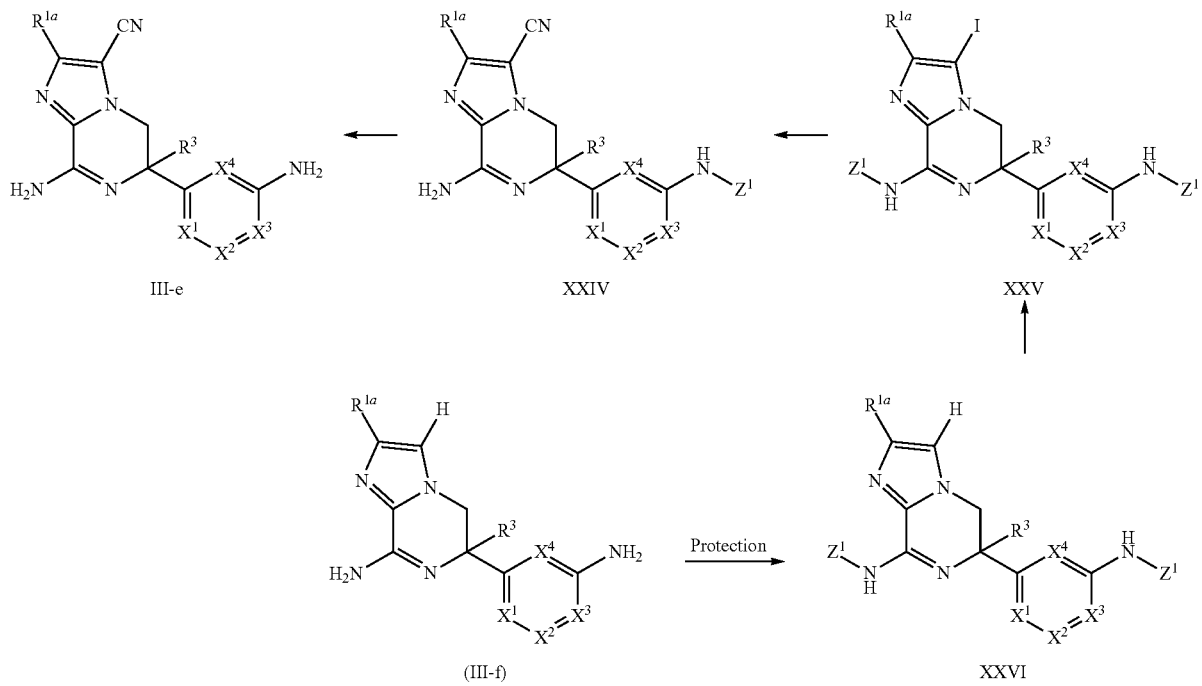

Reaction Scheme 17

The intermediates according to Formula (III-e) in the above reaction scheme (17) may be conveniently prepared by deprotection of the intermediate compounds of Formula (XXIV) (wherein $Z^1$ is a protecting group of amines such as, for example, the tert-butoxycarbonyl) following art-known procedures. Said deprotection may conveniently be conducted by treatment with trifluoroacetic acid, in the presence of a suitable reaction-inert solvent, such as, for example dichloromethane, under thermal conditions such as, for example, stirring the reaction mixture at 25° C., for example for 30 minutes.

The intermediates compounds according to Formula (XXIV), can be prepared by reacting an intermediate compound of Formula (XXV) with zinc cyanide and zinc according to reaction scheme (17), a reaction that is performed in the presence of a suitable coupling reagent, such as, for example, tris(dibenzylideneacetone)dipalladium(0), in the presence of a suitable ligand such as, for example, 1,1'-bis(diphenylphosphino)ferrocene, in a suitable reaction-inert solvent, such as, for example, dimethylacetamide, under thermal conditions such as, for example, heating the reaction mixture at 150° C., for example for 30 minutes under microwave irradiation.

The intermediates according to Formula (XXV) in the above reaction scheme (17) may be conveniently prepared by iodination of the intermediate compounds of Formula (III-f) following art-known procedures. Said halogenation may conveniently be conducted by treatment with iodine, in the presence of a suitable base such as, for example N-butyllithium in a reaction-inert solvent, such as, for example tetrahydrofuran, under thermal conditions such as, for example, cooling the reaction mixture at −78° C., for example for 10 minutes.

The intermediates according to formula (III-f) in the above reaction scheme (17) can be prepared by protection of the intermediate compounds of formula (XXVI). Said protection may conveniently be conducted by treatment of the corresponding intermediate of Formula (XXVI) with di-tert-butyl dicarbonate in the presence of a base such as, for example N,N-diisopropylethylamine in a suitable reaction-inert solvent, such as, for example, dichloromethane, under thermal conditions such as, for example, stirring the reaction mixture at 25° C. for example for 24 hours.

In reaction scheme (17), $R^{1,4}$ is H, Cl and all other variables are defined as in Formula (I).

Experimental Procedure 18

The intermediate compounds of Formula (III-b), wherein $R^1$ is H, $R^2$ is $CF_2$, hereby named as intermediate of formula (III-g) can generally be prepared following the reaction steps shown in the reaction scheme (18) below.

by deprotection of the intermediate compounds of Formula (XXVII) (wherein $Z^1$ is a protecting group of amines such as, for example, the tert-butoxycarbonyl) following art-known procedures. Said deprotection may conveniently be conducted by treatment with trifluoroacetic acid, in the presence of a suitable reaction-inert solvent, such as, for example dichloromethane, under thermal conditions such as, for example, stirring the reaction mixture at 25° C., for example for 30 minutes.

The intermediates compounds according to Formula (XXVII), can be prepared by reacting an intermediate compound of Formula (XXVIII) with diethylaminosulfur trifluoride according to reaction scheme (18), in a suitable reaction-inert solvent, such as, for example, dichloromethane, under thermal conditions such as, for example, stirring the reaction mixture at 25° C. for example for 16 hours.

The intermediates according to Formula (XXVIII) in the above reaction scheme (18) may be conveniently prepared by oxidation of the intermediate compounds of Formula (XXIX) following art-known procedures. Said oxidation may conveniently be conducted by treatment with manganese dioxide, in a reaction-inert solvent, such as, for example dichloromethane, under thermal conditions such as, for example, heating the reaction mixture at 25° C. for example for 2 hours.

The intermediates according to Formula (XXIX) in the above reaction scheme (18) may be conveniently prepared by hydroxymethylation of the intermediate compounds of Formula (XXX) following art-known procedures. Said hydroxymethylation may conveniently be conducted by treatment with paraformaldehyde, in the presence of a suitable base such as, for example N-butyllithium in a reaction-inert solvent, such as, for example tetrahydrofuran, Reaction Scheme 18

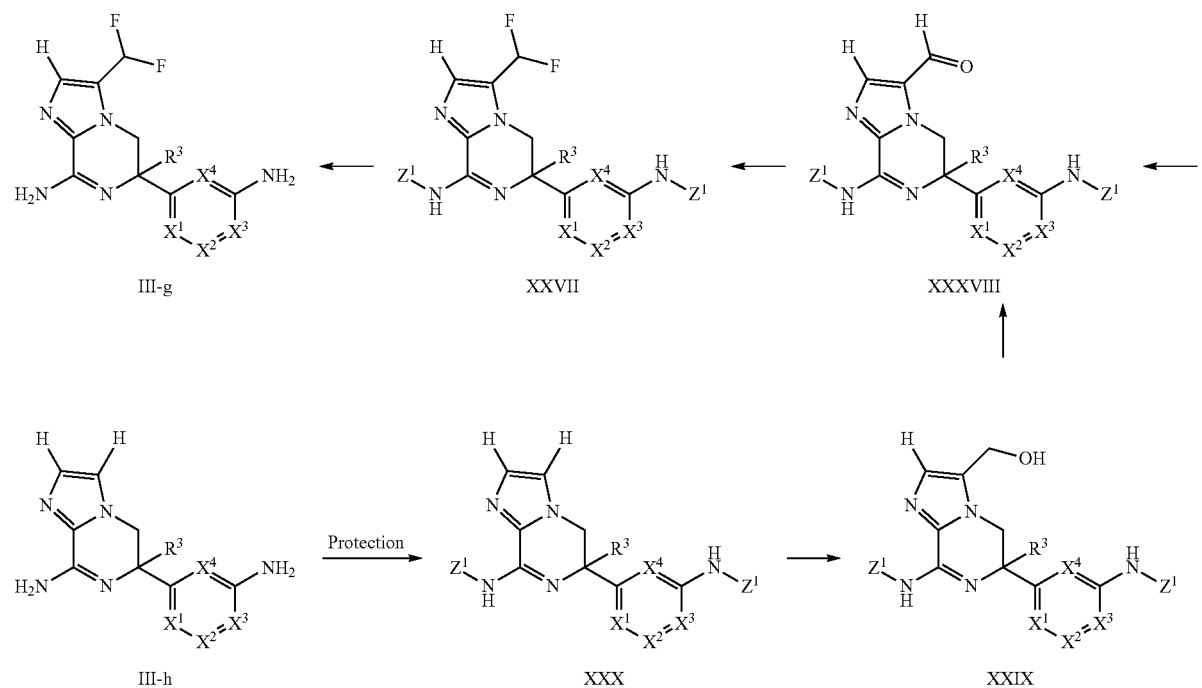

The intermediates according to Formula (III-g) in the above reaction scheme (18) may be conveniently prepared under thermal conditions such as, for example, cooling the reaction mixture at −78° C., for example for 10 minutes.

The intermediates according to formula (XXX) in the above reaction scheme (18) can be prepared by protection of the intermediate compounds of formula (III-h). Said protection may conveniently be conducted by treatment of the corresponding intermediate of Formula (III-h) with di-tert-butyl dicarbonate in the presence of a base such as, for example N,N-diisopropylethylamine in a suitable reaction-inert solvent, such as, for example, dichloromethane, under thermal conditions such as, for example, stirring the reaction mixture at 25° C. for example for 24 hours.

In reaction scheme (18), $Z^1$ is a protecting group of amines such as, for example, the tert-butoxycarbonyl and all other variables are defined as in Formula (I).

Experimental Procedure 19

The intermediate compounds of Formula (I-e) can generally be prepared following the reaction steps shown in the reaction scheme (19) below.

Reaction Scheme 20

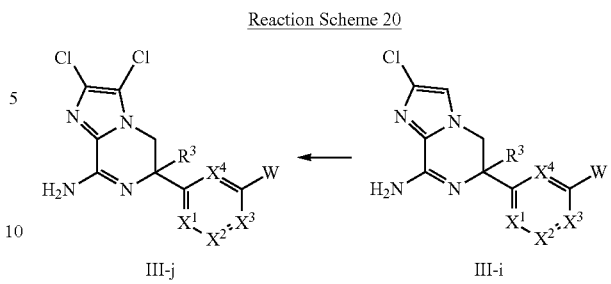

The intermediates according to formula (III-j) in the above reaction scheme (20) can be prepared by chlorination of the intermediate compounds of formula (III-i). Said chlorination may conveniently be conducted by treatment of the corresponding intermediate of Formula (III-i) with N-chlorosuccinimide in a suitable reaction-inert solvent, Reaction Scheme 19

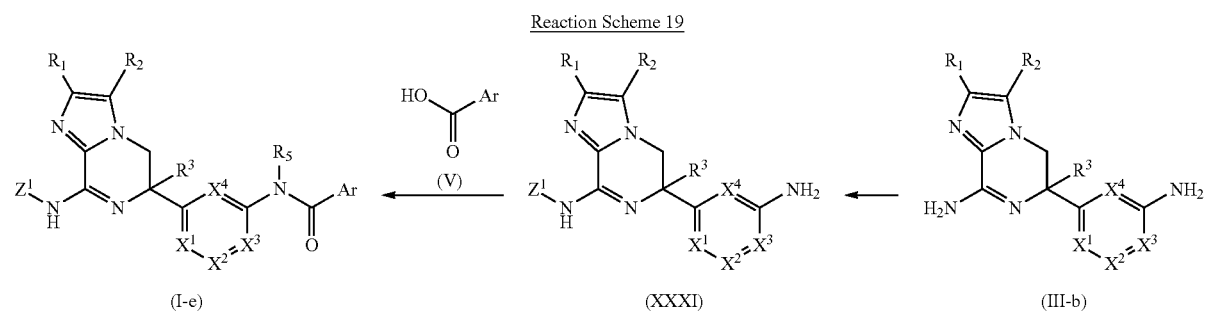

The intermediates according to formula (XXXI) in the above reaction scheme (19) can be prepared by protection of the intermediate compounds of formula (III-b). Said protection may conveniently be conducted by treatment of the corresponding intermediate of Formula (III-b) with di-tert-butyl dicarbonate in a suitable reaction-inert solvent, such as, for example, dichloromethane, under thermal conditions such as, for example, stirring the reaction mixture at 25° C. for example for 24 hours.

The intermediates according to formula (I-e) in the above reaction scheme (19) can be prepared by reacting an intermediate compound of Formula (XXXI) with an intermediate of Formula (V) according to reaction scheme (19), a reaction that is performed in a suitable reaction-inert solvent, such as, for example, dichloromethane or methanol, in the presence of a suitable base, such as, for example, N,N-diisopropylethyl amine, in the presence of a condensation agent such as for example 2-(1H-7-azabenzotriazol-1-yl)-N,N,N',N'-tetramethyluronium hexafluorophosphate [HATU, CAS 148893-10-1] or 4-(4,6-dimethoxy-1,3,5-triazin-2-yl)-4-methylmorpholinium chloride [DMTMM, CAS 3945-69-5], under thermal conditions such as, for example, stirring the reaction mixture at 25° C., for example for 2 to 18 hours. In reaction scheme (19), $Z^1$ is a suitable N-protecting group and all other variables are defined as in Formula (I).

Experimental Procedure 20

The intermediate compound of Formula (III-b), wherein $R^1$ is Cl, $R^2$ is Cl, hereby named an intermediate of formula (III-j), can generally be prepared following the reaction step shown in the reaction scheme (20) below.

such as, for example, acetic acid, under thermal conditions such as, for example, heating the reaction mixture at 80° C. for example for 16 hours. In reaction scheme (20), all variables are defined as in Formula (I).

Pharmacology

The compounds of the present invention and the pharmaceutically acceptable compositions thereof inhibit BACE and therefore may be useful in the treatment or prevention of Alzheimer's Disease (AD), mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid.

The invention relates to a compound according to the general Formula (I), a stereoisomeric form thereof or a pharmaceutically acceptable acid or base addition salt or a solvate thereof, for use as a medicament.

The invention also relates to a compound according to the general Formula (I), a stereoisomeric form thereof or a pharmaceutically acceptable acid or base addition salt or a solvate thereof, for use in the treatment or prevention of diseases or conditions selected from the group consisting of AD, MCI, senility, dementia, dementia with Lewy bodies, cerebral amyloid angiopathy, multi-infarct dementia, Down's syndrome, dementia associated with Parkinson's disease and dementia associated with beta-amyloid.

The invention also relates to the use of a compound according to the general Formula (I), a stereoisomeric form thereof or a pharmaceutically acceptable acid or base addition salt or a solvate thereof, for the manufacture of a medicament for the treatment or prevention of any one of the disease conditions mentioned hereinbefore.

In view of the utility of the compound of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), a stereoisomeric form thereof, a pharmaceutically acceptable addition salt or solvate thereof, to a warm-blooded animal, including a human.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

Pharmaceutical Compositions

The present invention also provides compositions for preventing or treating diseases in which inhibition of beta-secretase is beneficial, such as Alzheimer's disease (AD), mild cognitive impairment, senility, dementia, dementia with Lewy bodies, Down's syndrome, dementia associated with stroke, dementia associated with Parkinson's disease and dementia associated with beta-amyloid. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The following examples are intended to illustrate but not to limit the scope of the present invention.

EXPERIMENTAL PART

Hereinafter, the term 'm.p." means melting point, 'THF' means tetrahydrofuran, DIPE is diisopropylether, 'DMF' means N,N-dimethylformamide, 'DCM' means dichloromethane, 'EtOAc' means ethyl acetate, "AcOH" means acetic acid, "MeOH" means methanol, "EtOH" means ethanol, "rac" means racemic. SFC is supercritical fluid chromatography, "PFA" means perfluoroalkoxy. "DIPEA" means N,N-diisopropylethylamine, "DIPE" means diisopropylether, "DMA" means dimethylacetamide, "DAST" means diethylaminosulfur trifluoride.

Thin layer chromatography (TLC) was carried out on silica gel 60 F254 plates (Merck) using reagent grade solvents. Automated flash column chromatography was performed using ready-to-connect cartridges from Merck, on irregular silica gel, particle size 15-40 μm (normal phase disposable flash columns) on a SPOT or FLASH system from Armen Instrument.

Microwave assisted reactions were performed in a single-mode reactor: Emrys™ Optimizer microwave reactor (Personal Chemistry A.B., currently Biotage).

Hydrogenation reactions were performed in a continuous flow hydrogenator H-CUBE® from ThalesNano Nanotechnology Inc.

Flow reactions were performed in a commercially available Vapourtec R2+R4 modular device with the cool reactor module. Website: http://www.vapourtec.co.uk.

For key intermediates, as well as some final compounds, the absolute configuration of chiral centers (indicated as R and/or S) were established via comparison with samples of known configuration, or the use of analytical techniques suitable for the determination of absolute configuration, such as VCD (vibrational circular dichroism) or X-ray crystallography. When the absolute configuration at a chiral center is unknown, it is arbitrarily designated *R or *S.

A. Preparation of the intermediates

Example A1

Preparation of rac-2-amino-2-(3-bromo-phenyl)-propionitrile

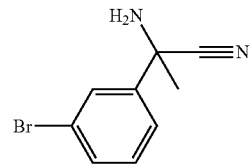

Trimethylsilylcyanide (20 g, 200 mmol) was added to a stirred solution of 3-bromo-acetophenone (20 g, 100 mmol) and $NH_4Cl$ (11 g, 200 mmol) in $NH_3$/MeOH (400 mL). The mixture was stirred at room temperature for 4 days. The solvent was evaporated in vacuo and the residue was taken up in EtOAc (100 mL). The solid was filtered off and the filtrate was evaporated in vacuo to yield rac-2-amino-2-(3-bromo-phenyl)-propionitrile (20 g, 86% yield) that was used in the next step without further purification.

Example A2

Preparation of rac-2-amino-2-(3-bromo-phenyl)-propionic acid methyl ester

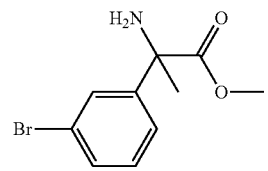

rac-2-amino-2-(3-bromo-phenyl)-propionitrile (20 g, 88.9 mmol) was dissolved in HCl/MeOH (500 mL) and the mixture was refluxed for 4 days. After cooling to room temperature, EtOAc (100 mL) and water (100 mL) were added and the mixture was extracted with EtOAc (2×100 mL). The combined aqueous layers were basified with aqueous ammonia solution until pH 8 and extracted with EtOAc (5×100 mL). The combined organic layers were dried ($Na_2SO_4$), filtered and the solvent was evaporated in vacuo to yield rac-2-amino-2-(3-bromo-phenyl)-propionic acid methyl ester (10.6 g, 46% yield) as an oil.

Example A3

Preparation of rac-2-amino-2-(3-bromo-phenyl)-propan-1-ol

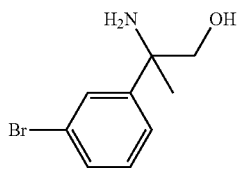

Lithium aluminium hydride (1 M in THF; 22 mL, 22 mmol) was added dropwise to a stirred solution of rac-2-amino-2-(3-bromo-phenyl)-propionic acid methyl ester (7.5 g, 29.1 mmol) in THF (200 ml) at −15° C. The mixture was left to warm up to 0° C. over 1 hour. More THF (150 ml) was added and sat. $Na_2SO_4$ was added dropwise until no more hydrogen was formed. Anhydrous $Na_2SO_4$ was added and stirred overnight at room temperature. The mixture was filtered over diatomaceous earth, rinsed with THF and the solvent was evaporated in vacuo. The crude product was purified by flash column chromatography (silica; 7 M solution of ammonia in MeOH in DCM 0/100 to 3/97). The desired fractions were collected and concentrated in vacuo to yield rac-2-amino-2-(3-bromo-phenyl)-propan-1-ol (5.70 g, 85% yield) as an oil.

Example A4

Preparation of (R)-2-amino-2-(3-bromo-phenyl)-propan-1-ol

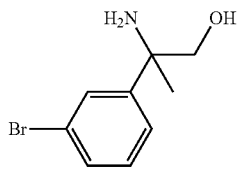

A sample of rac-2-amino-2-(3-bromo-phenyl)-propan-1-ol (15.4 g) was separated into the corresponding enantiomers by preparative SFC on Chiralpak® Daicel AD×250 mm, mobile phase ($CO_2$, MeOH with 0.2% $iPrNH_2$) to yield (R)-2-amino-2-(3-bromo-phenyl)-propan-1-ol (7.21 g, 40% yield).

$α_D$: −14.9° (589 nm, c=0.2946 w/v %, MeOH, 20° C.).

Example A5

Preparation of rac-[1-(3-bromo-phenyl)-2-hydroxy-1-methyl-ethyl]-carbamic acid tert-butyl ester

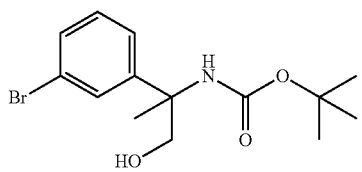 [SMILES: CC(C)(C)OC(=O)NC(C)(CO)c1cccc(Br)c1]

Di-tert-butyldicarbonate (4.84 g, 22.16 mmol) was added portion-wise to a stirred solution of rac-2-amino-2-(3-bromo-phenyl)-propan-1-ol (1.7 g, 7.39 mmol) in a mixture of sat $NaHCO_3$ (15 mL) and THF (15 mL) at 0° C. The mixture was stirred at 0° C. for 10 minutes and at room temperature for 15 hours. The mixture was cooled in an ice/water bath and acidified to pH 1-2 with $KHSO_4$. The organic layer was separated and the aqueous layer was further extracted with EtOAc. The combined organic layers were dried ($MgSO_4$), filtered and the solvent was evaporated in vacuo. The crude product was purified by flash column chromatography (silica; EtOAc in DCM 0/100 to 20/80). The desired fractions were collected and concentrated in vacuo to yield rac-[1-(3-bromo-phenyl)-2-hydroxy-1-methyl-ethyl]-carbamic acid tert-butyl ester (2.36 g, 93% yield) as a colourless oil.

The following intermediate was prepared according to similar synthetic procedures described in examples A1-A5:

Example A6

Preparation of (R) tert butyl [1-(5-bromo-2-fluoro-phenyl)-2-hydroxy-1-methylethyl]carbamate

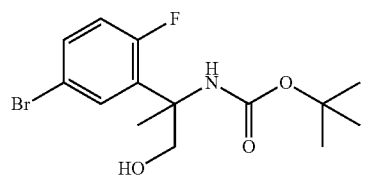 [SMILES: CC(C)(C)OC(=O)NC(C)(CO)c1cc(Br)ccc1F]

From 1-(5-bromo-2-fluorophenyl)ethanone.

Example A7

Preparation of 4-(trifluoromethyl)-1-{[2-(trimethylsilyl)ethoxy]methyl}-1H-imidazole

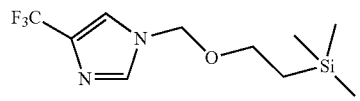

Sodium hydride (60% in mineral oil; 0.4 g, 10 mmol) was added portionwise to a stirred solution of 4-(trifluoromethyl)-1H-imidazole (1.15 g, 8.45 mmol) in THF (19 mL) at 0° C. After stirring at 0° C. for 30 minutes 2-(trimethylsilyl)ethoxymethyl chloride (1.69 g, 10 mmol) was added and the reaction mixture was stirred at room temperature for 30 minutes. Water was added and the product extracted with EtOAc. The organic layer was separated, dried ($MgSO_4$), filtered and the solvent was evaporated in vacuo to yield 4-(trifluoromethyl)-1-{[2-(trimethylsilyl)ethoxy]methyl}-1H-imidazole (2.2 g, 98% yield) that was used in the next step without further purification.

The following intermediate was prepared according to similar synthetic procedures described in examples A7:

Example A8

Preparation of a mixture of 4-iodo-1-{[2-(trimethylsilyl)ethoxy]methyl}-1H-imidazole and 5-iodo-1-{[2-(trimethylsilyl)ethoxy]methyl}-1H-imidazole

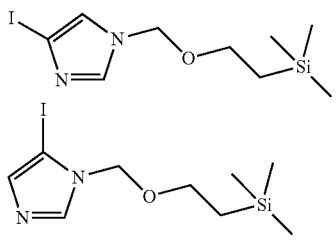

From 4-iodoimidazole.

Example A9

Preparation of 4-(trifluoromethyl)-1-{[2-(trimethylsilyl)ethoxy]methyl}-1H-imidazole-2-carbaldehyde

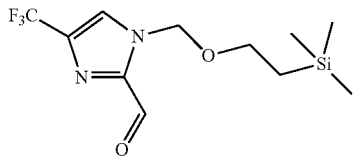 [SMILES: C[Si](C)(C)CCOCn1cc(C(F)(F)F)nc1C=O]

n-Butyllithium (1.6 M in hexane; 7.74 mL, 12.4 mmol) was added drop-wise to a stirred solution of 4-(trifluoromethyl)-1-{[2-(trimethylsilyl)ethoxy]methyl}-1H-imidazole (2.75 g, 10.33 mmol) in THF (76.5 mL) at −78° C. under a nitrogen atmosphere. The mixture was stirred at −78° C. for 10 minutes and then DMF (5.74 mL, 74.1 mmol) was added. The reaction mixture was stirred at −78° C. for 30 minutes and at 0° C. for 1 hour. The mixture was diluted with water and extracted with EtOAc. The organic layer was separated, dried (MgSO$_4$), filtered and the solvent was evaporated in vacuo. The crude product was purified by flash column chromatography (silica; DCM in heptane 0/100 to 60/40). The desired fractions were collected and concentrated in vacuo to yield 4-(trifluoromethyl)-1-{[2-(trimethylsilyl)ethoxy]methyl}-1H-imidazole-2-carbaldehyde (1.6 g, 53% yield).

Example A10

Preparation of 4-(trifluoromethyl)-1-{[2-(trimethylsilyl)ethoxy]methyl}-1H-imidazole-2-carbaldehyde oxime

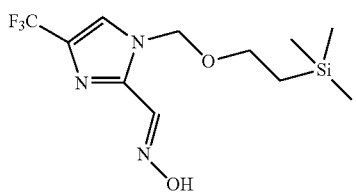 [SMILES: C[Si](C)(C)CCOCn1cc(C(F)(F)F)nc1/C=N/O]

Na$_2$CO$_3$ (0.54 g, 5.1 mmol) was added to a stirred solution of 4-(trifluoromethyl)-1-{[2-(trimethylsilyl)ethoxy]methyl}-1H-imidazole-2-carbaldehyde (1.5 g, 5.1 mmol) and hydroxylamine hydrochloride (0.71 g, 10.2 mmol) in distilled water (10.2 mL). The mixture was stirred at 70° C. for 1 hour and after cooling a precipitate was formed, filtered and washed with additional water to yield 4-(trifluoromethyl)-1-{[2-(trimethyl-silyl)ethoxy]methyl}-1H-imidazole-2-carbaldehyde oxime (1.5 g, 95% yield).

The following intermediate was prepared according to a similar synthetic procedure described in example A10:

Example A11

Preparation of 4-iodo-1-{[2-(trimethylsilyl)ethoxy]methyl}-1H-imidazole-2-carbaldehyde oxime

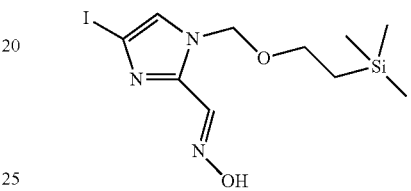

From 4-iodo-1-{[2-(trimethylsilyl)ethoxy]methyl}-1H-imidazole-2-carbaldehyde.

Example A12

Preparation of 4-(trifluoromethyl)-1-{[2-(trimethylsilyl)ethoxy]methyl}-1H-imidazole-2-carbonitrile

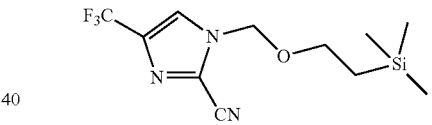

A solution of 4-(trifluoromethyl)-1-{[2-(trimethylsilyl)ethoxy]methyl}-1H-imidazole-2-carbaldehyde oxime (1.4 g, 4.53 mmol) in acetic anhydride (16.7 mL, 176.23 mmol) was stirred at 140° C. for 6 hours. The solvent was concentrated in vacuo and the residue was taken up in EtOAc and washed with Na$_2$CO$_3$ (sat.). The organic layer was separated, dried (MgSO$_4$), filtered and the solvent was evaporated in vacuo to yield 4-(trifluoromethyl)-1-{[2-(trimethylsilyl)ethoxy]methyl}-1H-imidazole-2-carbonitrile (1.15 g, 87% yield). The product was used in the next reaction without further purification.

Example A13

Preparation of 4-(trifluoromethyl)-1H-imidazole-2-carbonitrile

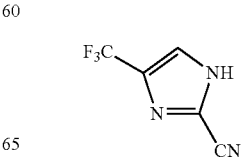

A solution of 4-(trifluoromethyl)-1-{[2-(trimethylsilyl)ethoxy]methyl}-1H-imidazole-2-carbonitrile (1.15 g, 3.95 mmol) in tetrabutylammonium fluoride (1 M in THF; 25.6 mL, 25.6 mmol) in a sealed tube was stirred at 65° C. for 4 hours. The mixture was diluted with EtOAc and treated with a buffer solution of $K_2HPO_4/KH_2PO_4$. The organic layer was separated, and the aqueous phase was washed with additional EtOAc. The combined organic layers were dried ($MgSO_4$), filtered and the solvent evaporated in vacuo. The crude product was purified by flash column chromatography (silica; 7 M solution of ammonia in MeOH in DCM 0/100 to 2/98 and then MeOH in DCM 0/100 to 1/99). The desired fractions were collected and concentrated in vacuo to yield 4-(trifluoromethyl)-1H-imidazole-2-carbonitrile (0.26 g, 41% yield).

The following intermediates were prepared according to similar synthetic procedures described in examples A7-A13:

Example A14

Preparation of 4-chloro-1H-imidazole-2-carbonitrile

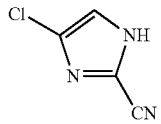

From 4-(chloro)-1H-imidazole.

Example A15

Preparation of 4-bromo-1H-imidazole-2-carbonitrile

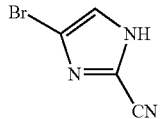

From 4-(bromo)-1H-imidazole.

Example A16

Preparation of a mixture of 4-iodo-1-{[2-(trimethylsilyl)ethoxy]methyl}-1H-imidazole-2-carbaldehyde and 5-iodo-1-{[2-(trimethylsilyl)ethoxy]methyl}-1H-imidazole-2-carbaldehyde

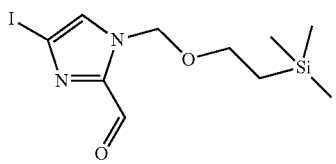

-continued

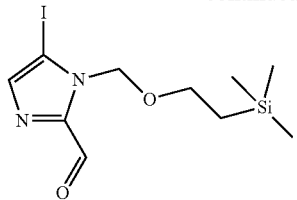

Lithium diisopropylamide (1.8 M; 57.6 mL, 103.6 mmol) was added dropwise to a stirred solution of a mixture of 4-iodo-1-{[2-(trimethylsilyl)ethoxy]methyl}-1H-imidazole and 5-iodo-1-{[2-(trimethylsilyl)ethoxy]methyl}-1H-imidazole (28 g, 86.4 mmol) in THF (640 mL) at −78° C. under a nitrogen atmosphere. The mixture was stirred at −78° C. for 20 minutes and then DMF (48 mL, 620 mmol) was added. The reaction mixture was stirred at −78° C. for 30 minutes and at 0° C. for 2 hours. The mixture was diluted EtOAc and washed with water and brine. The organic layer was separated, dried ($MgSO_4$), filtered and the solvent was evaporated in vacuo to yield a mixture of 4-iodo-1-{[2-(trimethylsilyl)ethoxy]methyl}-1H-imidazole-2-carbaldehyde and 5-iodo-1-{[2-(trimethylsilyl)ethoxy]methyl}-1H-imidazole-2-carbaldehyde (45 g, quantitative yield).

Example A17

Preparation of 4-iodo-1H-imidazole-2-carbonitrile

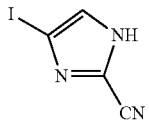

A solution of 4-iodo-1-{[2-(trimethylsilyl)ethoxy]methyl}-1H-imidazole-2-carbaldehyde oxime (20 g, 54.5 mmol) in tetrabutylammonium fluoride (1 M in THF; 200.5 mL, 2.12 mol) was stirred at reflux for 6 hours. The mixture was evaporated in vacuo and the residue was taken up in EtOAc and washed with sat. $Na_2CO_3$. The organic layers were dried ($MgSO_4$), filtered and the solvent evaporated in vacuo. The residue was dissolved in acetic anhydride and stirred at 65° C. for 4 hours. The mixture was diluted with EtOAc and treated with a buffer solution of $K_2HPO_4/KH_2PO_4$. The organic layer was separated, and the aqueous phase was washed with additional EtOAc. The combined organic layers were dried ($MgSO_4$), filtered and the solvent evaporated in vacuo. The crude product was purified by flash column chromatography (silica; MeOH in DCM 0/100 to 5/95). The desired fractions were collected and concentrated in vacuo to yield 4-iodo-1H-imidazole-2-carbonitrile (3 g, 25% yield).

Example A18

Preparation of 1H-imidazole-2-carbonitrile

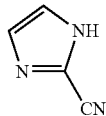

Hydroxylamine hydrochloride (7.96 g, 110 mmol) was added portionwise to a stirred suspension of 2-imidazolecarboxaldehyde (10 g, 100 mmol) in pyridine (27.85 mL) at −5° C. The mixture was stirred at room temperature for 2 hours. Then the mixture was heated at 80° C. and acetic anhydride (18.7 mL, 200 mmol) was added dropwise over 40 minutes to maintain the temperature below 110° C. After the addition, the reaction mixture was stirred at 80° C. for 45 minutes and then cooled to 5° C. and basified to pH 8 with NaOH (25%). The mixture was diluted with EtOAc, the organic layer was separated, dried (Na$_2$SO$_4$), filtered and the solvent evaporated in vacuo. The crude product was diluted with DCM and stirred for 18 hours. The solid was filtered and dried under vacuo to yield 1H-imidazole-2-carbonitrile (7.5 g, 77% yield) that was used in next reaction without further purification.

Example A19

Preparation of 4-formyl-N,N-dimethyl-1H-imidazole-1-sulfonamide

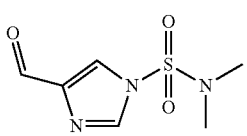

1,4-Diazabicyclo[2.2.2]octane (21 g, 187.33 mmol) and dimethylsulfamoyl chloride (18.4 mL, 171.72 mmol) were added to a stirred suspension of 1H-imidazole-4-carbaldehyde (15 g, 156.11 mmol) in acetonitrile (300 mL) at 0° C. The mixture was allowed to warm to room temperature and stirred for 18 hours. The mixture was concentrated in vacuo and the residue was diluted with water and extracted with EtOAc. The organic layer was separated, dried (MgSO$_4$), filtered and the solvent was evaporated in vacuo. The crude product was purified by flash column chromatography (silica; EtOAc in DCM 0/100 to 60/40). The desired fractions were collected and concentrated in vacuo to yield 4-formyl-N,N-dimethyl-1H-imidazole-1-sulfonamide (27.2 g, 86% yield) as a cream solid.

Example A20

Preparation of 4-(difluoromethyl)-N,N-dimethyl-1H-imidazole-1-sulfonamide

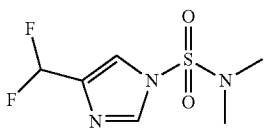

The manifold system (pumps, valves, PFA tubing and reactor coil) of a Vapourtec R2+R4 unit was dried with isopropyl alcohol (2 mL/minutes, 15 min) and anhydrous THF (0.5 mL/minutes, 20 min) A solution of 4-formyl-N,N-dimethyl-1H-imidazole-1-sulfonamide (0.5 g, 2.46 mmol) in DCM was loaded into a sample loop (10 mL) on a Vapourtec R2+R4. A solution of diethylaminosulfur trifluoride (0.65 mL, 4.92 mmol) in DCM was loaded into a second sample loop (10 mL). The two sample loops were switched in-line into streams of DCM, each flowing at 0.110 mL/minutes, and mixed in the reactor at 80° C. The mixture was then matured in the reactor using the 10 mL coil. The output of the coil was then collected directly over CaCO$_3$. The solution was filtered through diatomaceous earth and the solvent was evaporated in vacuo. The crude product was purified by flash column chromatography (silica; DCM). The desired fractions were collected and concentrated in vacuo to yield 4-(difluoromethyl)-N,N-dimethyl-1H-imidazole-1-sulfonamide (0.41 g, 73% yield) as a pale brown solid.

Example A21

Preparation of ethyl 4-(difluoromethyl)-1-(dimethylsulfamoyl)-1H-imidazole-2-carboxylate

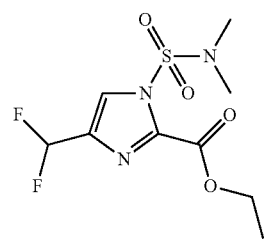 [SMILES: CCOC(=O)c1nc(C(F)F)cn1S(=O)(=O)N(C)C]

Potassium bis(trimethylsilyl)amide (1 M in THF; 7.66 mL, 7.66 mmol) was added dropwise to a stirred solution of 4-(difluoromethyl)-N,N-dimethyl-1H-imidazole-1-sulfonamide (1.5 g, 6.66 mmol) in THF (30 ml) at −78° C. under a nitrogen atmosphere. The mixture was stirred at −78° C. for 1 hour and ethyl cyanoformate (0.76 g, 7.66 mmol) in THF (7 ml) was added. The mixture was stirred at −78° C. for 1 hour and then at room temperature for 2 hours. The mixture was diluted with sat. NH$_4$Cl and extracted with EtOAc. The organic layer was separated, dried (Na$_2$SO$_4$), filtered and the solvent was evaporated in vacuo. The crude product was purified by flash column chromatography (silica; EtOAc in heptane 0/100 to 60/40). The desired fractions were collected and concentrated in vacuo to yield ethyl 4-(difluoromethyl)-1-(dimethylsulfamoyl)-1H-imidazole-2-carboxylate (1.3 g, 66% yield) as a pale yellow oil.

Example A22

Preparation of ethyl 4-(difluoromethyl)-1H-imidazole-2-carboxylate

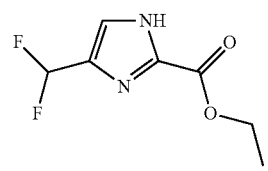

Hydrochloric acid (4 M in dioxane; 35 mL, 140 mmol) was added to ethyl 4-(difluoromethyl)-1-(dimethylsulfamoyl)-1H-imidazole-2-carboxylate (5.55 g, 18.67 mmol). The mixture was stirred at 50° C. for 2 hours. The solvent was evaporated in vacuo. The residue was diluted with NaHCO$_3$ (sat.) and extracted with DCM. The organic layer was separated, dried (Na$_2$SO$_4$), filtered and the solvent was evaporated in vacuo. The crude product was purified by flash column chromatography (silica; EtOAc in DCM 0/100 to 10/90). The desired fractions were collected and concentrated in vacuo to yield ethyl 4-(difluoromethyl)-1H-imidazole-2-carboxylate (2.98 g, 84% yield) as a white solid.

Example A23

Preparation of 1-(5-bromo-2-fluorophenyl)-2,2-difluoroethanone

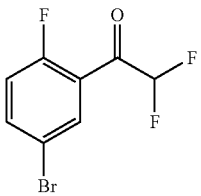 [SMILES: O=C(c1cc(Br)ccc1F)C(F)F]

n-Butyllithium (2.5 M in hexane; 20.03 mL, 50.07 mmol) was added to a stirred solution of diisopropylamine (7.02 mL, 50.07 mmol) in THF (125.4 mL) at −70° C. under a nitrogen atmosphere. The mixture was stirred at −70° C. for 30 minutes and then 4-bromofluorobenzene (5 mL, 45.51 mmol) was added dropwise. The reaction mixture was stirred for 30 minutes at −70° C. before ethyl difluoroacetate (5.74 mL, 54.62 mmol) was added. The mixture was stirred at −70° C. for 1 hour and then diluted with NH$_4$Cl (sat.) and extracted with diethyl ether. The organic layer was separated, dried (MgSO$_4$), filtered and the solvent was evaporated in vacuo. The crude product was purified by flash column chromatography (silica; DCM in heptane 0/100 to 100/0). The desired fractions were collected and concentrated in vacuo to yield 1-(5-bromo-2-fluorophenyl)-2,2-difluoroethanone (9.3 g, 81% yield) as a pale yellow oil that solidified upon standing.

Example A24

Preparation of tert-butyl [(1Z)-1-(5-bromo-2-fluorophenyl)-2,2-difluoroethylidene]carbamate

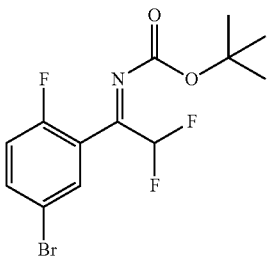 [SMILES: CC(C)(C)OC(=O)/N=C(/c1cc(Br)ccc1F)C(F)F]

N-boc-imino-(triphenyl)phosphorane (15.26 g, 40.43 mmol) was added to a stirred solution of 1-(5-bromo-2-fluorophenyl)-2,2-difluoroethanone (9.3 g, 36.76 mmol) in toluene (93 mL). The mixture was stirred at 90° C. for 18 hours. The solvent was evaporated in vacuo and the residue was taken up in heptane. The solid was filtered off and the filtrate was evaporated in vacuo. The crude product was purified by flash column chromatography (silica; EtOAc in heptane 0/100 to 5/95). The desired fractions were collected and concentrated in vacuo to yield tert-butyl [(1Z)-1-(5-bromo-2-fluorophenyl)-2,2-difluoroethylidene]carbamate (8.7 g, 67% yield) as a pale yellow oil.

Example A25

Preparation of rac-tert-butyl [1-(5-bromo-2-fluorophenyl)-1-(difluoromethyl)prop-2-en-1-yl]carbamate

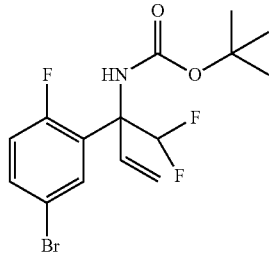 [SMILES: C=CC(NC(=O)OC(C)(C)C)(c1cc(Br)ccc1F)C(F)F]

Vinylmagnesium bromide (1 M in THF; 4 mL, 4 mmol) was added to a stirred solution of tert-butyl [(1Z)-1-(5-bromo-2-fluorophenyl)-2,2-difluoroethylidene]carbamate (0.94 g, 2.67 mmol) in THF (8.9 mL) at −78° C. under a nitrogen atmosphere. The mixture was stirred at −78° C. for 30 minutes and at room temperature for 18 hours. The mixture was diluted with sat. NH$_4$Cl and extracted with DCM. The organic layer was separated, dried (MgSO$_4$), filtered and the solvent was evaporated in vacuo. The crude product was purified by flash column chromatography (silica; EtOAc in DCM 0/100 to 100/0). The desired fractions were collected and concentrated in vacuo to yield rac-tert-butyl [1-(5-bromo-2-fluorophenyl)-1-(difluoromethyl)prop-2-en-1-yl] carbamate (1 g, 99% yield) as a colourless oil.

Example A26

Preparation of rac-tert-butyl [1-(5-bromo-2-fluorophenyl)-2,2-difluoro-1-(hydroxymethyl)ethyl]carbamate

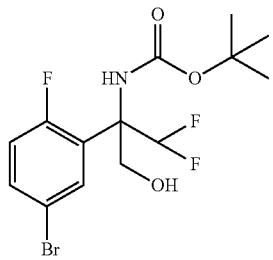 [SMILES: CC(C)(C)OC(=O)NC(CO)(c1cc(Br)ccc1F)C(F)F]

To a solution of rac-tert-butyl [1-(5-bromo-2-fluorophenyl)-1-(difluoromethyl)prop-2-en-1-yl]carbamate (3.0 g, 7.9 mmol) in a mixture of DCM (50 mL) and MeOH (112 mL) at −78° C., ozone was introduced while the blue colour persisted (30 minutes). The excess of ozone was removed by bubbling through oxygen gas for 10 minutes. Then, sodium borohydride (0.89 g, 23.7 mmol) was added and the mixture was allowed to reach 0° C. After stirring 30 minutes, the mixture was poured onto HCl (1 N) and extracted with diethyl ether. The organic layer was separated, washed with water and brine, dried (Na₂SO₄), filtered and the solvent was evaporated in vacuo to yield rac-tert-butyl [1-(5-bromo-2-fluorophenyl)-2,2-difluoro-1-(hydroxymethyl)ethyl]carbamate (2.99 g, 98% yield) as a white solid.

Example A27

Preparation of (R)-tert-butyl [1-(5-amino-2-fluorophenyl)-2-hydroxy-1-methylethyl]carbamate

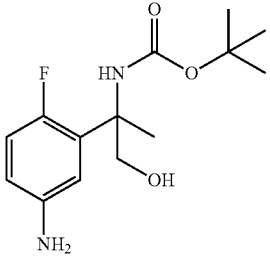 [SMILES: CC(C)(C)OC(=O)NC(C)(CO)c1cc(N)ccc1F]

Dimethyl sulfoxide (279.5 mL) was added to a mixture of (R) tert-butyl [1-(5-bromo-2-fluorophenyl)-2-hydroxy-1-methylethyl]carbamate (6.8 g, 19.5 mmol), sodium azide (3.17 g, 48.8 mmol), copper(I) iodide (4.65 g, 24.4 mmol) and Na₂CO₃ (4.14 g, 39.1 mmol). The mixture was degassed with nitrogen for a few minutes and then N,N'-dimethylethylenediamine (3.68 mL, 34.2 mmol) was added and the mixture was stirred at 90° C. for 16 hours. After cooling to room temperature, the mixture was filtered through diatomaceous earth and washed with water. The filtrate was diluted with EtOAc and water and carefully acidified with 1M HCl. The organic layer was separated and the aqueous phase was extracted with additional EtOAc. The aqueous phase was basified with NH₃ in water and then washed with EtOAc. The combined organic layers were dried (MgSO₄), filtered and the solvent was evaporated in vacuo. The crude product was purified by flash column chromatography (silica; 7 M solution of ammonia in MeOH in DCM 0/100 to 5/95). The desired fractions were collected and concentrated in vacuo to yield (R)-tert-butyl [1-(5-amino-2-fluorophenyl)-2-hydroxy-1-methylethyl]carbamate (2.7 g, 49% yield).

Example A28

Preparation of (R)-ethyl (3-{1-[(tert-butoxycarbonyl)amino]-2-hydroxy-1-methylethyl}-4-fluorophenyl)carbamate

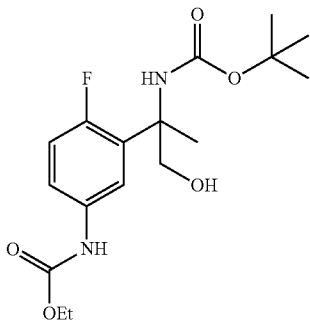 [SMILES: CCOC(=O)Nc1ccc(F)c(C(C)(CO)NC(=O)OC(C)(C)C)c1]

Ethyl chloroformate (1 mL, 10.5 mmol) was added to a mixture of (R)-tert-butyl [1-(5-amino-2-fluorophenyl)-2-hydroxy-1-methylethyl]carbamate (2.7 g, 9.5 mmol) in sat. NaHCO₃ (60 mL) and THF (50 mL). The mixture was stirred at room temperature for 4 hours. Then, the mixture was diluted with EtOAc, the organic layer was separated, dried (Na₂SO₄), filtered and the solvent was evaporated in vacuo to yield (R)-ethyl (3-{1-[(tert-butoxycarbonyl)amino]-2-hydroxy-1-methylethyl}-4-fluorophenyl)carbamate (3.1 g, 92% yield). The product was used in the next reaction without further purification.

Example A29

Preparation of rac-[3-(tert-butyloxycarbonyl)-4-(3-bromo-phenyl)-4-methyl-[1,1,3]oxathiazolidine-2-oxide

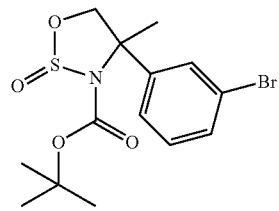 [SMILES: CC(C)(C)OC(=O)N1S(=O)OCC1(C)c1cccc(Br)c1]

A solution of rac-[1-(3-bromo-phenyl)-2-hydroxy-1-methyl-ethyl]-carbamic acid tert-butyl ester (7.2 g, 21.8 mmol) in dry acetonitrile (40 mL) was added dropwise to a stirred solution of thionyl chloride (3.98 mL, 54.51 mmol) in dry acetonitrile ((114 mL) cooled to −40° C. under a nitrogen atmosphere. The reaction mixture was stirred for 30 minutes at −40° C. before pyridine (8.78 mL, 109.02 mmol) was added. The reaction was allowed to warm to room temperature and was stirred for 64 hours. The solvent was evaporated in vacuo. EtOAc was added to the residue. The solid was filtered off and the filtrate concentrated in vacuo. The residue was treated with diethyl ether. The solids were filtered and the filtrate concentrated in vacuo to yield rac-[3-(tert-butyloxycarbonyl)-4-(3-bromo-phenyl)-4-methyl-[1,1,3]oxathiazolidine-2-oxide (7.09 g, 86% yield) as an oil that was used in the next reaction without further purification.

Example A30

Preparation of rac-[3-(tert-butyloxycarbonyl)-4-(3-bromo-phenyl)-4-methyl-[1,1,3]oxathiazolidine-2,2-dioxide

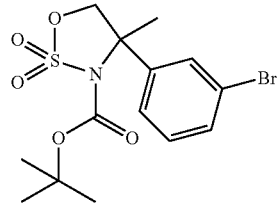 [SMILES: CC(C)(C)OC(=O)N1C(C)(c2cccc(Br)c2)COS1(=O)=O]

Ruthenium (III) chloride (39 mg, 0.19 mmol) was added to solution of rac-[3-(tert-butyloxycarbonyl)-4-(3-bromophenyl)-4-methyl-[1,1,3]oxathiazolidine-2-oxide (7 g, 18.6 mmol) in acetonitrile/water (1:1) (200 mL) at 0° C., followed by the addition of sodium periodate (5.97 g, 27.91 mmol). The reaction was allowed to warm to room temperature and stirred for 2 hours. The mixture was filtered through diatomaceous earth and washed with EtOAc (50 mL). Water (50 mL) and EtOAc (100 mL) was added to the filtrate. The organic layer was separated, dried (MgSO₄), filtered and the solvent was evaporated in vacuo. The product was purified by flash column chromatography (silica gel; DCM). The desired fractions were collected and concentrated in vacuo to yield rac-[3-(tert-butyloxycarbonyl)-4-(3-bromo-phenyl)-4-methyl-[1,1,3]oxathiazolidine-2,2-dioxide (6.66 g, 91% yield) as a white solid.

The following intermediates were prepared according to similar synthetic procedures described in examples A29-A30:

Example A31

Preparation of (R)-tert-butyl-4-(5-bromo-2-fluorophenyl)-4-methyl-1,2,3-oxathiazolidine-3-carboxylate 2,2-dioxide

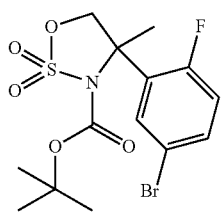 [SMILES: CC(C)(C)OC(=O)N1C(C)(c2cc(Br)ccc2F)COS1(=O)=O]

From (R)-tert-butyl [1-(5-bromo-2-fluorophenyl)-2-hydroxy-1-methylethyl]carbamate.

Example A32

Preparation of rac-tert-butyl 4-(5-bromo-2-fluorophenyl)-4-(difluoromethyl)-1,2,3-oxathiazolidine-3-carboxylate 2,2-dioxide

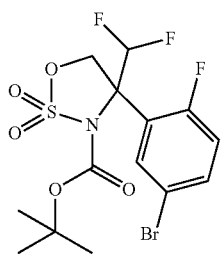 [SMILES: CC(C)(C)OC(=O)N1C(c2cc(Br)ccc2F)(C(F)F)COS1(=O)=O]

From rac-tert-butyl [1-(5-bromo-2-fluorophenyl)-2,2-difluoro-1-(hydroxymethyl)-ethyl]carbamate.

Example A33

Preparation of (R)-tert-butyl-4-{5-[(ethoxycarbonyl)amino]-2-fluorophenyl}-4-methyl-1,2,3-oxathiazolidine-3-carboxylate 2,2-dioxide

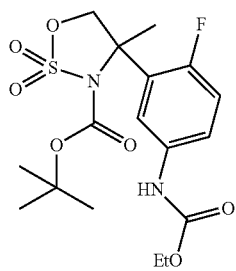 [SMILES: CCOC(=O)Nc1ccc(F)c(C2(C)COS(=O)(=O)N2C(=O)OC(C)(C)C)c1]

From (R)-ethyl-(3-{1-[(tert-butoxycarbonyl)amino]-2-hydroxy-1-methylethyl}-4-fluorophenyl)carbamate.

Example A34

Preparation of rac-1-[1-(3-bromo-phenyl)1-tert.butoxycarbonylamino-ethyl]-1H-imidazole-2-carboxylic acid ethyl ester

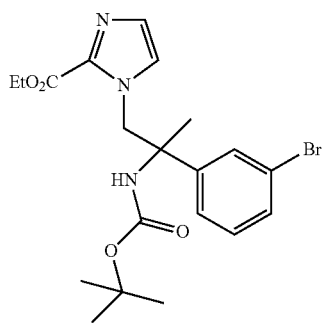 [SMILES: CCOC(=O)c1nccn1CC(C)(NC(=O)OC(C)(C)C)c1cccc(Br)c1]

Sodium hydride (60% in mineral oil) (199 mg, 4.97 mmol) was added to a solution of ethyl imidazole-2-carboxylate (697 mg, 4.97 mmol) in DMF (33 mL) at room temperature and the reaction mixture was stirred at room temperature for 30 min. rac-[3-(tert-butyloxycarbonyl)-4-(3-bromo-phenyl)-4-methyl-[1,1,3]oxathiazolidine-2,2-dioxide (1.95 g, 4.97 mmol) was added and the reaction mixture was heated at 100° C. for 64 hours. Water was added and the product extracted with DCM. The organic layer was separated, dried, filtered and the solvent was evaporated in vacuo. The crude product was purified by flash column chromatography (silica: MeOH in DCM 0/100 to 5/95). The desired fractions were collected and concentrated in vacuo to yield rac-1-[1-(3-bromo-phenyl)1-tert.butoxycarbonylamino-ethyl]-1H-imidazole-2-carboxylic acid ethyl ester (1.19 g, 53% yield) as a colourless oil.

The following intermediate was prepared according to a similar synthetic procedure described in example A34:

Example A35

Preparation of (R)-tertbutyl {1-(5-bromo-2-fluorophenyl)-2-[2-cyano-4-[(trifluoromethyl)-1H-imidazol-1-yl]-1-methylethyl}carbamate

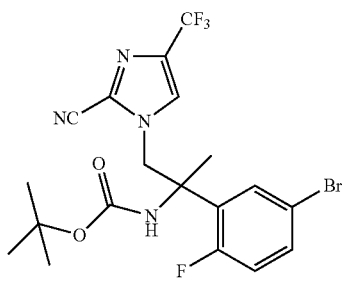

From (R)-tert-butyl-4-(5-bromo-2-fluorophenyl)-4-methyl-1,2,3-oxathiazolidine-3-carboxylate 2,2-dioxide and 4-(trifluoromethyl)-1H-imidazole-2-carbonitrile.

Example A36

Preparation of (R)-tert-butyl [1-(5-bromo-2-fluorophenyl)-2-(2-cyano-1H-imidazol-1-yl)-1-methylethyl]carbamate

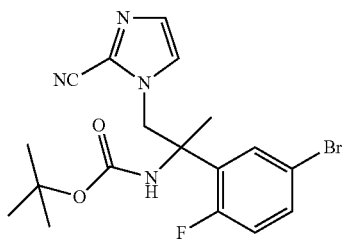 [SMILES: CC(C)(C)OC(=O)NC(C)(Cn1ccnc1C#N)c1cc(Br)ccc1F]

1,8-Diazabicyclo[5.4.0]undec-7-ene (7.28 mL, 48.75 mmol) was added to a stirred solution of (R)-tert-butyl-4-(5-bromo-2-fluorophenyl)-4-methyl-1,2,3-oxathiazolidine-3-carboxylate 2,2-dioxide (10 g, 24.4 mmol) and 1H-imidazole-2-carbonitrile (2.61 g, 28.03 mmol) in acetonitrile (80 mL). The mixture was stirred at 90° C. for 18 hours and then diluted with HCl (1 M) and extracted with DCM. The organic layer was separated, dried (Na$_2$SO$_4$), filtered and the solvent was evaporated in vacuo. The crude product was purified by flash column chromatography (silica; EtOAc in DCM 0/100 to 10/90). The desired fractions were collected and concentrated in vacuo to yield (R)-tert-butyl [1-(5-bromo-2-fluorophenyl)-2-(2-cyano-1H-imidazol-1-yl)-1-methylethyl]carbamate (10 g, 97% yield) as a sticky solid.

Example A37

Preparation of (R)-ethyl 1-{2-(5-bromo-2-fluorophenyl)-2-[(tert-butoxycarbonyl)amino]propyl}-4-(difluoromethyl)-1H-imidazole-2-carboxylate

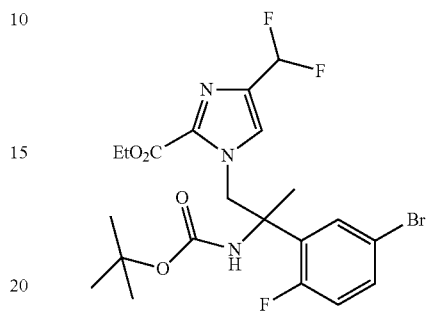

Ethyl 4-(difluoromethyl)-1H-imidazole-2-carboxylate (0.5 g, 2.63 mmol) was added to a stirred solution of tert-butyl (R)-4-(5-bromo-2-fluorophenyl)-4-methyl-1,2,3-oxathiazolidine-3-carboxylate 2,2-dioxide (1.03 g, 2.5 mmol) and K$_2$CO$_3$ (0.36 g, 2.63 mmol) in DMF (10.5 mL) at room temperature. The mixture was stirred at 100° C. for 2 hours and then concentrated in vacuo. The residue was diluted with citric acid (sat.) and EtOAc. The mixture was stirred at room temperature for 16 hours. The organic layer was separated, dried (Na$_2$SO$_4$), filtered and the solvent was evaporated in vacuo. The crude product was purified by flash column chromatography (silica; DCM). The desired fractions were collected and concentrated in vacuo to yield ethyl 1-{(R)-2-(5-bromo-2-fluorophenyl)-2-[(tert-butoxycarbonyl)amino]propyl}-4-(difluoromethyl)-1H-imidazole-2-carboxylate (0.66 g, 51% yield) as a colourless oil.

The following intermediates were prepared according to a similar synthetic procedure described in example A37:

Example A38

Preparation of (R)-ethyl {3-[1-[(tert-butoxycarbonyl)amino]-2-(4-chloro-2-cyano-1H-imidazol-1-yl)-1-methylethyl]-4-fluorophenyl}carbamate

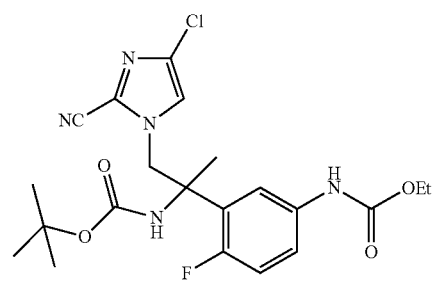 [SMILES: CCOC(=O)Nc1ccc(F)c(C(C)(Cn2cc(Cl)nc2C#N)NC(=O)OC(C)(C)C)c1]

From (R)-tert-butyl-4-{5-[(ethoxycarbonyl)amino]-2-fluorophenyl}-4-methyl-1,2,3-oxathiazolidine-3-carboxylate 2,2-dioxide and 4-chloro-1H-imidazole-2-carbonitrile.

Example A39

Preparation of (R)-ethyl {3-[1-[(tert-butoxycarbonyl)amino]-2-(4-bromo-2-cyano-1H-imidazol-1-yl)-1-methylethyl]-4-fluorophenyl}carbamate

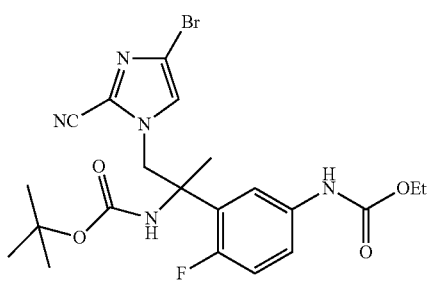 [SMILES: CCOC(=O)Nc1ccc(F)c(C(C)(Cn2cc(Br)nc2C#N)NC(=O)OC(C)(C)C)c1]

From (R)-tert-butyl-4-{5-[(ethoxycarbonyl)amino]-2-fluorophenyl}-4-methyl-1,2,3-oxathiazolidine-3-carboxylate 2,2-dioxide and 4-bromo-1H-imidazole-2-carbonitrile.

Example A40

Preparation of (R)-ethyl {3-[1-[(tert-butoxycarbonyl)amino]-2-(2-cyano-4-iodo-1H-imidazol-1-yl)-1-methylethyl]-4-fluorophenyl}carbamate

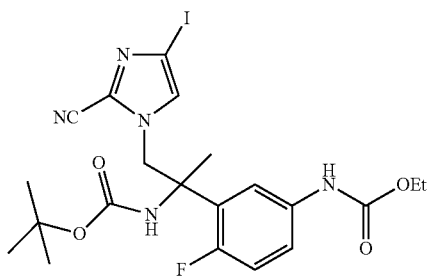 [SMILES: CCOC(=O)Nc1ccc(F)c(C(C)(Cn2cc(I)nc2C#N)NC(=O)OC(C)(C)C)c1]

From (R)-tert-butyl 4-{5-[(ethoxycarbonyl)amino]-2-fluorophenyl}-4-methyl-1,2,3-oxathiazolidine-3-carboxylate 2,2-dioxide and 4-iodo-1H-imidazole-2-carbonitrile.

Example A41

Preparation of rac-1-[2-amino-2-(3-bromo-phenyl)-propyl]-1H-imidazole-2-carboxylic acid ethyl ester

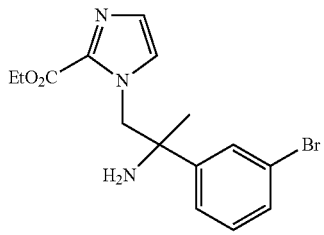

Trifluoroacetic acid (5.9 mL) was added to a solution of rac-1-[1-(3-bromo-phenyl)1-tert.butoxycarbonylamino-ethyl]-1H-imidazole-2-carboxylic acid ethyl ester (1.18 g, 2.61 mmol) in DCM (59 mL) and the reaction mixture was stirred at room temperature overnight. The reaction was concentrated in vacuo to yield rac-1-[2-amino-2-(3-bromo-phenyl)-propyl]-1H-imidazole-2-carboxylic acid ethyl ester (1.49 g, 92% yield) as an oil. The product was used in the following step without any further purification.

Example A42

Preparation of ethyl 1-[(R)-2-amino-2-(5-bromo-2-fluorophenyl)propyl]-4-(difluoromethyl)-1H-imidazole-2-carboxylate

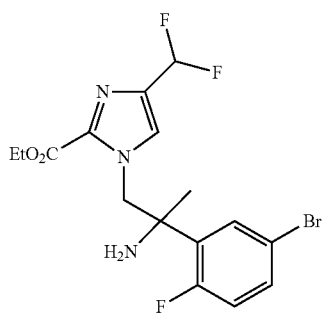 [SMILES: CCOC(=O)c1nc(C(F)F)cn1CC(C)(N)c1cc(Br)ccc1F]

Hydrochloric acid (4 M in dioxane; 3.4 mL, 13.5 mmol) was added to ethyl 1-{(R)-2-(5-bromo-2-fluorophenyl)-2-[(tert-butoxycarbonyl)amino]propyl}-4-(difluoromethyl)-1H-imidazole-2-carboxylate (0.62 g, 1.19 mmol). The mixture was stirred at room temperature for 90 minutes. The solvent was evaporated in vacuo. The residue was diluted with sat. NaHCO$_3$ and extracted with DCM. The organic layer was separated, dried (MgSO$_4$), filtered and the solvent was evaporated in vacuo to yield ethyl 1-[(R)-2-amino-2-(5-bromo-2-fluorophenyl)propyl]-4-(difluoromethyl)-1H-imidazole-2-carboxylate (0.5 g, 100% yield) that was used in the next step without further purification.

Example A43

Preparation of rac-ethyl 1-[2-amino-2-(5-bromo-2-fluorophenyl)-3,3-difluoropropyl]-1H-imidazole-2-carboxylate

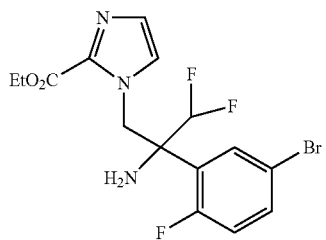 [SMILES: CCOC(=O)c1nccn1CC(N)(c1cc(Br)ccc1F)C(F)F]

1,8-Diazabicyclo[5.4.0]undec-7-ene (3.35 mL, 22.4 mmol) was added to a stirred solution of rac-tert-butyl 4-(5-bromo-2-fluorophenyl)-4-(difluoromethyl)-1,2,3-oxathiazolidine-3-carboxylate 2,2-dioxide (5 g, 11.2 mmol) and ethyl imidazole-2-carboxylate (2.36 g, 16.8 mmol) in toluene (50 mL). The mixture was stirred at 60° C. for 18 hours and then the solvent was concentrated in vacuo. The residue was dissolved in THF (50 mL), treated with HCl (1

N) and stirred for 18 hours at room temperature. The mixture was diluted with EtOAc, the organic layer was separated, dried (Na$_2$SO$_4$), filtered and the solvent was evaporated in vacuo to yield a residue that was dissolved in HCl 4 M in dioxane (28 mL) and stirred at room temperature for 1 hour. The mixture was evaporated in vacuo and the residue was suspended in DCM and washed with sat. NaHCO$_3$. The organic layer was separated, dried (Na$_2$SO$_4$), filtered and the solvent was evaporated in vacuo to yield rac-ethyl 1-[2-amino-2-(5-bromo-2-fluorophenyl)-3,3-difluoropropyl]-1H-imidazole-2-carboxylate (3.95 g, 87% yield) as a white solid. The product was used in the next reaction without further purification.

Example A44

Preparation of (R)-tert-butyl [1-(5-bromo-2-fluorophenyl)-2-(4-chloro-2-cyano-1H-imidazol-1-yl)-1-methylethyl]carbamate

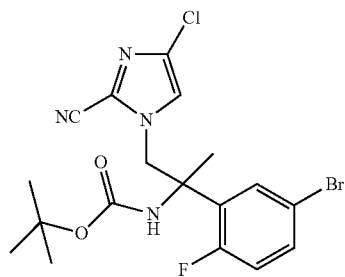 [SMILES: CC(C)(C)OC(=O)NC(C)(Cn1cc(Cl)nc1C#N)c1cc(Br)ccc1F]

1,8-Diazabicyclo[5.4.0]undec-7-ene (10.3 mL, 68.8 mmol) was added to a stirred solution of (R)-tert-butyl 4-(5-bromo-2-fluorophenyl)-4-methyl-1,2,3-oxathiazolidine-3-carboxylate 2,2-dioxide (28.24 g, 34.41 mmol) and 4-chloro-1H-imidazole-2-carbonitrile (7.9 g, 61.94 mmol) in acetonitrile (203 mL). The mixture was stirred at 100° C. for 2 hours and then diluted with DCM and washed with HCl (1 N). The organic layer was separated, dried (MgSO$_4$), filtered and the solvent was evaporated in vacuo. The crude product was purified by flash column chromatography (silica; EtOAc in DCM 0/100 to 10/90). The desired fractions were collected and evaporated in vacuo to yield (R)-tert-butyl [1-(5-bromo-2-fluorophenyl)-2-(4-chloro-2-cyano-1H-imidazol-1-yl)-1-methylethyl]carbamate (15.5 g, 98% yield) as a white solid.

Example A45

Preparation of (R)-1-[2-amino-2-(3-bromo-phenyl)-propyl]-1H-imidazole-2-carboxylic acid ethyl ester

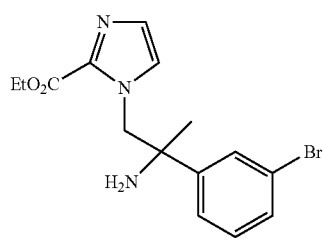 [SMILES: CCOC(=O)c1nccn1CC(C)(N)c1cccc(Br)c1]

Cesium carbonate (4.98 g, 15.3 mmol) was added to a mixture of ethyl imidazole-2-carboxylate (1.39 g, 9.94 mmol) and (R)-[3-(tert-butyloxycarbonyl)-4-(3-bromo-phenyl)-4-methyl-[1,1,3]oxathiazolidine-2,2-dioxide (3 g, 7.65 mmol) in dry acetonitrile (36 mL). The mixture was stirred at 130° C. for 45 minutes under microwave irradiation. Then NH$_4$Cl (sat.) was added and the product extracted with DCM. The organic layer was separated, dried (MgSO$_4$), filtered and the solvent was evaporated in vacuo. Then HCl (4M in dioxane) was added and the mixture was stirred at room temperature for 1 hour. The solvent was concentrated in vacuo and the residue was suspended in DCM and washed with a saturated solution of NaHCO$_3$. The organic layer was separated, dried (MgSO$_4$), filtered and the solvents evaporated in vacuo. The crude product was purified by flash column chromatography (silica: EtOAc). The desired fractions were collected and concentrated in vacuo to yield (R)-1-[2-amino-2-(3-bromo-phenyl)-propyl]-1H-imidazole-2-carboxylic acid ethyl ester (1.46 g, 54% yield) as a white solid.

The following intermediate was prepared according to a similar synthetic procedure described in example A45:

Example A46

Preparation of (R)-ethyl 1-[2-amino-2-(5-bromo-2-fluorophenyl)propyl]-1H-imidazole-2-carboxylate

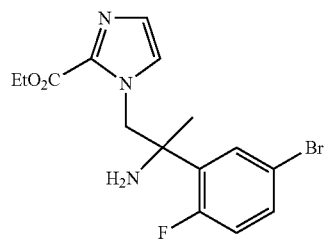 [SMILES: CCOC(=O)c1nccn1CC(C)(N)c1cc(Br)ccc1F]

From (R)-tert-butyl-4-(5-bromo-2-fluorophenyl)-4-methyl-1,2,3-oxathiazolidine-3-carboxylate 2,2-dioxide.

Example A47

Preparation of rac-6-(3-bromo-phenyl)-6-methyl-6,7-dihydro-5H-imidazo[1,2-a]pyrazin-8-one

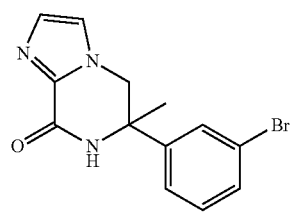 [SMILES: CC1(c2cccc(Br)c2)Cn2ccnc2C(=O)N1]

A solution of rac-1-[2-amino-2-(3-bromo-phenyl)-propyl]-1H-imidazole-2-carboxylic acid ethyl ester (1.4 g, 3 mmol) in ethanol (10 mL) was heated at 90° C. for 24 hours. The reaction mixture was concentrated in vacuo, treated with sat. NaHCO$_3$ and the product was extracted with DCM. The organic layer was separated, dried (MgSO$_4$), filtered and the solvent was evaporated in vacuo to yield rac-6-(3-bromo-phenyl)-6-methyl-6,7-dihydro-5H-imidazo[1,2-a]pyrazin-8-one (0.6 g, 65% yield) as a white solid.

The following intermediate was prepared according to a similar synthetic procedure described in example A47:

Example A48

Preparation of (R)-6-(5-bromo-2-fluorophenyl)-6-methyl-6,7-dihydroimidazo[1,2-a]-pyrazin-8(5H)-one

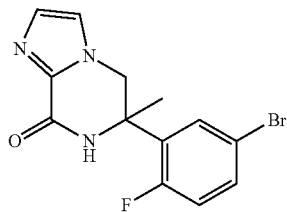

From (R)-ethyl 1-[2-amino-2-(5-bromo-2-fluorophenyl)propyl]-1H-imidazole-2-carboxylate.

Example A49

Preparation of rac-6-(5-bromo-2-fluorophenyl)-6-(difluoromethyl)-6,7-dihydroimidazo[1,2-a]pyrazin-8(5H)-one

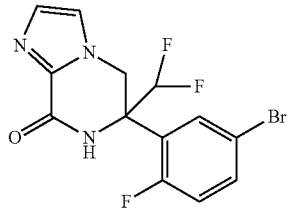

Trimethylaluminium 2 M in toluene (10.6 mL, 21.1 mmol) was added to a stirred solution of rac-ethyl 1-[2-amino-2-(5-bromo-2-fluorophenyl)-3,3-difluoropropyl]-1H-imidazole-2-carboxylate (3.9 g, 9.6 mmol) in THF (39 mL) at 0° C. The mixture was stirred at 120° C. for 30 minutes under microwave irradiation. The mixture was diluted with Na₂CO₃ (sat.) at 0° C. and extracted with DCM. The organic layer was separated, dried (MgSO₄), filtered and the solvent was evaporated in vacuo. The crude product was purified by flash column chromatography (silica; EtOAc). The desired fractions were collected and concentrated in vacuo to yield rac-6-(5-bromo-2-fluorophenyl)-6-(difluoromethyl)-6,7-dihydroimidazo[1,2-a]pyrazin-8(5H)-one (3 g, 87% yield) as a white solid.

Example A50

Preparation of (R)-6-(3-bromo-phenyl)-6-methyl-6,7-dihydro-5H-imidazo[1,2-a]-pyrazin-8-one

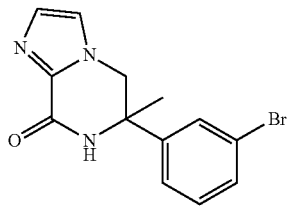 [SMILES: CC1(c2cccc(Br)c2)Cn2ccnc2C(=O)N1]

Sodium methoxide (25% in MeOH) (1.9 mL, 8.29 mmol) was added to a solution of (R)-1-[2-amino-2-(3-bromo-phenyl)-propyl]-1H-imidazole-2-carboxylic acid ethyl ester (1.46 g, 4.15 mmol) in MeOH (5 mL) and the reaction mixture was heated at 55° C. for 18 h. The reaction was concentrated in vacuo, treated with sat. NH₄Cl and the product was extracted with DCM. The organic layer was separated, dried (MgSO₄), filtered and the solvent was evaporated in vacuo to yield (R)-6-(3-bromo-phenyl)-6-methyl-6,7-dihydro-5H-imidazo[1,2-a]pyrazin-8-one (1.2 g, 95% yield) as a white solid.

Example A51

Preparation of (R)-6-(5-bromo-2-fluorophenyl)-2-(difluoromethyl)-6-methyl-6,7-dihydroimidazo[1,2-a]pyrazin-8(5H)-one

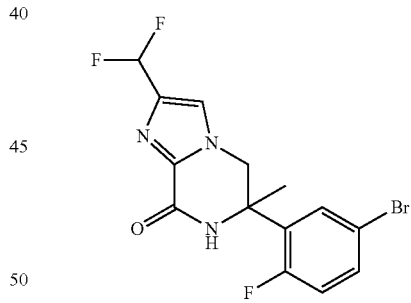

K₂CO₃ (1.32 g, 13.42 mmol) was added to a stirred solution of ethyl 1-[(R)-2-amino-2-(5-bromo-2-fluorophenyl)propyl]-4-(difluoromethyl)-1H-imidazole-2-carboxylate (3.6 g, 7.45 mmol) in EtOH (51.1 mL) and the reaction mixture was heated at 80° C. for 4 hours. The mixture was concentrated in vacuo, treated with NH₄Cl (sat.) and the product was extracted with EtOAc. The organic layer was separated, dried (Na₂SO₄), filtered and the solvent was evaporated in vacuo to yield (R)-6-(5-bromo-2-fluorophenyl)-2-(difluoromethyl)-6-methyl-6,7-dihydroimidazo[1,2-a]pyrazin-8(5H)-one (2.89 g, 100% yield) as a white foam. The product was used in next reaction without further purification.

Example A52

Preparation of rac-6-(3-bromo-phenyl)-6-methyl-6,7-dihydro-5H-imidazo[1,2-a]-pyrazine-8-thione

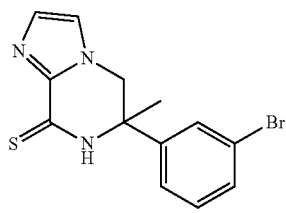 [SMILES: CC1(c2cccc(Br)c2)Cn2ccnc2C(=S)N1]

Phosphoruspentasulfide (0.65 g, 2.94 mmol) was added to a solution of rac-6-(3-bromo-phenyl)-6-methyl-6,7-dihydro-5H-imidazo[1,2-a]pyrazin-8-one (0.6 g, 1.96 mmol) in pyridine (7 mL) and the mixture was heated at 95° C. for 18 hours. The solvent was evaporated in vacuo and the residue was purified by flash column chromatography (silica gel; EtOAc in DCM 0/100 to 100/0). The desired fractions were collected and concentrated in vacuo to yield rac-6-(3-bromo-phenyl)-6-methyl-6,7-dihydro-5H-imidazo[1,2-a]pyrazine-8-thione (0.49 g, 78% yield) as a yellow solid.

The following intermediates were prepared according to a similar synthetic procedure described in example A52:

Example A53

Preparation of (R)-6-(5-bromo-2-fluorophenyl)-6-methyl-6,7-dihydroimidazo[1,2-a]-pyrazine-8(5H)-thione

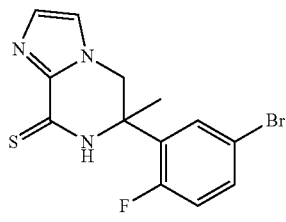 [SMILES: CC1(c2cc(Br)ccc2F)Cn2ccnc2C(=S)N1]

From (R)-6-(5-bromo-2-fluorophenyl)-6-methyl-6,7-dihydroimidazo[1,2-a]pyrazin-8(5H)-one.

Example A54

Preparation of rac-6-(5-bromo-2-fluorophenyl)-6-(difluoromethyl)-6,7-dihydroimidazo[1,2-a]pyrazine-8(5H)-thione

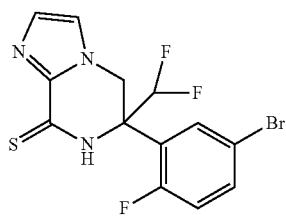 [SMILES: Fc1ccc(Br)cc1C1(C(F)F)Cn2ccnc2C(=S)N1]

From rac-6-(5-bromo-2-fluorophenyl)-6-(difluoromethyl)-6,7-dihydroimidazo[1,2-a]-pyrazin-8(5H)-one.

Example A55

Preparation of (R)-6-(5-bromo-2-fluorophenyl)-2-(difluoromethyl)-6-methyl-6,7-dihydroimidazo[1,2-a]pyrazine-8(5H)-thione

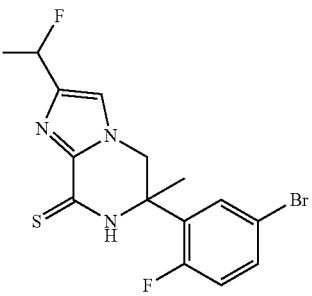

From (R)-6-(5-bromo-2-fluorophenyl)-2-(difluoromethyl)-6-methyl-6,7-dihydroimidazo[1,2-a]pyrazin-8(5H)-one.

Example A56

Preparation of rac-6-(3-bromo-phenyl)-6-methyl-5,6-dihydro-imidazo[1,2-a]pyrazin-8-ylamine

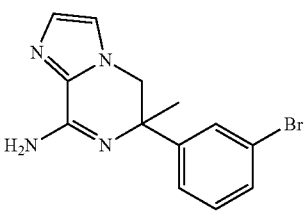

An 32% aqueous ammonia solution (3.2 mL, 54.7 mmol) was added to a stirred mixture of (rac-6-(3-bromo-phenyl)-6-methyl-6,7-dihydro-5H-imidazo[1,2-a]pyrazine-8-thione (049 g, 1.52 mmol) in a 7 N solution of ammonia in MeOH (3.3 mL, 22.8 mmol) in a sealed tube. The mixture was stirred at 60° C. for 96 hours. After cooling to room temperature the mixture was diluted with water and $Na_2CO_3$ (aqueous sat.) and extracted with DCM. The organic layer was separated, dried ($Na_2SO_4$), filtered and the solvent was evaporated in vacuo. The crude product was purified by flash column chromatography (silica gel; 7 M solution of ammonia in MeOH in DCM 0/100 to 2/98 to 3/97 to 10/90). The desired fractions were collected and concentrated in vacuo to yield rac-6-(3-bromo-phenyl)-6-methyl-5,6-dihydro-imidazo[1,2-a]pyrazin-8-ylamine (0.44 g, 95% yield) as a yellow solid.

The following intermediate was prepared according to a similar synthetic procedure described in example A56:

Example A57

Preparation of (R)-6-(5-bromo-2-fluorophenyl)-6-methyl-5,6-dihydroimidazo[1,2-a]-pyrazin-8-amine

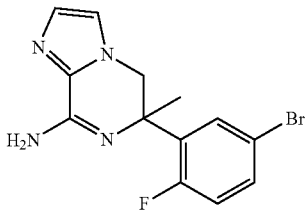

From (R)-6-(5-bromo-2-fluorophenyl)-6-methyl-6,7-dihydroimidazo[1,2-a]pyrazine-8(5H)-thione.

Example A58

Preparation of rac-6-(5-bromo-2-fluorophenyl)-6-(difluoromethyl)-5,6-dihydroimidazo[1,2-a]pyrazin-8-amine

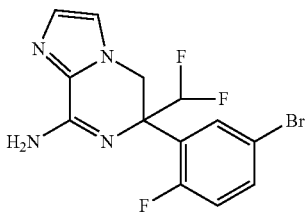 [SMILES: NC1=NC(c2cc(Br)ccc2F)(C(F)F)Cn2ccnc21]

Ammonium chloride (0.91 g, 17 mmol) was added to a stirred solution of rac-6-(5-bromo-2-fluorophenyl)-6-(difluoromethyl)-6,7-dihydroimidazo[1,2-a]pyrazine-8(5H)-thione (1.6 g, 4.25 mmol) in a 7 N solution of ammonia in MeOH (32 mL, 63.8 mmol) in a sealed tube. The mixture was stirred at 80° C. for 18 hours. The mixture was concentrated in vacuo and the residue was suspended in DCM and washed with water. The organic layer was separated, dried (MgSO$_4$), filtered and the solvent was evaporated in vacuo. The crude product was purified by flash column chromatography (silica; 7 M solution of ammonia in MeOH in DCM 0/100 to 2/98). The desired fractions were collected and concentrated in vacuo to yield rac-6-(5-bromo-2-fluorophenyl)-6-(difluoromethyl)-5,6-dihydroimidazo[1,2-a]pyrazin-8-amine (1.5 g, 98% yield) as a white solid.

The following intermediate was prepared according to a similar synthetic procedure described in example A58:

Example A59

Preparation of (R)-6-(5-bromo-2-fluorophenyl)-2-(difluoromethyl)-6-methyl-5,6-dihydroimidazo[1,2-a]pyrazin-8-amine

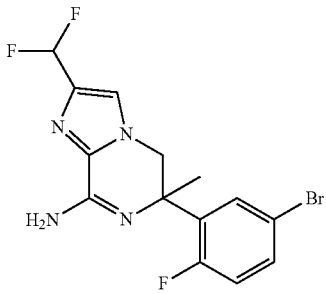 [SMILES: CC1(c2cc(Br)ccc2F)Cn2cc(C(F)F)nc2C(N)=N1]

From (R)-6-(5-bromo-2-fluorophenyl)-2-(difluoromethyl)-6-methyl-6,7-dihydroimidazo[1,2-a]pyrazine-8(5H)-thione.

Example A60

Preparation of (R)-6-(5-bromo-2-fluorophenyl)-6-methyl-2-(trifluoromethyl)-5,6-dihydroimidazo[1,2-a]pyrazin-8-amine

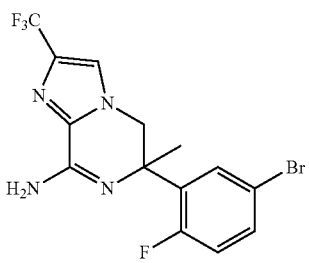 [SMILES: CC1(c2cc(Br)ccc2F)Cn2cc(C(F)(F)F)nc2C(N)=N1]

A solution of (R)-tert-butyl {1-(5-bromo-2-fluorophenyl)-2-[2-cyano-4-(trifluoromethyl)-1H-imidazol-1-yl]-1-methylethyl}carbamate (2.95 g, 6 mmol) in HCl 4 M in dioxane (50 mL) was stirred at 70° C. for 2 hours. The mixture was concentrated in vacuo and the residue was suspended in DCM and washed with Na$_2$CO$_3$ (sat.). The organic layer was separated, dried (MgSO$_4$), filtered and the solvent was evaporated in vacuo. The crude product was purified by flash column chromatography (silica; 7 M solution of ammonia in MeOH in DCM 0/100 to 1/99). The desired fractions were collected and evaporated in vacuo to yield (R)-6-(5-bromo-2-fluorophenyl)-6-methyl-2-(trifluoromethyl)-5,6-dihydroimidazo[1,2-a]pyrazin-8-amine (1.5 g, 64% yield).

The following intermediates were prepared according to a similar synthetic procedure described in example A60:

Example A61

Preparation of (R)-6-(5-bromo-2-fluorophenyl)-6-methyl-5,6-dihydroimidazo[1,2-a]-pyrazin-8-amine

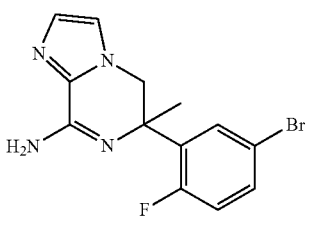 [SMILES: CC1(c2cc(Br)ccc2F)Cn2ccnc2C(N)=N1]

From (R)-tert-butyl [1-(5-bromo-2-fluorophenyl)-2-(2-cyano-1H-imidazol-1-yl)-1-methylethyl]carbamate.

Example A62

Preparation of (R)-6-(5-bromo-2-fluorophenyl)-2-chloro-6-methyl-5,6-dihydroimidazo[1,2-a]pyrazin-8-amine

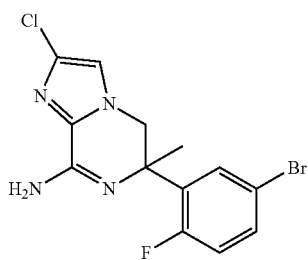 [SMILES: CC1(c2cc(Br)ccc2F)Cn2cc(Cl)nc2C(N)=N1]

From (R)-tert-butyl [1-(5-bromo-2-fluorophenyl)-2-(4-chloro-2-cyano-1H-imidazol-1-yl)-1-methylethyl]carbamate.

Example A63

Preparation of (R)-ethyl {3-[8-amino-2-chloro-6-methyl-5,6-dihydroimidazo[1,2-a]-pyrazin-6-yl]-4-fluorophenyl}carbamate

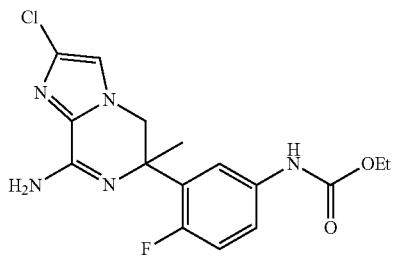 [SMILES: CCOC(=O)Nc1ccc(F)c(C2(C)Cn3cc(Cl)nc3C(N)=N2)c1]

From (R)-ethyl {3-[1-[(tert-butoxycarbonyl)amino]-2-(4-chloro-2-cyano-1H-imidazol-1-yl)-1-methylethyl]-4-fluorophenyl}carbamate.

Example A64

Preparation of (R)-ethyl {3-[8-amino-2-bromo-6-methyl-5,6-dihydroimidazo[1,2-a]-pyrazin-6-yl]-4-fluorophenyl}carbamate

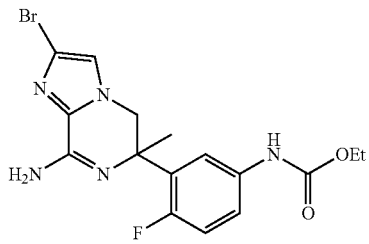 [SMILES: CCOC(=O)Nc1ccc(F)c(C2(C)Cn3cc(Br)nc3C(N)=N2)c1]

From (R)-ethyl (3-{2-(4-bromo-2-cyano-1H-imidazol-1-yl)-1-[(tert-butoxycarbonyl)amino]-1-methylethyl}-4-fluorophenyl)carbamate.

Example A65

Preparation of (R)-ethyl {3-[8-amino-2-iodo-6-methyl-5,6-dihydroimidazo[1,2-a]-pyrazin-6-yl]-4-fluorophenyl}carbamate

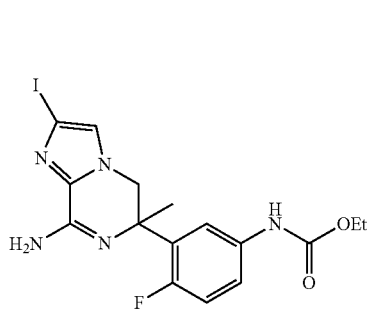 [SMILES: CCOC(=O)Nc1ccc(F)c(C2(C)Cn3cc(I)nc3C(N)=N2)c1]

From (R)-ethyl {3-[1-[(tert-butoxycarbonyl)amino]-2-(2-cyano-4-iodo-1H-imidazol-1-yl)-1-methylethyl]-4-fluorophenyl}carbamate.

Example A66

Preparation of (R)-6-(5-bromo-2-fluorophenyl)-3-chloro-6-methyl-5,6-dihydroimidazo[1,2-a]pyrazin-8-amine

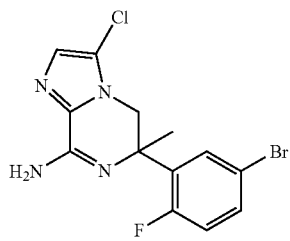 [SMILES: CC1(c2cc(Br)ccc2F)Cn2c(Cl)cnc2C(N)=N1]

N-chlorosuccinimide (0.123 g, 0.92 mmol) was added to a stirred solution of (R)-6-(5-bromo-2-fluorophenyl)-6-methyl-5,6-dihydroimidazo[1,2-a]pyrazin-8-amine (0.27 g, 0.84 mmol) in acetic acid (6.23 mL). The mixture was stirred at 80° C. for 16 hours and then diluted with water and extracted with DCM. The organic layer was separated, dried (MgSO$_4$), filtered and the solvent was evaporated in vacuo. The crude product was purified by flash column chromatography (silica; 7 M solution of ammonia in MeOH in DCM 0/100 to 3/97). The desired fractions were collected and evaporated in vacuo to yield (R)-6-(5-bromo-2-fluorophenyl)-3-chloro-6-methyl-5,6-dihydroimidazo[1,2-a]pyrazin-8-amine (0.18 g, 61% yield) as a white solid.

The following intermediate was prepared according to a similar synthetic procedure described in example A66:

Example A67

Preparation of (R)-6-(5-bromo-2-fluorophenyl)-6-methyl-5,6-dihydroimidazo[1,2-a]-pyrazin-8-amine

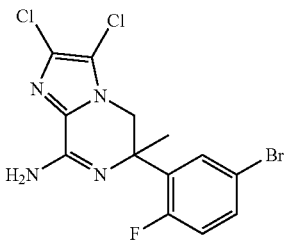 [SMILES: CC1(c2cc(Br)ccc2F)Cn2c(nc(Cl)c2Cl)C(N)=N1]

From (R)-6-(5-bromo-2-fluorophenyl)-2-chloro-6-methyl-5,6-dihydroimidazo[1,2-a]-pyrazin-8-amine.

Example A68

Preparation of (R)-6-(5-amino-2-fluorophenyl)-2-chloro-6-methyl-5,6-dihydroimidazo[1,2-a]pyrazin-8-amine

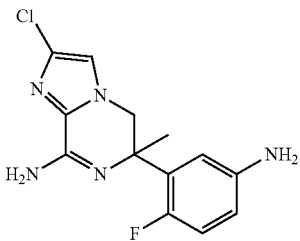 [SMILES: CC1(c2cc(N)ccc2F)Cn2cc(Cl)nc2C(N)=N1]

A mixture of (R)-ethyl {3-[8-amino-2-chloro-6-methyl-5,6-dihydroimidazo[1,2-a]pyrazin-6-yl]-4-fluorophenyl}carbamate (0.2 g, 0.55 mmol), sulfuric acid (2 mL, 37.5 mmol), water (2 mL) and acetic acid (0.8 mL, 13.9 mmol) was stirred at 110° C. for 2 hours. The mixture was taken up in EtOAc and basified with sat. Na$_2$CO$_3$. The organic layer was separated, dried (MgSO$_4$), filtered and the solvent was evaporated in vacuo to yield (R)-6-(5-amino-2-fluorophenyl)-2-chloro-6-methyl-5,6-dihydroimidazo[1,2-a]pyrazin-8-amine (0.17 g, 79% yield) that was used in the next step without any further purification.

Example A69

Preparation of (R)-6-(5-amino-2-fluorophenyl)-2-bromo-6-methyl-5,6-dihydroimidazo[1,2-a]pyrazin-8-amine

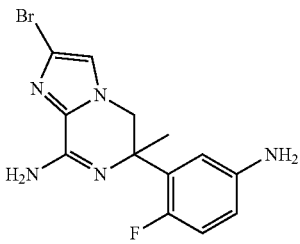 [SMILES: CC1(c2cc(N)ccc2F)Cn2cc(Br)nc2C(N)=N1]

Potassium hydroxide (0.98 g, 17.6 mmol) was added to a stirred solution of (R)-ethyl {3-[8-amino-2-bromo-6-methyl-5,6-dihydroimidazo[1,2-a]pyrazin-6-yl]-4-fluorophenyl}carbamate (0.72 g, 1.76 mmol) in EtOH (10.25 mL). The mixture was stirred at 85° C. for 24 hours. The mixture was diluted with in DCM and EtOAc and washed with water. The organic layer was separated, dried (MgSO$_4$), filtered and the solvent was evaporated in vacuo to yield (R)-6-(5-amino-2-fluorophenyl)-2-bromo-6-methyl-5,6-dihydroimidazo[1,2-a]pyrazin-8-amine (0.6 g, 100% yield) that was used in the next step without any further purification.

The following intermediate was prepared according to a similar synthetic procedure described in example A69:

Example A70

Preparation of (R)-6-(5-amino-2-fluorophenyl)-2-iodo-6-methyl-5,6-dihydroimidazo[1,2-a]pyrazin-8-amine

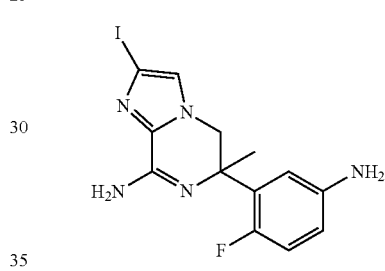

From (R)-ethyl {3-[8-amino-2-iodo-6-methyl-5,6-dihydroimidazo[1,2-a]pyrazin-6-yl]-4-fluorophenyl}carbamate.

Example A71

Preparation of rac-6-(3-amino-phenyl)-6-methyl-5,6-dihydro-imidazo[1,2-a]pyrazin-8-ylamine

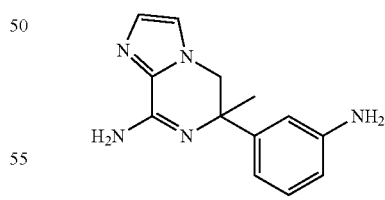

A solution of rac-6-(3-nitro-phenyl)-6-methyl-5,6-dihydro-imidazo[1,2-a]pyrazin-8-ylamine (310 mg, 1.14 mmol) in ethanol (28 mL) was hydrogenated in a H-Cube reactor (1 mL/min., 30 mm, Pd/C 5% cartridge, full hydrogen mode, room temperature, 2 cycles). The reaction was concentrated in vacuo to yield rac-6-(3-amino-phenyl)-6-methyl-5,6-dihydro-imidazo[1,2-a]pyrazin-8-ylamine (250 mg, 91%) as a white solid.

Example A72

Preparation of (R)-6-[5-(benzhydrylidene-amino)-2-fluoro-phenyl]-6-methyl-5,6-dihydro-imidazo[1,2-a]pyrazin-8-ylamine

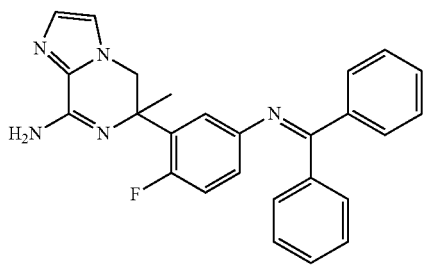 [SMILES: CC1(c2cc(N=C(c3ccccc3)c3ccccc3)ccc2F)Cn2ccnc2C(N)=N1]

Toluene (10 mL) was added to a mixture of (R)-6-(5-bromo-2-fluoro-phenyl)-6-methyl-5,6-dihydro-imidazo[1,2-a]pyrazin-8-ylamine (0.60 g, 1.86 mmol), tris(dibenzylideneacetone)dipalladium(0) (0.17 g, 0.19 mmol), rac-2,2'-bis(diphenyl-phosphino)-1,1'-binaphthyl (0.35 g, 0.56 mmol) and sodium tert-butoxide (0.32 g, 3.3 mmol) in a sealed tube and under nitrogen at room temperature. The mixture was flushed with nitrogen for a few minutes and then benzophenone imine (0.62 mL, 3.71 mmol) was added and the mixture was stirred at 100° C. for 2 hours. After cooling to room temperature, the mixture was diluted with water and extracted with DCM. The organic layer was separated, dried (MgSO$_4$), filtered and the solvent was evaporated in vacuo. The crude product was purified by flash column chromatography (silica; 7 M solution of ammonia in MeOH in DCM 0/100 to 2.5/96.5). The desired fractions were collected and concentrated in vacuo to yield (R)-6-[5-(benzhydrylidene-amino)-2-fluoro-phenyl]-6-methyl-5,6-dihydro-imidazo[1,2-a]pyrazin-8-ylamine (0.55 g, 70% yield) as a yellow solid.

Example A73

Preparation of (R)-6-(5-amino-2-fluoro-phenyl)-6-methyl-5,6-dihydro-imidazo[1,2-a]-pyrazin-8-ylamine

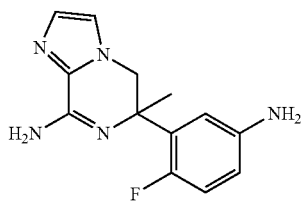 [SMILES: CC1(c2cc(N)ccc2F)Cn2ccnc2C(N)=N1]

Hydrochloric acid 37% in H$_2$O (0.11 mL) was added to a solution of (R)-6-[5-(benzhydrylidene-amino)-2-fluoro-phenyl]-6-methyl-5,6-dihydro-imidazo[1,2-a]pyrazin-8-ylamine (0.31 g, 0.73 mmol) in isopropanol (8 mL). The mixture was stirred at room temperature for 2 hours. The solvent was evaporated in vacuo. Diethyl ether was added to the residue and the mixture was stirred at room temperature for 15 minutes. The precipitate was filtered off, washed with diethyl ether and dried in vacuo. The residue was suspended in DCM and washed with NaHCO$_3$ (sat). The organic layer was separated, dried (MgSO$_4$), filtered and the solvent was evaporated in vacuo to yield (R)-6-(5-amino-2-fluoro-phenyl)-6-methyl-5,6-dihydro-imidazo[1,2-a]pyrazin-8-ylamine (0.11 g, 58% yield) that was used in the next step without any further purification.

The following intermediates were prepared according to similar synthetic procedures described in examples A72-A73:

Example A74

Preparation of rac-6-(5-amino-2-fluorophenyl)-6-(difluoromethyl)-5,6-dihydroimidazo[1,2-a]pyrazin-8-amine

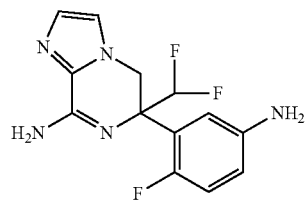 [SMILES: NC1=NC(c2cc(N)ccc2F)(C(F)F)Cn2ccnc21]

From rac-6-(5-bromo-2-fluorophenyl)-6-(difluoromethyl)-5,6-dihydroimidazo[1,2-a]-pyrazin-8-amine

Example A75

Preparation of (R)-6-(5-amino-2-fluorophenyl)-2-(difluoromethyl)-6-methyl-5,6-dihydroimidazo[1,2-a]pyrazin-8-amine

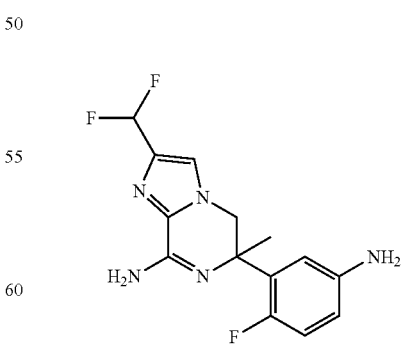

From (R)-6-(5-bromo-2-fluorophenyl)-2-(difluoromethyl)-6-methyl-5,6-dihydroimidazo[1,2-a]pyrazin-8-amine.

Example A76

Preparation of (R)-6-(5-amino-2-fluorophenyl)-6-methyl-2-(trifluoromethyl)-5,6-dihydroimidazo[1,2-a]pyrazin-8-amine

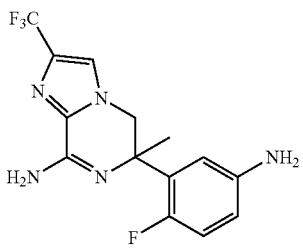 [SMILES: CC1(c2cc(N)ccc2F)Cn2cc(C(F)(F)F)nc2C(N)=N1]

Dimethyl sulfoxide (69.5 mL) was added to a mixture of (R)-6-(5-bromo-2-fluorophenyl)-6-methyl-2-(trifluoromethyl)-5,6-dihydroimidazo[1,2-a]pyrazin-8-amine (1.9 g, 4.86 mmol), sodium azide (0.79 g, 12.1 mmol), copper(I) iodide (1.16 g, 6.1 mmol) and Na$_2$CO$_3$ (1.03 g, 9.7 mmol). The mixture was degassed with nitrogen for a few minutes and then N,N'-dimethylethylenediamine (0.91 mL, 8.5 mmol) was added and the mixture was stirred at 110° C. for 3 hours. After cooling to room temperature, the mixture was diluted with DCM and washed with NH$_4$OH (32%). The organic layer was separated, dried (MgSO$_4$), filtered and the solvent was evaporated in vacuo. The crude product was purified by flash column chromatography (silica; 7 M solution of ammonia in MeOH in DCM 0/100 to 3/97). The desired fractions were collected and concentrated in vacuo to yield (R)-6-(5-amino-2-fluorophenyl)-6-methyl-2-(trifluoromethyl)-5,6-dihydroimidazo[1,2-a]pyrazin-8-amine (0.72 g, 45% yield).

The following intermediates were prepared according to a similar synthetic procedure described in example A76:

Example A77

Preparation of (R)-6-(5-amino-2-fluorophenyl)-2-(difluoromethyl)-6-methyl-5,6-dihydroimidazo[1,2-a]pyrazin-8-amine

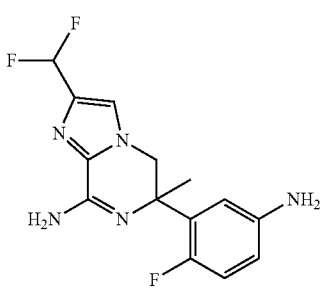 [SMILES: CC1(c2cc(N)ccc2F)Cn2cc(C(F)F)nc2C(N)=N1]

From (R)-6-(5-bromo-2-fluorophenyl)-2-(difluoromethyl)-6-methyl-5,6-dihydroimidazo[1,2-a]pyrazin-8-amine.

Example A78

Preparation of (R)-6-(5-amino-2-fluorophenyl)-3-chloro-6-methyl-5,6-dihydroimidazo[1,2-a]pyrazin-8-amine

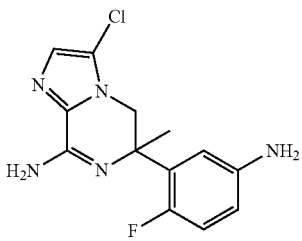 [SMILES: CC1(c2cc(N)ccc2F)Cn2c(Cl)cnc2C(N)=N1]

From (R)-6-(5-bromo-2-fluorophenyl)-3-chloro-6-methyl-5,6-dihydroimidazo[1,2-a]-pyrazin-8-amine.

Example A79

Preparation of (R)-6-(5-amino-2-fluorophenyl)-2,3-dichloro-6-methyl-5,6-dihydroimidazo[1,2-a]pyrazin-8-amine

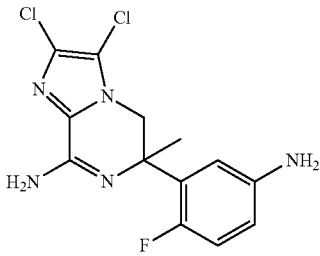

From (R)-6-(5-bromo-2-fluorophenyl)-2,3-dichloro-6-methyl-5,6-dihydroimidazo-[1,2-a]pyrazin-8-amine.

Example A80

Preparation of (R)-tert-butyl [2-bromo-6-(2-fluoro-5-{[(5-fluoropyridin-2-yl)carbonyl]amino}phenyl)-6-methyl-5,6-dihydroimidazo[1,2-a]pyrazin-8-yl]carbamate

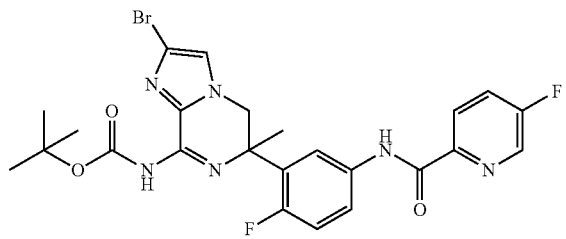 [SMILES: CC(C)(C)OC(=O)NC1=NC(C)(c2cc(NC(=O)c3ccc(F)cn3)ccc2F)Cn2cc(Br)nc21]

Di-tert-butyl dicarbonate (0.060 g, 0.27 mmol) was added to a stirred solution of (R)—N-{3-[8-amino-2-bromo-6-methyl-5,6-dihydroimidazo[1,2-a]pyrazin-6-yl]-4-fluorophenyl]-5-fluoropyridine-2-carboxamide (0.07 g, 0.15 mmol) in sat. NaHCO$_3$ (1 mL) and THF (2 mL) at 0° C. The mixture was stirred at room temperature for 18 hours. The organic layer was separated, and further extracted with EtOAc, dried (MgSO₄), filtered and the solvent was evaporated in vacuo to yield (R)-tert-butyl [2-bromo-6-(2-fluoro-5-{[(5-fluoropyridin-2-yl)carbonyl]amino}phenyl)-6-methyl-5,6-dihydroimidazo[1,2-a]pyrazin-8-yl]carbamate (0.085 g, 100% yield) that was used in the next step without any further purification.

Example A81

Preparation of (R)-tert-butyl (3-{8-[(tert-butoxycarbonyl)amino]-2-chloro-6-methyl-5,6-dihydroimidazo[1,2-a]pyrazin-6-yl}-4-fluorophenyl)carbamate

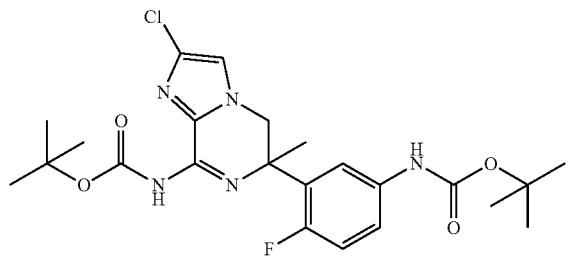 [SMILES: CC(C)(C)OC(=O)NC1=NC(C)(c2cc(NC(=O)OC(C)(C)C)ccc2F)Cn2cc(Cl)nc21]

Di-tert-butyl dicarbonate (2.89 g, 13.28 mmol) was added to a stirred solution of (R)-6-(5-amino-2-fluorophenyl)-2-chloro-6-methyl-5,6-dihydroimidazo[1,2-a]pyrazin-8-amine (1.3 g, 4.43 mmol) and DIPEA (1.91 mL, 11.06 mL) in DCM (77.5 mL). The mixture was stirred at room temperature for 24 hours. The organic layer was diluted with DCM and washed with sat. NaHCO₃. The organic layer was separated, dried (MgSO₄), filtered and the solvent was evaporated in vacuo. The crude product was purified by flash column chromatography (silica; EtOAc in DCM 0/100 to 30/70). The desired fractions were collected and evaporated in vacuo to yield (R)-tert-butyl (3-{8-[(tert-butoxycarbonyl)amino]-2-chloro-6-methyl-5,6-dihydroimidazo[1,2-a]pyrazin-6-yl}-4-fluorophenyl)carbamate (1.5 g, 69% yield).

The following intermediate was prepared according to a similar synthetic procedure described in example A81:

Example A82

Preparation of (R)-tert-butyl [6-{5-[(tert-butoxycarbonyl)amino]-2-fluorophenyl}-6-methyl-5,6-dihydroimidazo[1,2-a]pyrazin-8-yl]carbamate

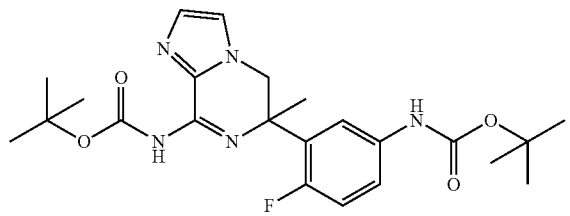 [SMILES: CC(C)(C)OC(=O)NC1=NC(C)(c2cc(NC(=O)OC(C)(C)C)ccc2F)Cn2ccnc21]

From (R)-6-(5-amino-2-fluorophenyl)-6-methyl-5,6-dihydroimidazo[1,2-a]pyrazin-8-amine.

Example A83

Preparation of (R)-tert-butyl (3-{8-[(tert-butoxycarbonyl)amino]-2-chloro-3-iodo-6-methyl-5,6-dihydroimidazo[1,2-a]pyrazin-6-yl}-4-fluorophenyl)carbamate

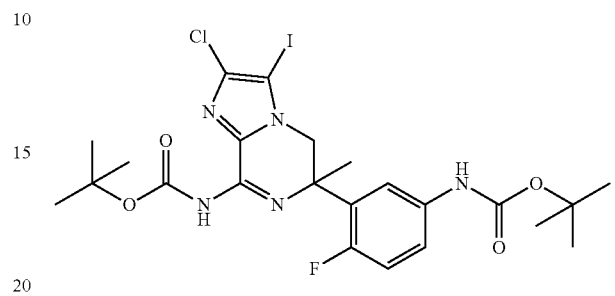

N-butyllithium (2.7 M in heptane; 11.92 mL, 32.2 mmol) was added dropwise to a stirred solution of (R)-tert-butyl (3-{8-[(tert-butoxycarbonyl)amino]-2-chloro-6-methyl-5,6-dihydroimidazo[1,2-a]pyrazin-6-yl}-4-fluorophenyl)carbamate (1.2 g, 2.43 mmol) in THF (12 mL) at −78° C. under a nitrogen atmosphere. The mixture was stirred at −78° C. for 15 minutes. Then, a solution of iodine (11.1 g, 43.73 mmol) in THF (20 mL) was added at −78° C. The mixture was stirred at −78° C. for 10 minutes. Then, the mixture was allowed to reach room temperature, diluted with EtOAc and washed sequentially with water and Na₂S₂O₃. The organic layer was separated, dried (MgSO₄), filtered and the solvent was evaporated in vacuo. The crude product was purified by flash column chromatography (silica; 7 M solution of ammonia in MeOH in DCM 0/100 to 5/95). The desired fractions were collected and evaporated in vacuo to yield (R)-tert-butyl (3-{8-[(tert-butoxycarbonyl)amino]-2-chloro-3-iodo-6-methyl-5,6-dihydroimidazo[1,2-a]pyrazin-6-yl}-4-fluorophenyl)carbamate (1.46 g, 97% yield).

The following intermediate was prepared according to a similar synthetic procedure described in example A83:

Example A84

Preparation of (R)-tert-butyl [6-{5-[(tert-butoxycarbonyl)amino]-2-fluorophenyl}-3-iodo-6-methyl-5,6-dihydroimidazo[1,2-a]pyrazin-8-yl]carbamate

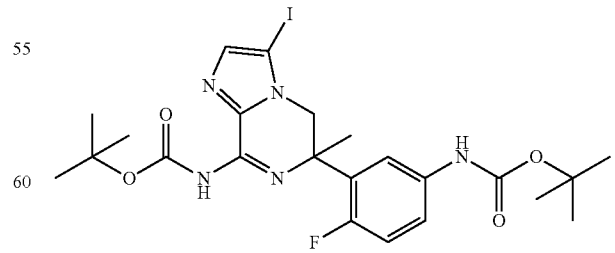

From (R)-tert-butyl [6-{5-[(tert-butoxycarbonyl)amino]-2-fluorophenyl}-6-methyl-5,6-dihydroimidazo[1,2-a]pyrazin-8-yl]carbamate.

Example A85

Preparation of (R)-tert-butyl [6-{5-[(tert-butoxycarbonyl)amino]-2-fluorophenyl}-3-(hydroxymethyl)-6-methyl-5,6-dihydroimidazo[1,2-a]pyrazin-8-yl]carbamate

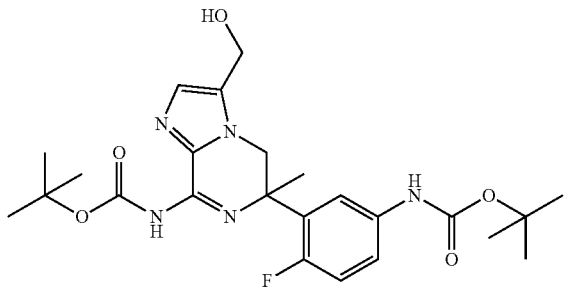 [SMILES: CC(C)(C)OC(=O)NC1=NC(C)(c2cc(NC(=O)OC(C)(C)C)ccc2F)Cn2c(CO)cnc21]

N-butyllithium (2.7 M in heptane; 25 mL, 67.5 mmol) was added dropwise to a stirred solution of (R)-tert-butyl [6-{5-[(tert-butoxycarbonyl)amino]-2-fluorophenyl}-6-methyl-5,6-dihydroimidazo[1,2-a]pyrazin-8-yl]carbamate (3.1 g, 6.75 mmol) in THF (110 mL) at −78° C. under a nitrogen atmosphere. The mixture was stirred at −78° C. for 10 minutes. Then, paraformaldehyde (6 g) was added at −78° C. Then, the mixture was allowed to reach room temperature, diluted with EtOAc and washed with water. The organic layer was separated, dried (MgSO₄), filtered and the solvent was evaporated in vacuo. The crude product was purified by flash column chromatography (silica; 7 M solution of ammonia in MeOH in DCM 0/100 to 5/95). The desired fractions were collected and evaporated in vacuo to yield (R)-tert-butyl [6-{5-[(tert-butoxycarbonyl)-amino]-2-fluorophenyl}-3-(hydroxymethyl)-6-methyl-5,6-dihydroimidazo[1,2-a]-pyrazin-8-yl]carbamate (1.83 g, 55% yield).

Example A86

Preparation of (R)-tert-butyl [6-{5-[(tert-butoxycarbonyl)amino]-2-fluorophenyl}-3-formyl-6-methyl-5,6-dihydroimidazo[1,2-a]pyrazin-8-yl]carbamate

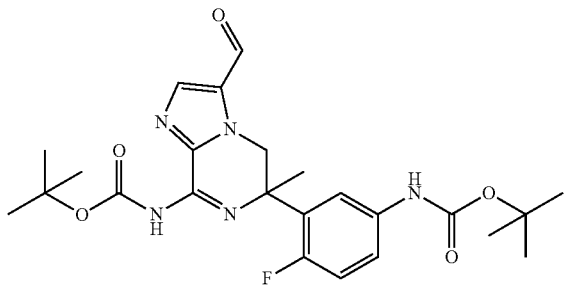 [SMILES: CC(C)(C)OC(=O)NC1=NC(C)(c2cc(NC(=O)OC(C)(C)C)ccc2F)Cn2c(C=O)cnc21]

Manganese dioxide (3.75 g, 43.1 mmol) was added to a stirred solution of (R)-tert-butyl [6-{5-[(tert-butoxycarbonyl)amino]-2-fluorophenyl}-3-(hydroxymethyl)-6-methyl-5,6-dihydroimidazo[1,2-a]pyrazin-8-yl]carbamate (1.63 g, 3.33 mmol) in DCM (12 mL). The mixture was stirred at room temperature for 2 hours. The mixture was filtered over diatomaceous earth and the filtrate was evaporated in vacuo to yield (R)-tert-butyl [6-{5-[(tert-butoxycarbonyl)amino]-2-fluorophenyl}-3-formyl-6-methyl-5,6-dihydroimidazo[1,2-a]pyrazin-8-yl]carbamate (1.42 g, 87% yield), that was used in the next step without further purification.

Example A87

Preparation of (R)-tert-butyl {3-[8-[(tert-butoxycarbonyl)amino]-3-(difluoromethyl)-6-methyl-5,6-dihydroimidazo[1,2-a]pyrazin-6-yl]-4-fluorophenyl}carbamate

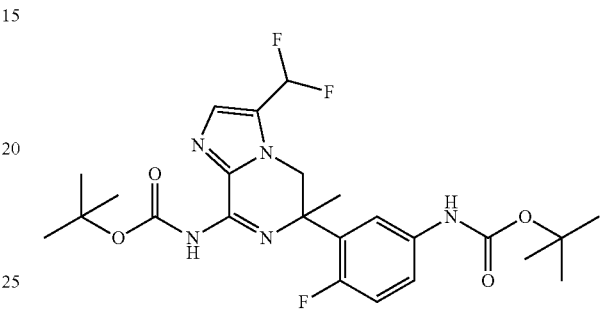

DAST (0.78 mL, 6.41 mmol) was added dropwise to a stirred solution of (R)-tert-butyl [6-{5-[(tert-butoxycarbonyl)amino]-2-fluorophenyl}-3-formyl-6-methyl-5,6-dihydroimidazo[1,2-a]pyrazin-8-yl]carbamate (1.42 g, 2.91 mmol) in DCM (15 mL) at 0° C. The mixture was stirred at room temperature for 16 hours. The mixture was evaporated in vacuo. The residue was taken up in DCM and basified with sat. NaHCO₃. The organic layer was separated, dried (MgSO₄), filtered and the solvent was evaporated in vacuo. The crude product was purified by flash column chromatography (silica; 7 M solution of ammonia in MeOH in DCM 0/100 to 1/99). The desired fractions were collected and evaporated in vacuo to yield (R)-tert-butyl {3-[8-[(tert-butoxycarbonyl)amino]-3-(difluoromethyl)-6-methyl-5,6-dihydroimidazo[1,2-a]pyrazin-6-yl]-4-fluorophenyl}carbamate (0.44 g, 29% yield).

Example A88

Preparation of (R)-tert-butyl [6-{5-[(tert-butoxycarbonyl)amino]-2-fluorophenyl}-2-iodo-6-methyl-5,6-dihydroimidazo[1,2-a]pyrazin-8-yl]carbamate

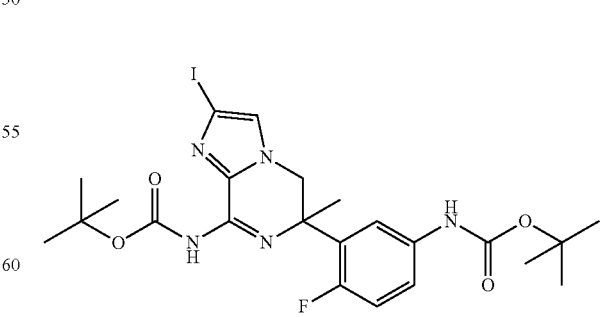

Di-tert-butyl dicarbonate (2.27 g, 10.38 mmol) was added to a stirred solution of (R)-6-(5-amino-2-fluorophenyl)-2-iodo-6-methyl-5,6-dihydroimidazo[1,2-a]pyrazin-8-amine (2 g, 5.19 mmol) in DCM (50 mL). The mixture was stirred at room temperature for 1 hour. The solvent was evaporated in vacuo. The crude product was purified by flash column chromatography (silica; 7 M solution of ammonia in MeOH in DCM 0/100 to 2/98). The desired fractions were collected and evaporated in vacuo to yield (R)-tert-butyl [6-{5-[(tert-butoxycarbonyl)amino]-2-fluorophenyl}-2-iodo-6-methyl-5,6-dihydroimidazo[1,2-a]pyrazin-8-yl]carbamate (1 g, 33% yield).

Example A89

Preparation of (R)-tert-butyl {3-[8-amino-2-chloro-3-cyano-6-methyl-5,6-dihydroimidazo[1,2-a]pyrazin-6-yl]-4-fluorophenyl}carbamate

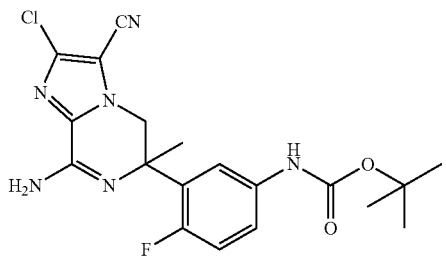 [SMILES: CC(C)(C)OC(=O)Nc1ccc(F)c(C2(C)Cn3c(nc(Cl)c3C#N)C(N)=N2)c1]

Tris(dibenzylideneacetone)dipalladium(0) (38.4 mg, 0.042 mmol) was added to a stirred suspension of (R)-tert-butyl (3-{8-[(tert-butoxycarbonyl)amino]-2-chloro-3-iodo-6-methyl-5,6-dihydroimidazo[1,2-a]pyrazin-6-yl}-4-fluorophenyl)carbamate (1.3 g, 2.1 mmol), 1,1'-bis(diphenylphosphino)ferrocene (46.5 mg, 0.084 mmol), zinc (16.5 mg, 0.25 mmol) and zinc cyanide (0.492 g, 4.19 mmol) in DMA (12 mL). The mixture was stirred at 150° C. for 30 minutes under microwave irradiation. The mixture was filtered over diatomaceous earth and the residue was diluted with DCM and washed with NH₄OH. The organic layer was separated, dried (MgSO₄), filtered and the solvent was evaporated in vacuo. The crude product was purified by flash column chromatography (silica; MeOH in DCM 0/100 to 3/97). The desired fractions were collected and concentrated in vacuo to yield (R)-tert-butyl {3-[8-amino-2-chloro-3-cyano-6-methyl-5,6-dihydroimidazo[1,2-a]pyrazin-6-yl]-4-fluorophenyl}carbamate (0.56 g, 64% yield).

The following intermediate was prepared according to a similar synthetic procedure described in example A89:

Example A90

Preparation of (R)-tert-butyl {3-[8-amino-2-cyano-6-methyl-5,6-dihydroimidazo-[1,2-a]pyrazin-6-yl]-4-fluorophenyl}carbamate

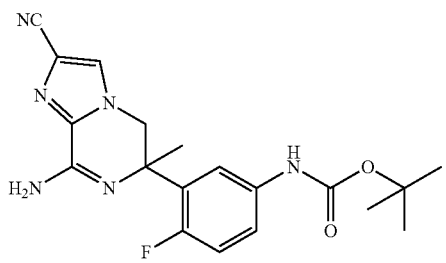 [SMILES: CC(C)(C)OC(=O)Nc1ccc(F)c(C2(C)Cn3cc(C#N)nc3C(N)=N2)c1]

From (R)-tert-butyl [6-{5-[(tert-butoxycarbonyl)amino]-2-fluorophenyl}-2-iodo-6-methyl-5,6-dihydroimidazo[1,2-a]pyrazin-8-yl]carbamate.

Example A91

Preparation of (R)-tert-butyl {3-[8-amino-3-cyano-6-methyl-5,6-dihydroimidazo-[1,2-a]pyrazin-6-yl]-4-fluorophenyl}carbamate

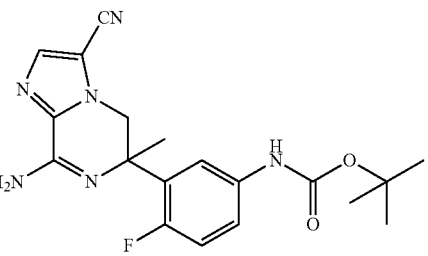

Tetrakis(triphenylphosphine)palladium(0) (0.24 g, 0.2 mmol) was added to a stirred solution of (R)-tert-butyl (3-{8-[(tert-butoxycarbonyl)amino]-3-iodo-6-methyl-5,6-dihydroimidazo[1,2-a]pyrazin-6-yl}-4-fluorophenyl)carbamate (1.2 g, 2.05 mmol) and zinc cyanide (1.93 g, 16.4 mmol) in DMF (6 mL). The mixture was stirred at 160° C. for 10 minutes under microwave irradiation. The mixture was filtered over diatomaceous earth and the solvent was evaporated in vacuo. The crude product was purified by flash column chromatography (silica; 7 M solution of ammonia in MeOH in DCM 0/100 to 3/97). The desired fractions were collected and concentrated in vacuo to yield (R)-tert-butyl {3-[8-amino-3-cyano-6-methyl-5,6-dihydroimidazo[1,2-a]pyrazin-6-yl]-4-fluorophenyl}carbamate (0.4 g, 51% yield).

Example A92

Preparation of (R)-8-amino-6-(5-amino-2-fluorophenyl)-2-chloro-6-methyl-5,6-dihydroimidazo[1,2-a]pyrazine-3-carbonitrile

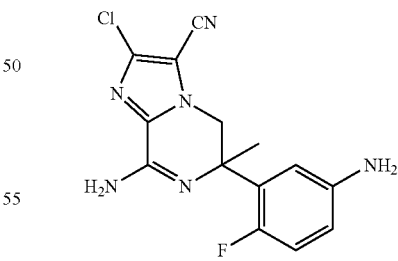

Trifluoroacetic acid (5 mL, 65.34 mmol) was added to a stirred solution of (R)-tert-butyl {3-[8-amino-2-chloro-3-cyano-6-methyl-5,6-dihydroimidazo[1,2-a]pyrazin-6-yl]-4-fluorophenyl}carbamate (0.56 g, 1.34 mmol) in DCM (20 mL). The mixture was stirred at room temperature for 30 minutes. The solvent was evaporated in vacuo and the residue was dissolved in DCM and washed with sat. NaHCO₃. The organic layer was separated, dried (MgSO₄), filtered and the solvent was evaporated in vacuo. The crude product was purified by flash column chromatography (silica; MeOH in DCM 0/100 to 3/97). The desired fractions were collected and concentrated in vacuo to yield (R)-8-amino-6-(5-amino-2-fluorophenyl)-2-chloro-6-methyl-5,6-dihydroimidazo[1,2-a]pyrazine-3-carbonitrile (0.21 g, 49% yield).

The following intermediates were prepared according to a similar synthetic procedure described in example A92:

Example A93

Preparation of (R)-8-amino-6-(5-amino-2-fluorophenyl)-6-methyl-5,6-dihydroimidazo[1,2-a]pyrazine-3-carbonitrile

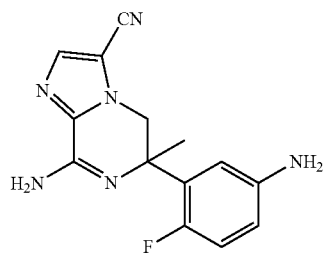 [SMILES: CC1(c2cc(N)ccc2F)Cn2c(C#N)cnc2C(N)=N1]

From (R)-tert-butyl {3-[8-amino-3-cyano-6-methyl-5,6-dihydroimidazo[1,2-a]pyrazin-6-yl]-4-fluorophenyl}carbamate.

Example A94

Preparation of (R)-6-(5-amino-2-fluorophenyl)-3-(difluoromethyl)-6-methyl-5,6-dihydroimidazo[1,2-a]pyrazin-8-amine

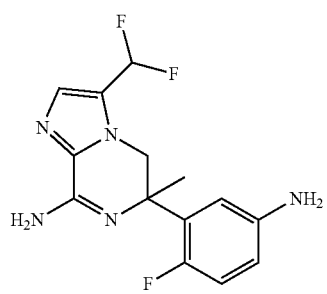 [SMILES: CC1(c2cc(N)ccc2F)Cn2c(C(F)F)cnc2C(N)=N1]

From (R)-tert-butyl {3-[8-[(tert-butoxycarbonyl)amino]-3-(difluoromethyl)-6-methyl-5,6-dihydroimidazo[1,2-a]pyrazin-6-yl]-4-fluorophenyl}carbamate.

Example A95

Preparation of (R)-8-amino-6-(5-amino-2-fluorophenyl)-6-methyl-5,6-dihydroimidazo[1,2-a]pyrazine-2-carbonitrile

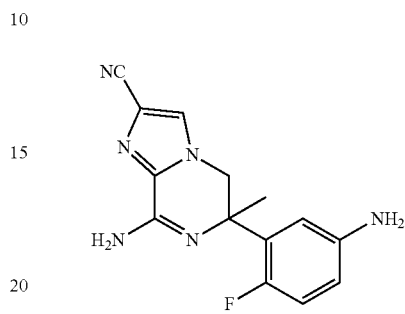

From (R)-tert-butyl {3-[8-amino-2-cyano-6-methyl-5,6-dihydroimidazo[1,2-a]pyrazin-6-yl]-4-fluorophenyl}carbamate.

Example A96

Preparation of (R)-tert-butyl [6-(5-amino-2-fluorophenyl)-2-chloro-3-cyano-6-methyl-5,6-dihydroimidazo[1,2-a]pyrazin-8-yl]carbamate

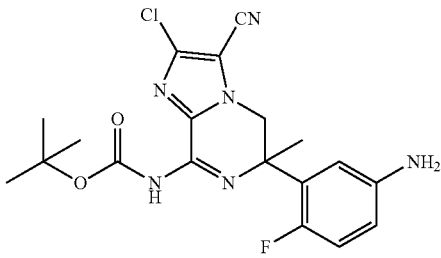 [SMILES: CC(C)(C)OC(=O)NC1=NC(C)(c2cc(N)ccc2F)Cn2c1nc(Cl)c2C#N]

Di-tert-butyl dicarbonate (0.14 g, 0.65 mmol) was added to a stirred solution of (R)-8-amino-6-(5-amino-2-fluorophenyl)-2-chloro-6-methyl-5,6-dihydroimidazo[1,2-a]pyrazine-3-carbonitrile (0.21 g, 0.66 mmol) in DCM (11.5 mL). The mixture was stirred at room temperature for 30 minutes. The mixture was diluted with sat. NaHCO$_3$ and extracted with DCM. The organic layer was separated, dried (MgSO$_4$), filtered and the solvent was evaporated in vacuo. The crude product was purified by flash column chromatography (silica; MeOH in DCM 0/100 to 3/97). The desired fractions were collected and evaporated in vacuo to yield (R)-tert-butyl [6-(5-amino-2-fluorophenyl)-2-chloro-3-cyano-6-methyl-5,6-dihydroimidazo[1,2-a]pyrazin-8-yl]carbamate (0.25 g, 91% yield).

The following intermediates were prepared according to a similar synthetic procedure described in example A96:

Example A97

Preparation of (R)-tert-butyl [6-(5-amino-2-fluorophenyl)-3-cyano-6-methyl-5,6-dihydroimidazo[1,2-a]pyrazin-8-yl]carbamate

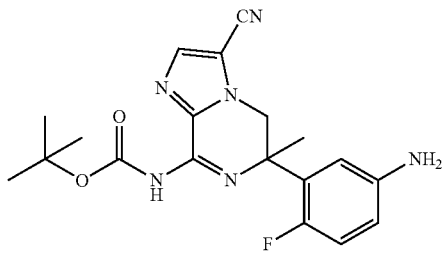 [SMILES: CC(C)(C)OC(=O)NC1=NC(C)(c2cc(N)ccc2F)Cn2c(C#N)cnc21]

From (R)-8-amino-6-(5-amino-2-fluorophenyl)-6-methyl-5,6-dihydroimidazo[1,2-a]pyrazine-3-carbonitrile.

Example A98

Preparation of (R)-tert-butyl (3-{8-[(tert-butoxycarbonyl)amino]-2-chloro-6-methyl-5,6-dihydroimidazo[1,2-a]pyrazin-6-yl}-4-fluorophenyl)carbamate

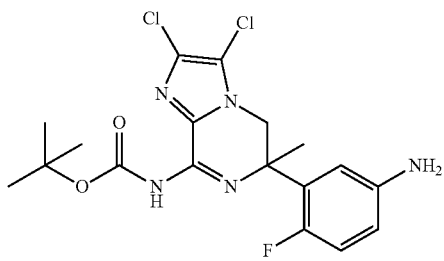 [SMILES: CC(C)(C)OC(=O)NC1=NC(C)(c2cc(N)ccc2F)Cn2c1nc(Cl)c2Cl]

From of (R)-6-(5-amino-2-fluorophenyl)-2,3-dichloro-6-methyl-5,6-dihydroimidazo[1,2-a]pyrazin-8-amine.

Example A99

Preparation of (R)-tert-butyl [6-(5-amino-2-fluorophenyl)-3-(difluoromethyl)-6-methyl-5,6-dihydroimidazo[1,2-a]pyrazin-8-yl]carbamate

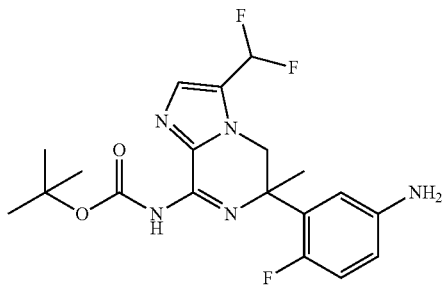 [SMILES: CC(C)(C)OC(=O)NC1=NC(C)(c2cc(N)ccc2F)Cn2c(C(F)F)cnc21]

From (R)-6-(5-amino-2-fluorophenyl)-3-(difluoromethyl)-6-methyl-5,6-dihydroimidazo[1,2-a]pyrazin-8-amine.

Example A100

Preparation of (R)-tert-butyl [2-chloro-3-cyano-6-(2-fluoro-5-{[(5-fluoropyridin-2-yl)carbonyl]amino}phenyl)-6-methyl-5,6-dihydroimidazo[1,2-a]pyrazin-8-yl]carbamate

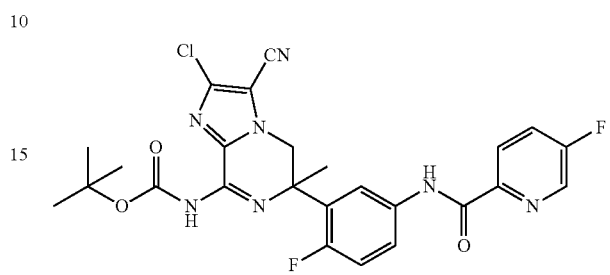

5-Fluoro-2-pyridinecarboxylic acid (15 mg, 0.11 mmol) was added to a solution of 4-(4,6-dimethoxy-1,3,5-triazin-2-yl)-4-methylmorpholinium chloride (31.7 mg, 0.11 mmol) in MeOH (0.95 mL). The mixture was stirred at room temperature for 5 minutes. The mixture was cooled to 0° C. and a solution of (R)-tert-butyl [6-(5-amino-2-fluorophenyl)-2-chloro-3-cyano-6-methyl-5,6-dihydroimidazo[1,2-a]pyrazin-8-yl]carbamate (40 mg, 0.095 mmol) in MeOH (0.95 mL) was added. The mixture was warmed to room temperature and stirred for 24 hours. The solvent was evaporated in vacuo. The crude product was purified by flash column chromatography (silica; 7N NH$_3$ in MeOH in DCM 0/100 to 3/97). The desired fractions were collected and the solvents evaporated in vacuo to yield (R)-tert-butyl [2-chloro-3-cyano-6-(2-fluoro-5-{[(5-fluoropyridin-2-yl)carbonyl]amino}phenyl)-6-methyl-5,6-dihydroimidazo[1,2-a]pyrazin-8-yl]carbamate (40 mg, 77% yield).

The following intermediates were prepared according to a similar synthetic procedure described in example A100:

Example A101

Preparation of (R)-tert-butyl [2-chloro-3-cyano-6-(2-fluoro-5-{[(5-methoxypyrazin-2-yl)carbonyl]amino}phenyl)-6-methyl-5,6-dihydroimidazo[1,2-a]pyrazin-8-yl]carbamate

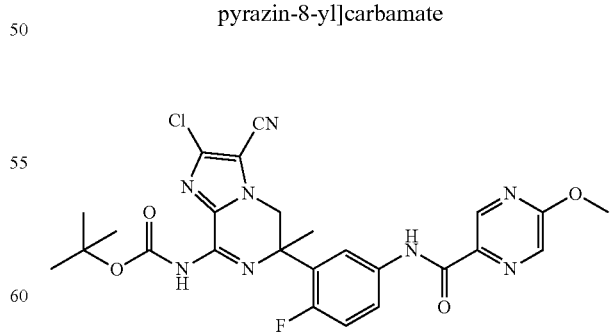

From (R)-tert-butyl [6-(5-amino-2-fluorophenyl)-2-chloro-3-cyano-6-methyl-5,6-dihydroimidazo[1,2-a]pyrazin-8-yl]carbamate and 5-methoxypyrazine-2-carboxylic acid.

Example A102

Preparation of (R)-tert-butyl [2-chloro-6-(5-{[(5-chloropyridin-2-yl)carbonyl]amino}-2-fluorophenyl)-3-cyano-6-methyl-5,6-dihydroimidazo[1,2-a]pyrazin-8-yl]carbamate

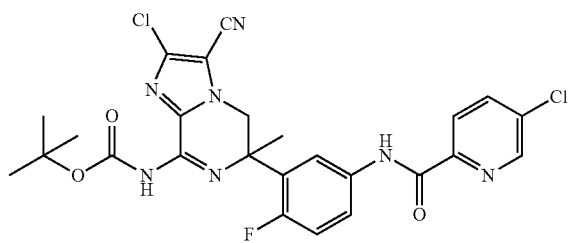 [SMILES: CC(C)(C)OC(=O)NC1=NC(C)(c2cc(NC(=O)c3ccc(Cl)cn3)ccc2F)Cn2c1nc(Cl)c2C#N]

From (R)-tert-butyl [6-(5-amino-2-fluorophenyl)-2-chloro-3-cyano-6-methyl-5,6-dihydroimidazo[1,2-a]pyrazin-8-yl]carbamate and 5-chloropyridine-2-carboxylic acid.

Example A103

Preparation of (R)-tert-butyl [2-chloro-3-cyano-6-(5-{[(5-cyanopyridin-2-yl)carbonyl]amino}-2-fluorophenyl)-6-methyl-5,6-dihydroimidazo[1,2-a]pyrazin-8-yl]carbamate

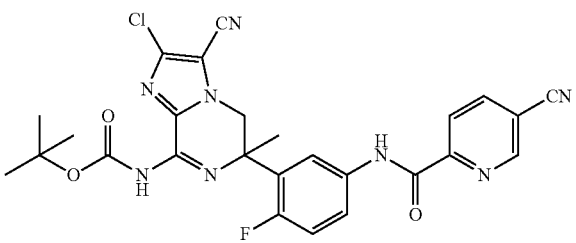 [SMILES: CC(C)(C)OC(=O)NC1=NC(C)(c2cc(NC(=O)c3ccc(C#N)cn3)ccc2F)Cn2c1nc(Cl)c2C#N]

From (R)-tert-butyl [6-(5-amino-2-fluorophenyl)-2-chloro-3-cyano-6-methyl-5,6-dihydroimidazo[1,2-a]pyrazin-8-yl]carbamate and 5-cyanopyridine-2-carboxylic acid.

Example A104

Preparation of (R)-tert-butyl {2-chloro-3-cyano-6-[5-({[1-(difluoromethyl)-1H-pyrazol-3-yl]carbonyl}amino)-2-fluorophenyl]-6-methyl-5,6-dihydroimidazo[1,2-a]pyrazin-8-yl}carbamate

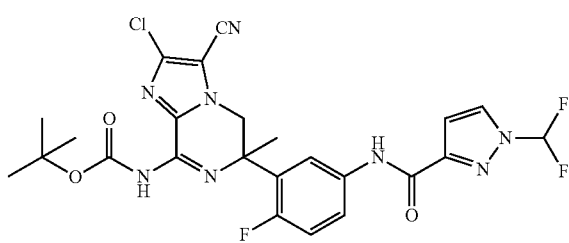 [SMILES: CC(C)(C)OC(=O)NC1=NC(C)(c2cc(NC(=O)c3ccn(C(F)F)n3)ccc2F)Cn2c1nc(Cl)c2C#N]

From (R)-tert-butyl [6-(5-amino-2-fluorophenyl)-2-chloro-3-cyano-6-methyl-5,6-dihydroimidazo[1,2-a]pyrazin-8-yl]carbamate and 1-difluoromethyl-1H-pyrazole-3-carboxylic acid.

Example A105

Preparation of (R)-tert-butyl [3-cyano-6-(2-fluoro-5-{[(5-methoxypyrazin-2-yl)carbonyl]amino}phenyl)-6-methyl-5,6-dihydroimidazo[1,2-a]pyrazin-8-yl]carbamate

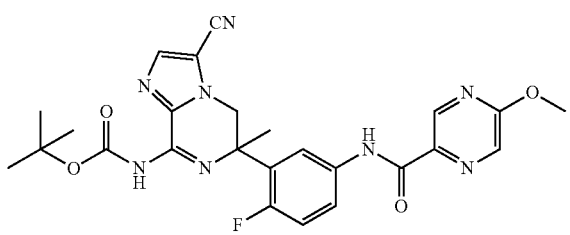 [SMILES: COc1cnc(C(=O)Nc2ccc(F)c(C3(C)Cn4c(C#N)cnc4C(NC(=O)OC(C)(C)C)=N3)c2)cn1]

From (R)-tert-butyl [6-(5-amino-2-fluorophenyl)-3-cyano-6-methyl-5,6-dihydroimidazo[1,2-a]pyrazin-8-yl]carbamate and 5-methoxypyrazine-2-carboxylic acid.

Example A106

Preparation of (R)-tert-butyl {3-cyano-6-[5-({[1-(difluoromethyl)-1H-pyrazol-3-yl]carbonyl}amino)-2-fluorophenyl]-6-methyl-5,6-dihydroimidazo[1,2-a]pyrazin-8-yl}carbamate

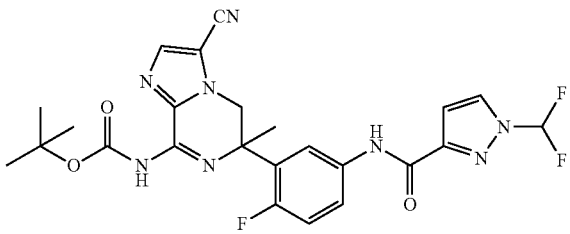 [SMILES: CC(C)(C)OC(=O)NC1=NC(C)(c2cc(NC(=O)c3ccn(C(F)F)n3)ccc2F)Cn2c(C#N)cnc21]

From (R)-tert-butyl [6-(5-amino-2-fluorophenyl)-3-cyano-6-methyl-5,6-dihydroimidazo[1,2-a]pyrazin-8-yl]carbamate and 1-difluoromethyl-1H-pyrazole-3-carboxylic acid.

Example A107

Preparation of (R)-tert-butyl [3-cyano-6-(2-fluoro-5-{[(5-fluoropyridin-2-yl)carbonyl]-amino}phenyl)-6-methyl-5,6-dihydroimidazo[1,2-a]pyrazin-8-yl]carbamate

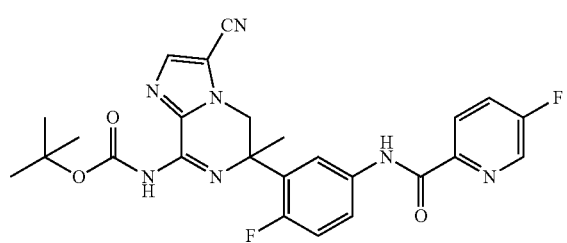 [SMILES: CC(C)(C)OC(=O)NC1=NC(C)(c2cc(NC(=O)c3ccc(F)cn3)ccc2F)Cn2c(C#N)cnc21]

From (R)-tert-butyl [6-(5-amino-2-fluorophenyl)-3-cyano-6-methyl-5,6-dihydroimidazo[1,2-a]pyrazin-8-yl]carbamate and 5-fluoro-2-pyridinecarboxylic acid.

Example A108

Preparation of (R)-tert-butyl [3-cyano-6-(5-{[(5-cyanopyridin-2-yl)carbonyl]amino}-2-fluorophenyl)-6-methyl-5,6-dihydroimidazo[1,2-a]pyrazin-8-yl]carbamate

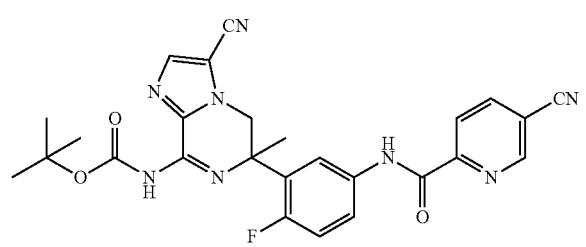 [SMILES: CC(C)(C)OC(=O)NC1=NC(C)(c2cc(NC(=O)c3ccc(C#N)cn3)ccc2F)Cn2c(C#N)cnc21]

From (R)-tert-butyl [6-(5-amino-2-fluorophenyl)-3-cyano-6-methyl-5,6-dihydroimidazo[1,2-a]pyrazin-8-yl]carbamate and 5-cyanopyridine-2-carboxylic acid.

Example A109

Preparation of (R)-tert-butyl [6-(5-{[(5-chloropyridin-2-yl)carbonyl]amino}-2-fluorophenyl)-3-cyano-6-methyl-5,6-dihydroimidazo[1,2-a]pyrazin-8-yl]carbamate

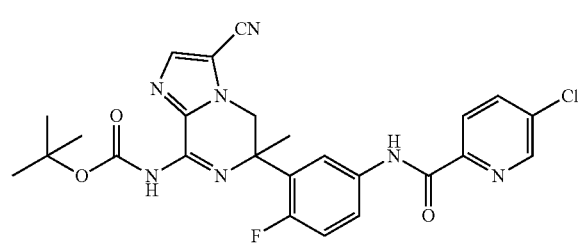 [SMILES: CC(C)(C)OC(=O)NC1=NC(C)(c2cc(NC(=O)c3ccc(Cl)cn3)ccc2F)Cn2c(C#N)cnc21]

From (R)-tert-butyl [6-(5-amino-2-fluorophenyl)-3-cyano-6-methyl-5,6-dihydroimidazo[1,2-a]pyrazin-8-yl]carbamate and 5-chloropyridine-2-carboxylic acid.

Example A110

Preparation of (R)-tert-butyl [2,3-dichloro-6-(5-{[(5-cyanopyridin-2-yl)carbonyl]amino}-2-fluorophenyl)-6-methyl-5,6-dihydroimidazo[1,2-a]pyrazin-8-yl]carbamate

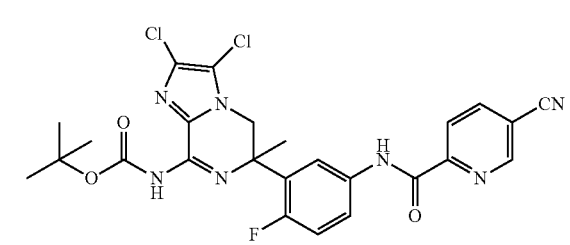 [SMILES: CC(C)(C)OC(=O)NC1=NC(C)(c2cc(NC(=O)c3ccc(C#N)cn3)ccc2F)Cn2c1nc(Cl)c2Cl]

From (R)-tert-butyl [6-(5-amino-2-fluorophenyl)-2,3-dichloro-6-methyl-5,6-dihydroimidazo[1,2-a]pyrazin-8-yl]carbamate and 5-cyanopyridine-2-carboxylic acid.

Example A111

Preparation of (R)-tert-butyl {2,3-dichloro-6-[5-({[1-(difluoromethyl)-1H-pyrazol-3-yl]carbonyl}amino)-2-fluorophenyl]-6-methyl-5,6-dihydroimidazo[1,2-a]pyrazin-8-yl}carbamate

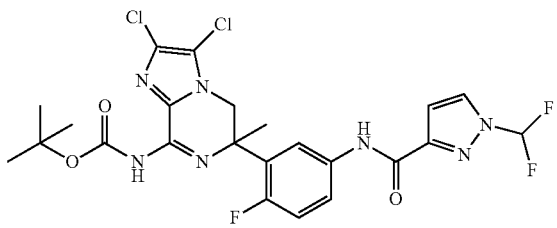 [SMILES: CC(C)(C)OC(=O)NC1=NC(C)(c2cc(NC(=O)c3ccn(C(F)F)n3)ccc2F)Cn2c1nc(Cl)c2Cl]

From (R)-tert-butyl [6-(5-amino-2-fluorophenyl)-2,3-dichloro-6-methyl-5,6-dihydroimidazo[1,2-a]pyrazin-8-yl]carbamate and 1-difluoromethyl-1H-pyrazole-3-carboxylic acid.

Example A112

Preparation of (R)-tert-butyl [2,3-dichloro-6-(5-{[(5-chloropyridin-2-yl)carbonyl]amino}-2-fluorophenyl)-6-methyl-5,6-dihydroimidazo[1,2-a]pyrazin-8-yl]carbamate

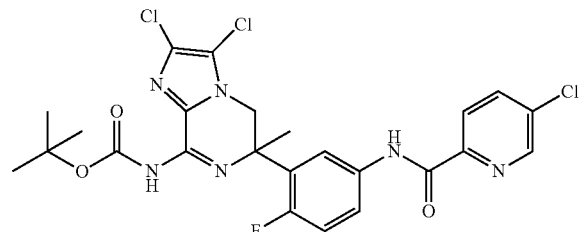

From (R)-tert-butyl [6-(5-amino-2-fluorophenyl)-2,3-dichloro-6-methyl-5,6-dihydroimidazo[1,2-a]pyrazin-8-yl]carbamate and 5-chloropyridine-2-carboxylic acid.

Example A113

Preparation of (R)-tert-butyl [2,3-dichloro-6-(2-fluoro-5-{[(5-fluoropyridin-2-yl)carbonyl]amino}phenyl)-6-methyl-5,6-dihydroimidazo[1,2-a]pyrazin-8-yl]carbamate

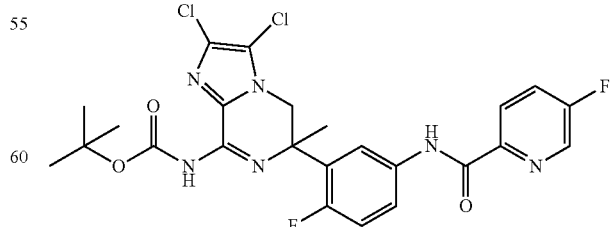

From (R)-tert-butyl [6-(5-amino-2-fluorophenyl)-2,3-dichloro-6-methyl-5,6-dihydroimidazo[1,2-a]pyrazin-8-yl]carbamate and 5-fluoro-2-pyridinecarboxylic acid.

Example A114

Preparation of (R)-tert-butyl [2,3-dichloro-6-(2-fluoro-5-{[(5-methoxypyrazin-2-yl)carbonyl]amino}phenyl)-6-methyl-5,6-dihydroimidazo[1,2-a]pyrazin-8-yl]carbamate

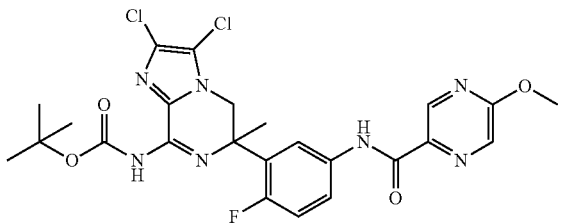 [SMILES: COc1cnc(C(=O)Nc2ccc(F)c(C3(C)Cn4c(nc(Cl)c4Cl)C(NC(=O)OC(C)(C)C)=N3)c2)cn1]

From (R)-tert-butyl [6-(5-amino-2-fluorophenyl)-2,3-dichloro-6-methyl-5,6-dihydroimidazo[1,2-a]pyrazin-8-yl]carbamate and 5-methoxypyrazine-2-carboxylic acid.

Example A115

Preparation of (R)-tert-butyl 1645-{[(5-chloropyridin-2-yl)carbonyl]amino}-2-fluorophenyl)-3-(difluoromethyl)-6-methyl-5,6-dihydroimidazo[1,2-a]pyrazin-8-yl]carbamate

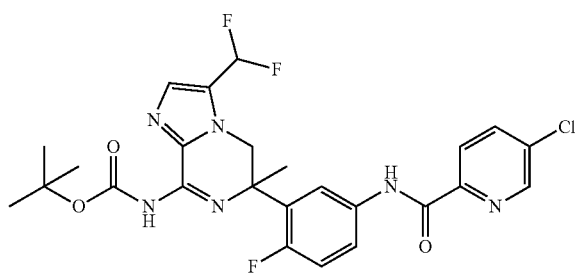 [SMILES: CC(C)(C)OC(=O)NC1=NC(C)(c2cc(NC(=O)c3ccc(Cl)cn3)ccc2F)Cn2c(C(F)F)cnc21]

From (R)-tert-butyl [6-(5-amino-2-fluorophenyl)-3-(difluoromethyl)-6-methyl-5,6-dihydroimidazo[1,2-a]pyrazin-8-yl]carbamate and 5-chloropyridine-2-carboxylic acid.

Example A116

Preparation of (R)-tert-butyl [6-(5-{[(5-cyanopyridin-2-yl)carbonyl]amino}-2-fluorophenyl)-3-(difluoromethyl)-6-methyl-5,6-dihydroimidazo[1,2-a]pyrazin-8-yl]carbamate

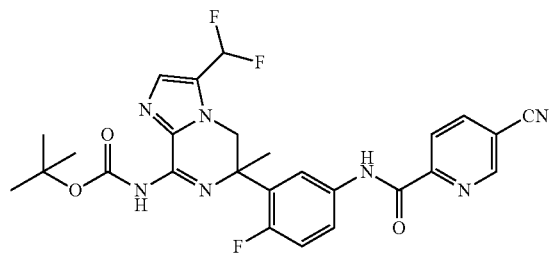 [SMILES: CC(C)(C)OC(=O)NC1=NC(C)(c2cc(NC(=O)c3ccc(C#N)cn3)ccc2F)Cn2c(C(F)F)cnc21]

From (R)-tert-butyl [6-(5-amino-2-fluorophenyl)-3-(difluoromethyl)-6-methyl-5,6-dihydroimidazo[1,2-a]pyrazin-8-yl]carbamate and 5-cyanopyridine-2-carboxylic acid.

Example A117

Preparation of (R)-tert-butyl [3-(difluoromethyl)-6-(2-fluoro-5-{[(5-methoxypyrazin-2-yl)carbonyl]amino}phenyl)-6-methyl-5,6-dihydroimidazo[1,2-a]pyrazin-8-yl]carbamate

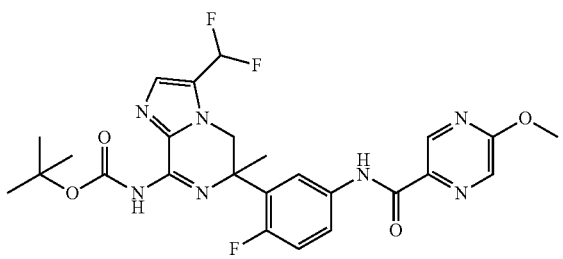 [SMILES: COc1cnc(C(=O)Nc2ccc(F)c(C3(C)Cn4c(C(F)F)cnc4C(NC(=O)OC(C)(C)C)=N3)c2)cn1]

From (R)-tert-butyl [6-(5-amino-2-fluorophenyl)-3-(difluoromethyl)-6-methyl-5,6-dihydroimidazo[1,2-a]pyrazin-8-yl]carbamate and 5-methoxypyrazine-2-carboxylic acid.

Example A118

Preparation of (R)-tert-butyl [3-(difluoromethyl)-6-(2-fluoro-5-{[(5-fluoropyridin-2-yl)carbonyl]amino}phenyl)-6-methyl-5,6-dihydroimidazo[1,2-a]pyrazin-8-yl]carbamate

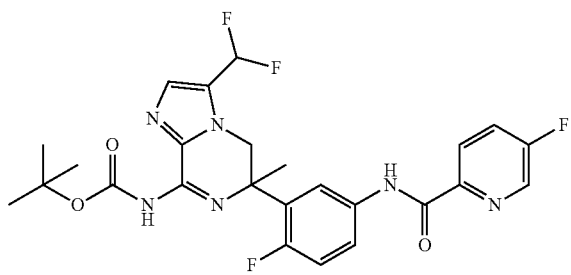 [SMILES: CC(C)(C)OC(=O)NC1=NC(C)(c2cc(NC(=O)c3ccc(F)cn3)ccc2F)Cn2c(C(F)F)cnc21]

From (R)-tert-butyl [6-(5-amino-2-fluorophenyl)-3-(difluoromethyl)-6-methyl-5,6-dihydroimidazo[1,2-a]pyrazin-8-yl]carbamate and 5-fluoro-2-pyridinecarboxylic acid.

Example A119

Preparation of (R)-tert-butyl {3-(difluoromethyl)-6-[5-({[1-(difluoromethyl)-1H-pyrazol-3-yl]carbonyl}amino)-2-fluorophenyl]-6-methyl-5,6-dihydroimidazo[1,2-a]pyrazin-8-yl}carbamate

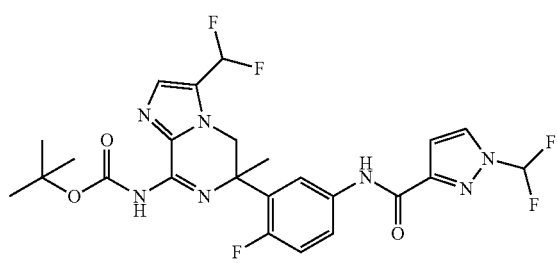 [SMILES: CC(C)(C)OC(=O)NC1=NC(C)(c2cc(NC(=O)c3ccn(C(F)F)n3)ccc2F)Cn2c(C(F)F)cnc21]

From (R)-tert-butyl [6-(5-amino-2-fluorophenyl)-3-(difluoromethyl)-6-methyl-5,6-dihydroimidazo[1,2-a]pyrazin-8-yl]carbamate and 1-difluoromethyl-1H-pyrazole-3-carboxylic acid.

B. Preparation of the Final Compounds

Example B1

Preparation of rac-6-methyl-6-(3-pyrimidin-5-yl-phenyl)-5,6-dihydro-imidazo[1,2-a]-pyrazin-8-ylamine

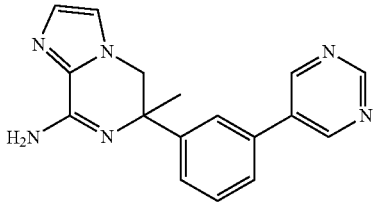 [SMILES: CC1(c2cccc(-c3cncnc3)c2)Cn2ccnc2C(N)=N1]

Tetrakis(triphenylphosphine)palladium(0) (0.027 g, 0.023 mmol) was added to a stirred suspension of rac-6-(3-bromophenyl)-6-methyl-5,6-dihydro-imidazo[1,2-a]pyrazin-8-ylamine (0.14 g, 0.46 mmol), pyrimidine-5-boronic acid (0.17 g, 1.38 mmol) and potassium carbonate (0.19 g, 1.38 mmol) in 1,4-dioxane (4 mL) and ethanol (0.4 mL) at room temperature under nitrogen. The mixture was stirred at 150° C. for 30 minutes under microwave irradiation. The mixture was diluted with water and extracted with DCM. The organic layer was separated, dried (MgSO$_4$), filtered and the solvent was evaporated in vacuo. The crude product was purified by flash column chromatography (silica gel; 7 M solution of ammonia in MeOH in DCM 0/100 to 3/97). The desired fractions were collected and concentrated in vacuo to yield rac-6-methyl-6-(3-pyrimidin-5-yl-phenyl)-5,6-dihydro-imidazo[1,2-a]pyrazin-8-ylamine (0.078 g, 56% yield) as a white solid.

Example B2

Preparation of rac-6-[3-(5-methoxy-pyridin-3-yl)-phenyl]-6-methyl-5,6-dihydro-imidazo[1,2-a]pyrazin-8-ylamine

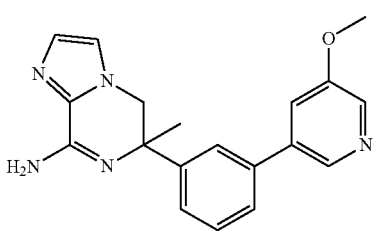 [SMILES: COc1cncc(-c2cccc(C3(C)Cn4ccnc4C(N)=N3)c2)c1]

Tetrakis(triphenylphosphine)palladium(0) (0.027 g, 0.023 mmol) was added to a stirred suspension of rac-6-(3-bromophenyl)-6-methyl-5,6-dihydro-imidazo[1,2-a]pyrazin-8-ylamine (0.14 g, 0.46 mmol), 5-methoxy-3-pyridinyl boronic acid (0.21 g, 1.38 mmol) and potassium carbonate (0.19 g, 1.38 mmol) in 1,4-dioxane (4 mL) and ethanol (0.4 mL) at room temperature under nitrogen. The mixture was stirred at 150° C. for 30 minutes under microwave irradiation. The mixture was diluted with water and extracted with DCM. The organic layer was separated, dried (MgSO$_4$), filtered and the solvents evaporated in vacuo. The crude product was purified by flash column chromatography (silica gel; 7 M solution of ammonia in MeOH in DCM 0/100 to 3/97). The desired fractions were collected and concentrated in vacuo to yield rac 6-[3-(5-methoxy-pyridin-3-yl)-phenyl]-6-methyl-5,6-dihydro-imidazo[1,2-a]pyrazin-8-ylamine (0.080 g, 52% yield) as a white solid.

Example B3

Preparation of rac-6-(3',5'-dichloro-biphenyl-3-yl)-6-methyl-5,6-dihydro-imidazo-[1,2-a]pyrazin-8-ylamine

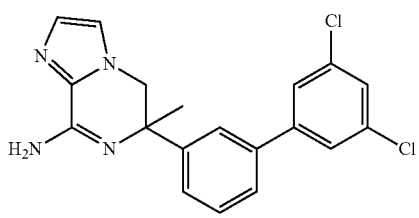 [SMILES: CC1(c2cccc(-c3cc(Cl)cc(Cl)c3)c2)Cn2ccnc2C(N)=N1]

Tetrakis(triphenylphosphine)palladium(0) (0.029 g, 0.025 mmol) was added to a stirred suspension of rac-6-(3-bromophenyl)-6-methyl-5,6-dihydro-imidazo[1,2-a]pyrazin-8-ylamine (0.15 g, 0.5 mmol), 3,5-dichlorophenylboronic acid (0.11 g, 0.6 mmol) and potassium carbonate (0.21 g, 1.5 mmol) in 1,4-dioxane (4 mL) and ethanol (0.4 mL) at room temperature under nitrogen. The mixture was stirred at 60° C. for 18 h. Then the mixture was diluted with water and extracted with DCM. The organic layer was separated, dried (MgSO$_4$), filtered and the solvent was evaporated in vacuo. The crude product was purified by flash column chromatography (silica gel; 7 M solution of ammonia in MeOH in DCM 0/100 to 3/97 and then EtOAc/MeOH 0/100 to 10/90). The desired fractions were collected and concentrated in vacuo to yield rac-6-(3',5'-dichloro-biphenyl-3-yl)-6-methyl-5,6-dihydro-imidazo[1,2-a]pyrazin-8-ylamine (0.114 g, 61% yield) as a white solid.

Example B4

Preparation of (R)-6-methyl-6-(3-pyrimidin-5-yl-phenyl)-5,6-dihydro-imidazo[1,2-a]-pyrazin-8-ylamine

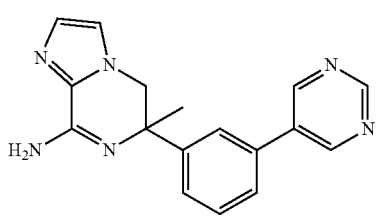 [SMILES: CC1(c2cccc(-c3cncnc3)c2)Cn2ccnc2C(N)=N1]

Tetrakis(triphenylphosphine)palladium(0) (0.038 g, 0.033 mmol) was added to a stirred suspension of (R)-6-(3-bromophenyl)-6-methyl-5,6-dihydro-imidazo[1,2-a]pyrazin-8-ylamine (0.20 g, 0.66 mmol), pyrimidine-5-boronic acid (0.24 g, 1.97 mmol) and potassium carbonate (0.27 g, 1.97 mmol) in 1,4-dioxane (4 mL) and ethanol (0.4 mL) at room temperature under nitrogen. The mixture was stirred at 150° C. for 30 minutes under microwave irradiation. The mixture was diluted with water and extracted with DCM. The organic layer was separated, dried (MgSO$_4$), filtered and the solvent was evaporated in vacuo. The crude product was purified by flash column chromatography (silica gel; 7 M solution of ammonia in MeOH in DCM 0/100 to 3/97). The desired fractions were collected and concentrated in vacuo to yield (R)-6-methyl-6-(3-pyrimidin-5-yl-phenyl)-5,6-dihydro-imidazo[1,2-a]pyrazin-8-ylamine (0.112 g, 56% yield) as a white solid.

Example B5

Preparation of (R)-6-(3',5'-dichloro-biphenyl-3-yl)-6-methyl-5,6-dihydro-imidazo-[1,2-a]pyrazin-8-ylamine

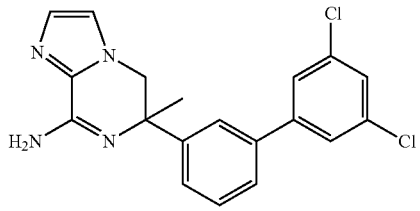 [SMILES: CC1(c2cccc(-c3cc(Cl)cc(Cl)c3)c2)Cn2ccnc2C(N)=N1]

Tetrakis(triphenylphosphine)palladium(0) (0.028 g, 0.025 mmol) was added to a stirred suspension of (R)-6-(3-bromo-phenyl)-6-methyl-5,6-dihydro-imidazo[1,2-a]pyrazin-8-ylamine (0.15 g, 0.5 mmol), 3,5-dichlorophenylboronic acid (0.11 g, 0.6 mmol) and potassium carbonate (0.20 g, 1.5 mmol) in 1,4-dioxane (4 mL) and ethanol (0.4 mL) at room temperature under nitrogen. The mixture was stirred at 60° C. for 18 h. The mixture was diluted with water and extracted with DCM. The organic layer was separated, dried (MgSO$_4$), filtered and the solvent was evaporated in vacuo. The crude product was purified by flash column chromatography (silica gel; 7 M solution of ammonia in MeOH in DCM 0/100 to 3/97 and then EtOAc/MeOH 0/100 to 10/90). The desired fractions were collected and concentrated in vacuo to yield (R)-6-(3',5'-dichloro-biphenyl-3-yl)-6-methyl-5,6-dihydro-imidazo[1,2-a]pyrazin-8-ylamine (0.92 g, 50% yield) as a white solid.

Example B6

Preparation of rac-5-chloro-pyridine-2-carboxylic acid [3-(8-amino-6-methyl-5,6-dihydro-imidazo[1,2-a]pyrazin-6-yl)-phenyl]-amide

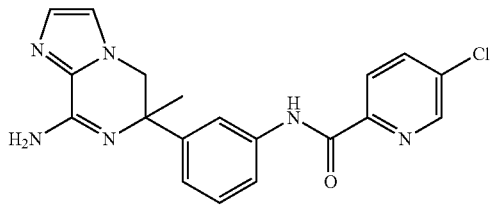 [SMILES: CC1(c2cccc(NC(=O)c3ccc(Cl)cn3)c2)Cn2ccnc2C(N)=N1]

5-Chloro-2-pyridinecarboxylic acid (108 mg, 0.68 mmol) was added to a solution of 4-(4,6-dimethoxy-1,3,5-triazin-2-yl)-4-methylmorpholinium chloride (206 mg, 0.75 mmol) in MeOH (3 mL). The mixture was stirred at room temperature for 5 minutes. The mixture was cooled to 0° C. and a solution of rac-6-(3-amino-phenyl)-6-methyl-5,6-dihydro-imidazo[1,2-a]pyrazin-8-ylamine (150 mg, 0.62 mmol) in MeOH (3 mL) was added. The mixture was warmed to room temperature and stirred for 3 hours. The mixture was treated with sat. Na$_2$CO$_3$ and water and extracted with DCM. The organic layer was separated, dried (MgSO$_4$), filtered and concentrated in vacuo. The crude product was purified by flash column chromatography (silica; 7N NH$_3$ in MeOH in DCM 0/100 to 2/98). The desired fractions were collected and the solvent was evaporated in vacuo to yield rac-5-chloro-pyridine-2-carboxylic acid [3-(8-amino-6-methyl-5,6-dihydro-imidazo[1,2-a]pyrazin-6-yl)-phenyl]-amide (0.145 g, 61% yield) as a white solid.

Example B7

Preparation of (R)-6-(2-fluoro-5-pyrimidin-5-yl-phenyl)-6-methyl-5,6-dihydro-imidazo[1,2-a]pyrazin-8-ylamine

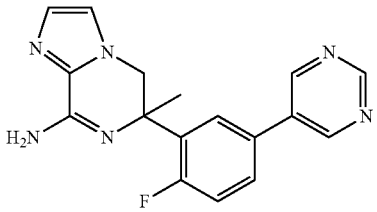 [SMILES: CC1(c2cc(-c3cncnc3)ccc2F)Cn2ccnc2C(N)=N1]

Tetrakis(triphenylphosphine)palladium(0) (0.009 g, 0.0077 mmol) was added to a stirred suspension of (R)-6-(5-bromo-2-fluoro-phenyl)-6-methyl-5,6-dihydro-imidazo[1,2-a]pyrazin-8-ylamine (0.05 g, 0.15 mmol), pyrimidine-5-boronic acid (0.06 g, 0.46 mmol) and potassium carbonate (0.06 g, 0.46 mmol) in 1,4-dioxane (2 mL) and ethanol (0.2 mL) at room temperature under nitrogen. The mixture was stirred at 150° C. for 30 minutes under microwave irradiation. The mixture was diluted with water and extracted with DCM. The organic layer was separated, dried (MgSO$_4$), filtered and the solvent was evaporated in vacuo. The crude product was purified by flash column chromatography (silica gel; 7 M solution of ammonia in MeOH in DCM 0/100 to 3/97). The desired fractions were collected and concentrated in vacuo. The residue was triturated with diethyl ether, filtered and dried in vacuo to yield (R)-6-(2-fluoro-5-pyrimidin-5-yl-phenyl)-6-methyl-5,6-dihydro-imidazo[1,2-a]-pyrazin-8-ylamine (0.015 g, 30% yield) as a white solid.

Example B8

Preparation of (R)-5-chloro-pyridine-2-carboxylic acid [3-(8-amino-6-methyl-5,6-dihydro-imidazo[1,2-a]pyrazin-6-yl)-4-fluoro-phenyl]-amide

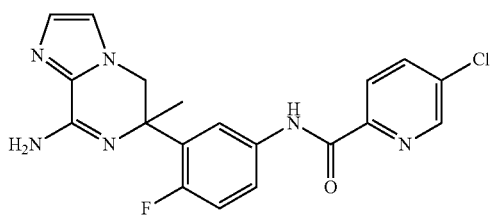 [SMILES: CC1(c2cc(NC(=O)c3ccc(Cl)cn3)ccc2F)Cn2ccnc2C(N)=N1]

5-Chloro-2-pyridinecarboxylic acid (0.07 mg, 0.45 mmol) was added to a solution of 4-(4,6-dimethoxy-1,3,5-triazin-2-yl)-4-methylmorpholinium chloride (134 mg, 0.49 mmol) in MeOH (3 mL). The mixture was stirred at room temperature for 5 minutes. The mixture was cooled to 0° C. and a solution of (R)-6-(5-amino-2-fluoro-phenyl)-6-methyl-5,6-dihydro-imidazo[1,2-a]pyrazin-8-ylamine (105 mg, 0.4 mmol) in MeOH (3 mL) was added. The mixture was warmed to room temperature and stirred for 3 hours. The mixture was treated with sat. Na$_2$CO$_3$ and water and extracted with DCM. The organic layer was separated, dried (Na$_2$SO$_4$), filtered and concentrated in vacuo. The crude product was purified by flash column chromatography (silica; 7N NH$_3$ in MeOH in DCM 0/100 to 2/98). The desired fractions were collected and the solvent was evaporated in vacuo. The residue was triturated with diethyl ether, filtered and dried in vacuo to yield (R)-5-chloro-pyridine-2-carboxylic acid [3-(8-amino-6-methyl-5,6-dihydro-imidazo[1,2-a]pyrazin-6-yl)-4-fluoro-phenyl]-amide (0.068 g, 42% yield) as a white solid.

Example B9

Preparation of (R)-5-methoxy-pyrazine-2-carboxylic acid [3-(8-amino-6-methyl-5,6-dihydro-imidazo[1,2-a]pyrazin-6-yl)-4-fluoro-phenyl]-amide

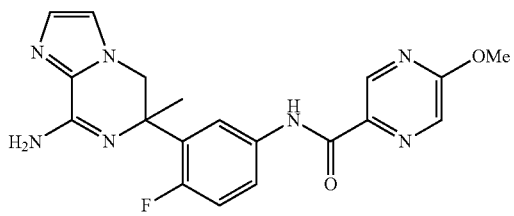 [SMILES: COc1cnc(C(=O)Nc2ccc(F)c(C3(C)Cn4ccnc4C(N)=N3)c2)cn1]

5-Methoxy-pyrazine-2-carboxylic acid (0.105 mg, 0.68 mmol) was added to a solution of 4-(4,6-dimethoxy-1,3,5-triazin-2-yl)-4-methylmorpholinium chloride (205 mg, 0.74 mmol) in MeOH (3 mL). The mixture was stirred at room temperature for 5 minutes. The mixture was cooled to 0° C. and a solution of (R)-6-(5-amino-2-fluoro-phenyl)-6-methyl-5,6-dihydro-imidazo[1,2-a]pyrazin-8-ylamine (105 mg, 0.4 mmol) in MeOH (3 mL) was added. The mixture was warmed to room temperature and stirred for 18 hours. The mixture was treated with sat. Na$_2$CO$_3$ and water and extracted with DCM. The organic layer was separated, dried (Na$_2$SO$_4$), filtered and concentrated in vacuo. The crude product was purified by flash column chromatography (silica; 7N NH$_3$ in MeOH in DCM 0/100 to 3/97). The desired fractions were collected and the solvents evaporated in vacuo. The residue was triturated with DIPE, filtered and dried in vacuo to yield (R)-5-methoxy-pyrazine-2-carboxylic acid [3-(8-amino-6-methyl-5,6-dihydro-imidazo[1,2-a]pyrazin-6-yl)-4-fluoro-phenyl]-amide (0.100 g, 41% yield) as a yellow solid.

Example B10

Preparation of (R)-5-fluoro-pyridine-2-carboxylic acid [3-(8-amino-6-methyl-5,6-dihydro-imidazo[1,2-a]pyrazin-6-yl)-4-fluoro-phenyl]-amide

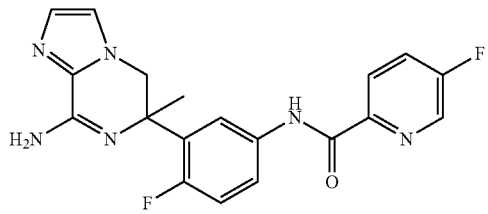 [SMILES: CC1(c2cc(NC(=O)c3ccc(F)cn3)ccc2F)Cn2ccnc2C(N)=N1]

5-Fluoro-2-pyridinecarboxylic acid (0.10 mg, 0.68 mmol) was added to a solution of 4-(4,6-dimethoxy-1,3,5-triazin-2-yl)-4-methylmorpholinium chloride (205 mg, 0.74 mmol) in MeOH (3 mL). The mixture was stirred at room temperature for 5 minutes. The mixture was cooled to 0° C. and a solution of (R)-6-(5-amino-2-fluoro-phenyl)-6-methyl-5,6-dihydro-imidazo[1,2-a]pyrazin-8-ylamine (160 mg, 0.62 mmol) in MeOH (3 mL) was added. The mixture was warmed to room temperature and stirred for 18 hours. The mixture was treated with sat. Na$_2$CO$_3$ and water and extracted with DCM. The organic layer was separated, dried (Na$_2$SO$_4$), filtered and concentrated in vacuo. The crude product was purified by flash column chromatography (silica; 7N NH$_3$ in MeOH in DCM 0/100 to 3/97). The desired fractions were collected and the solvents evaporated in vacuo. The residue was triturated with diethyl ether, filtered and dried in vacuo to yield (R)-5-fluoro-pyridine-2-carboxylic acid [3-(8-amino-6-methyl-5,6-dihydro-imidazo[1,2-a]pyrazin-6-yl)-4-fluoro-phenyl]-amide (0.088 g, 37% yield) as a white solid.

Example B11

Preparation of (R)-6-(2,4-difluoro-5-pyrimidin-5-yl-phenyl)-6-methyl-5,6-dihydro-imidazo[1,2-a]pyrazin-8-ylamine

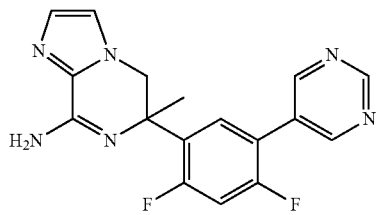 [SMILES: CC1(c2cc(-c3cncnc3)c(F)cc2F)Cn2ccnc2C(N)=N1]

Tetrakis(triphenylphosphine)palladium(0) (0.051 g, 0.044 mmol) was added to a stirred suspension of (R)-6-(5-bromo-2,4-difluoro-phenyl)-6-methyl-5,6-dihydro-imidazo[1,2-a]pyrazin-8-ylamine (0.30 g, 0.88 mmol), pyrimidine-5-boronic acid (0.33 g, 2.64 mmol) and potassium carbonate (0.365 g, 2.64 mmol) in 1,4-dioxane (4 mL) and ethanol (0.4 mL) at room temperature under nitrogen. The mixture was stirred at 150° C. for 30 minutes under microwave irradiation. The mixture was diluted with water and extracted with DCM. The organic layer was separated, dried (MgSO$_4$), filtered and the solvent was evaporated in vacuo. The crude product was purified by flash column chromatography (silica gel; 7 M solution of ammonia in MeOH in DCM 0/100 to 3/97 and then MeOH in EtOAc 20/80). The desired fractions were collected and concentrated in vacuo. The product was triturated with diethyl ether, filtered and dried in vacuo to yield (R)-6-(2,4-difluoro-5-pyrimidin-5-yl-phenyl)-6-methyl-5,6-dihydro-imidazo[1,2-a]pyrazin-8-ylamine (0.110 g, 37% yield) as a white solid.

Example B12

Preparation of (R)-6-[5-(5-chloro-pyridin-3-yl)-2,4-difluoro-phenyl)-6-methyl-5,6-dihydro-imidazo[1,2-a]pyrazin-8-ylamine

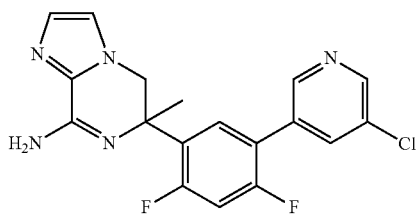 [SMILES: CC1(c2cc(-c3cncc(Cl)c3)c(F)cc2F)Cn2ccnc2C(N)=N1]

Tetrakis(triphenylphosphine)palladium(0) (0.034 g, 0.029 mmol) was added to a stirred suspension of (R)-6-(5-bromo-2,4-difluoro-phenyl)-6-methyl-5,6-dihydro-imidazo[1,2-a]pyrazin-8-ylamine (0.20 g, 0.59 mmol), 5-chloropyridine-3-boronic acid (0.138 g, 0.88 mmol) and potassium carbonate (0.243 g, 1.76 mmol) in 1,4-dioxane (6 mL) and ethanol (0.6 mL) at room temperature under nitrogen. The mixture was stirred at 80° C. for 24 h. Then the mixture was diluted with water and extracted with DCM. The organic layer was separated, dried (MgSO$_4$), filtered and the solvents evaporated in vacuo. The crude product was purified by flash column chromatography (silica gel; 7 M solution of ammonia in MeOH in DCM 0/100 to 3/97). The desired fractions were collected and concentrated in vacuo. The product was triturated with DIPE, filtered and dried in vacuo to yield (R)-6-[5-(5-chloro-pyridin-3-yl)-2,4-difluoro-phenyl)-6-methyl-5,6-dihydro-imidazo[1,2-a]pyrazin-8-ylamine (0.125 g, 57% yield) as a white solid.

Example B13

Preparation of (R)—N-{3-[8-amino-2-cyano-6-methyl-5,6-dihydroimidazo[1,2-a]-pyrazin-6-yl]-4-fluorophenyl}-5-fluoropyridine-2-carboxamide

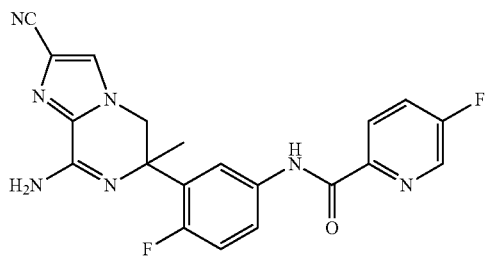 [SMILES: CC1(c2cc(NC(=O)c3ccc(F)cn3)ccc2F)Cn2cc(C#N)nc2C(N)=N1]

Tetrakis(triphenylphosphine)palladium(0) (17 mg, 0.015 mmol) was added to a stirred suspension of (R)-tert-butyl [2-bromo-6-(2-fluoro-5-{[(5-fluoropyridin-2-yl)carbonyl]amino}phenyl)-6-methyl-5,6-dihydroimidazo[1,2-a]pyrazin-8-yl]carbamate (0.085 g, 0.15 mmol) and zinc cyanide (0.020 g, 0.17 mmol) in DMF (1.52 mL). The mixture was stirred at 110° C. for 16 hours. The mixture was taken up in EtOAc and washed with water. The organic layer was separated, dried (MgSO$_4$), filtered and the solvent was evaporated in vacuo. The residue was treated with sodium cyanide (0.015 g, 0.3 mmol), potassium iodide (0.025 g, 0.15 mmol), copper iodide (0.036 g, 0.19 mmol) and N,N'-dimethylethylenediamine (0.029 mL, 0.26 mmol) in toluene (2 mL). The reaction mixture was stirred at 110° C. for 5 hours. The solvent was evaporated in vacuo, the residue was diluted with water and extracted with EtOAc. The organic layer was separated, dried (MgSO$_4$), filtered and the solvent was evaporated in vacuo. The crude product was purified by flash column chromatography (silica; 7 M solution of ammonia in MeOH in DCM 0/100 to 10/90). The desired fractions were collected and concentrated in vacuo to yield (R)—N-{3-[8-amino-2-cyano-6-methyl-5,6-dihydroimidazo[1,2-a]pyrazin-6-yl]-4-fluorophenyl}-5-fluoropyridine-2-carboxamide (7 mg, 11% yield) as an oil.

Example B14

Preparation of (R)—N-{3-[8-amino-2-chloro-3-cyano-6-methyl-5,6-dihydroimidazo-[1,2-a]pyrazin-6-yl]-4-fluorophenyl}-5-fluoropyridine-2-carboxamide (compound 59)

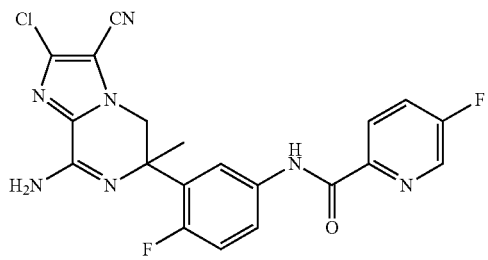 [SMILES: CC1(c2cc(NC(=O)c3ccc(F)cn3)ccc2F)Cn2c(C#N)cnc2C(N)=N1]

Trifluoroacetic acid (2.5 mL, 32.67 mmol) was added to a stirred solution of (R)-tert-butyl [2-chloro-3-cyano-6-(2-fluoro-5-{[(5-fluoropyridin-2-yl)carbonyl]amino}phenyl)-

6-methyl-5,6-dihydroimidazo[1,2-a]pyrazin-8-yl]carbamate (0.040 g, 0.074 mmol) in DCM (5 mL). The mixture was stirred at room temperature for 30 minutes. The solvent was evaporated in vacuo and the residue was dissolved in DCM and washed with sat. NaHCO$_3$. The organic layer was separated, dried (MgSO$_4$), filtered and the solvent was evaporated in vacuo. The residue was triturated with a 1/1 mixture of heptane/DIPE to yield (R)—N-{3-[8-amino-2-chloro-3-cyano-6-methyl-5,6-dihydroimidazo[1,2-a]pyrazin-6-yl]-4-fluorophenyl}-5-fluoropyridine-2-carboxamide (26 mg, 80% yield).

Example B15

Preparation of (R)—N-{3-[8-amino-3-cyano-6-methyl-5,6-dihydroimidazo[1,2-a]pyrazin-6-yl]-4-fluorophenyl}-5-fluoropyridine-2-carboxamide (compound 66)

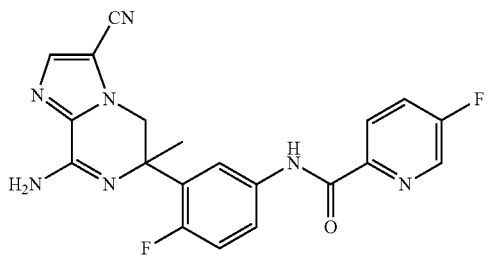

Trifluoroacetic acid (1 mL, 13.06 mmol) was added to a stirred solution of (R)-tert-butyl [3-cyano-6-(2-fluoro-5-{[(5-fluoropyridin-2-yl)carbonyl]amino}phenyl)-6-methyl-5,6-dihydroimidazo[1,2-a]pyrazin-8-yl]carbamate (0.056 g, 0.11 mmol) in DCM (2 mL). The mixture was stirred at room temperature for 2 hours. The solvent was evaporated in vacuo and the residue was dissolved in DCM and washed with sat. NaHCO$_3$. The organic layer was separated, dried (MgSO$_4$), filtered and the solvent was evaporated in vacuo. The residue was triturated with a 1/1 mixture of heptane/DIPE to yield (R)—N-{3-[8-amino-3-cyano-6-methyl-5,6-dihydroimidazo[1,2-a]pyrazin-6-yl]-4-fluorophenyl}-5-fluoropyridine-2-carboxamide (35 mg, 78% yield).

Example B16

Preparation of (R)—N-{3-[8-amino-2-chloro-3-chloro-6-methyl-5,6-dihydroimidazo[1,2-a]pyrazin-6-yl]-4-fluorophenyl}-5-fluoropyridine-2-carboxamide (compound 72)

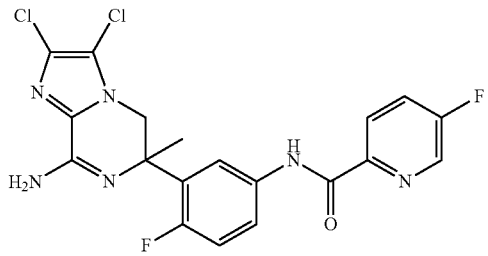

Trifluoroacetic acid (0.34 mL, 5.01 mmol) was added to a stirred solution of (R)-tert-butyl [2-chloro-3-chloro-6-(2-fluoro-5-{[(5-fluoropyridin-2-yl)carbonyl]amino}phenyl)-6-methyl-5,6-dihydroimidazo[1,2-a]pyrazin-8-yl]carbamate (0.044 g, 0.080 mmol) in DCM (0.77 mL). The mixture was stirred at room temperature for 30 minutes. The solvent was evaporated in vacuo and the residue was dissolved in DCM and washed with sat. NaHCO$_3$. The organic layer was separated, dried (MgSO$_4$), filtered and the solvent was evaporated in vacuo. The residue was triturated with a 1/1 mixture of heptane/DIPE to yield (R)—N-{3-[8-amino-2-chloro-3-chloro-6-methyl-5,6-dihydroimidazo[1,2-a]pyrazin-6-yl]-4-fluorophenyl}-5-fluoropyridine-2-carboxamide (14 mg, 39% yield).

Example B17

Preparation of (R)—N-{3-[8-amino-3-difluoromethyl-6-methyl-5,6-dihydroimidazo[1,2-a]pyrazin-6-yl]-4-fluorophenyl}-5-fluoropyridine-2-carboxamide (compound 77)

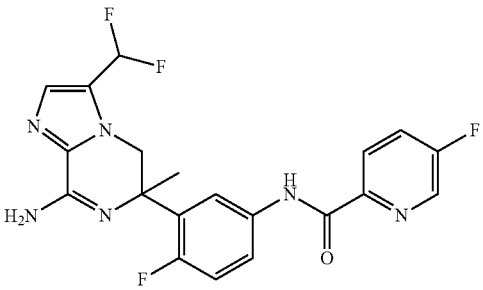 [SMILES: CC1(c2cc(NC(=O)c3ccc(F)cn3)ccc2F)Cn2c(C(F)F)cnc2C(N)=N1]

Trifluoroacetic acid (0.48 mL, 6.25 mmol) was added to a stirred solution of (R)-tert-butyl [3-difluoromethyl-6-(2-fluoro-5-{[(5-fluoropyridin-2-yl)carbonyl]amino}phenyl)-6-methyl-5,6-dihydroimidazo[1,2-a]pyrazin-8-yl]carbamate (0.053 g, 0.09 mmol) in DCM (0.96 mL). The mixture was stirred at room temperature for 30 minutes. The solvent was evaporated in vacuo and the residue was dissolved in DCM and washed with sat. NaHCO$_3$. The organic layer was separated, dried (MgSO$_4$), filtered and the solvent was evaporated in vacuo. The residue was triturated with a 1/1 mixture of heptane/DIPE to yield (R)—N-{3-[8-amino-3-difluoromethyl-6-methyl-5,6-dihydroimidazo[1,2-a]pyrazin-6-yl]-4-fluorophenyl}-5-fluoropyridine-2-carboxamide (36 mg, 84% yield).

Example B18

Preparation of (R)-[2-cyano-6-(2-fluoro-5-{[(5-methoxy-pyrazine)-carbonyl]amino}-phenyl)-6-methyl-5,6-dihydroimidazo[1,2-a]pyrazin-8-yl]-carbamate compound 79

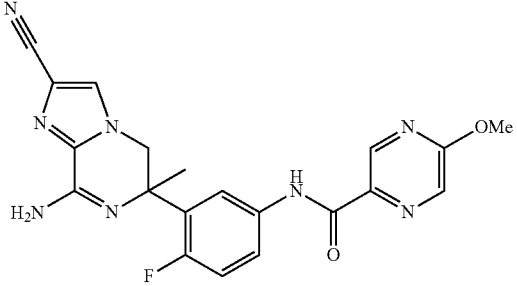 [SMILES: COc1cnc(C(=O)Nc2ccc(F)c(C3(C)Cn4cc(C#N)nc4C(N)=N3)c2)cn1]

5-Methoxy-pyrazine-2-carboxylic acid (0.044 mg, 0.28 mmol) was added to a solution of 4-(4,6-dimethoxy-1,3,5-triazin-2-yl)-4-methylmorpholinium chloride (86 mg, 0.31 mmol) in MeOH (3 mL). The mixture was stirred at room temperature for 5 minutes. The mixture was cooled to 0° C. and a solution of (R)-6-(5-amino-2-fluoro-phenyl)-2cyano-6-methyl-5,6-dihydro-imidazo[1,2-a]pyrazin-8-ylamine (80 mg, 0.28 mmol) in MeOH (3 mL) was added. The mixture was warmed to room temperature and stirred for 18 hours. The mixture was treated with sat. Na₂CO₃ and water and extracted with DCM. The organic layer was separated, dried (Na₂SO₄), filtered and concentrated in vacuo. The crude product was purified by flash column chromatography (silica; 7N NH₃ in MeOH in DCM 0/100 to 3/97). The desired fractions were collected and the solvents evaporated in vacuo. The residue was triturated with DIPE, filtered and dried in vacuo to (R)-[2-cyano-6-(2-fluoro-5-{[(5-methoxy-pyrazine)-carbonyl]amino}-phenyl)-6-methyl-5,6-dihydroimidazo[1,2-a]pyrazin-8-yl]carbamate (0.013 g, 11% yield) as a yellow solid.

Compounds 1 to 80 in Tables 1-2 list the compounds that were prepared by analogy to the above Examples. When no salt form is indicated, the compound was obtained as a free base. 'Ex. No.' refers to the Example number according to which the compound was synthesized. 'Co. No.' means compound number.

TABLE 1

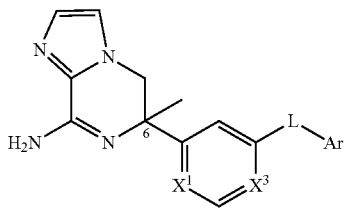

| Co. No. | Ex. No. | $X^1$ | $X^3$ | —L—Ar | $C_6$-stereo-chemistry |
|---|---|---|---|---|---|
| 1 | B1 | CH | CH | pyrimidin-5-yl | RS |
| 2 | B2 | CH | CH | 5-methoxy-pyridin-3-yl | RS |
| 3 | B3 | CH | CH | 3,5-dichlorophenyl | RS |
| 4 | B4 | CH | CH | pyrimidin-5-yl | R |
| 5 | B5 | CH | CH | 3,5-dichlorophenyl | R |
| 6 | B6 | CH | CH | 5-chloro-pyridine-2-carboxamide | RS |
| 7 | B7 | CF | CH | pyrimidin-5-yl | *R |
| 8 | B8 | CF | CH | 5-chloro-pyridine-2-carboxamide | *R |
| 9 | B9 | CF | CH | 5-methoxy-pyrazine-2-carboxamide | *R |
| 10 | B10 | CF | CH | 5-fluoro-pyridine-2-carboxamide | *R |
| 11 | B11 | CF | CF | pyrimidin-5-yl | *R |
| 12 | B12 | CF | CF | 5-chloro-pyridin-3-yl | *R |
| 13 | B8 | CH | CH | 5-cyano-pyridine-2-carboxamide | R |
| 14 | B9 | CH | CH | 5-chloro-pyridine-2-carboxamide | R |

TABLE 1-continued

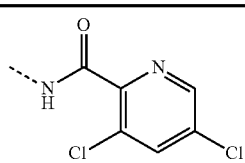

| Co. No. | Ex. No. | X¹ | X³ | —L—Ar | C₆-stereochemistry |
|---|---|---|---|---|---|
| 15 | B8 | CH | CH | (3,5-dichloropyridin-2-yl)carboxamide | R |

TABLE 1-continued

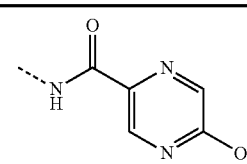

| Co. No. | Ex. No. | X¹ | X³ | —L—Ar | C₆-stereochemistry |
|---|---|---|---|---|---|
| 16 | B8 | CH | CH | (5-methoxypyrazin-2-yl)carboxamide | R |

TABLE 2

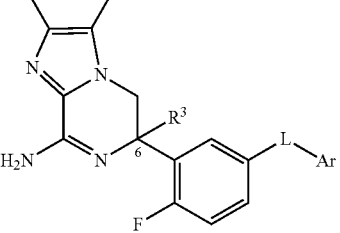

| Co. No. | Ex. No. | R¹ | R² | R³ | —L—Ar | C₆-stereochemistry |
|---|---|---|---|---|---|---|
| 17 | B9 | H | H | Me | (5-methoxypyridin-2-yl)carboxamide | R |
| 18 | B9 | H | H | Me | (5-cyanopyridin-2-yl)carboxamide | R |
| 19 | B9 | H | H | Me | (3,5-dichloropyridin-2-yl)carboxamide | R |
| 20 | B9 | H | H | Me | (3-fluoro-5-chloropyridin-2-yl)carboxamide | R |
| 21 | B9 | H | H | Me | (3-chloro-5-cyanopyridin-2-yl)carboxamide | R |

TABLE 2-continued

| Co. No. | Ex. No. | R¹ | R² | R³ | —L—Ar | C₆-stereochemistry |
|---|---|---|---|---|---|---|
| 22 | B8 | H | H | Me | N-(C=O)-pyridine-3-F,5-CN | R |
| 23 | B9 | H | H | Me | N-(C=O)-pyrazine-5-OEt | R |
| 24 | B8 | CF₃ | H | Me | N-(C=O)-pyridine-5-F | R |
| 25 | B8 | CF₃ | H | Me | N-(C=O)-pyridine-3,5-diCl | R |
| 26 | B8 | CF₃ | H | Me | N-(C=O)-pyrazine-5-OMe | R |
| 27 | B6 | H | H | CHF₂ | N-(C=O)-pyridine-5-F | RS |
| 28 | B6 | H | H | CHF₂ | N-(C=O)-pyridine-5-F | *R |
| 29 | B6 | H | H | CHF₂ | N-(C=O)-pyridine-5-F | *S |

TABLE 2-continued
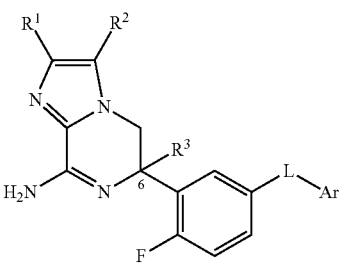
| Co. No. | Ex. No. | R¹ | R² | R³ | —L—Ar | $C_6$-stereochemistry |
|---|---|---|---|---|---|---|
| 30 | B6 | H | H | $CHF_2$ | 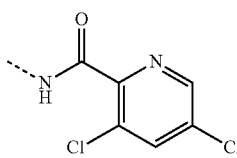 | RS |
| 31 | B6 | H | H | $CHF_2$ | 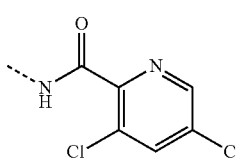 | *R |
| 32 | B6 | H | H | $CHF_2$ | 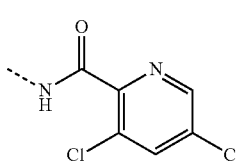 | *S |
| 33 | B6 | H | H | $CHF_2$ | 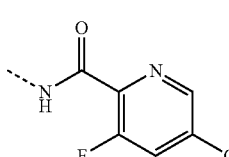 | RS |
| 34 | B6 | H | H | $CHF_2$ | 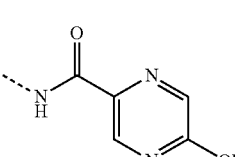 | RS |
| 35 | B6 | H | H | $CHF_2$ | 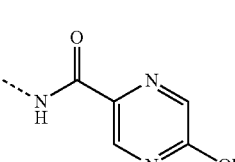 | *R |
| 36 | B6 | H | H | $CHF_2$ | 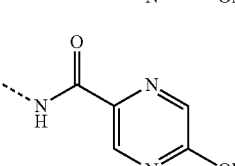 | *S |
| 37 | B8 | $CF_3$ | H | Me | 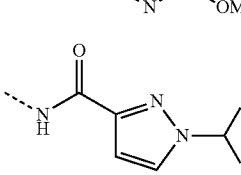 | R |

TABLE 2-continued
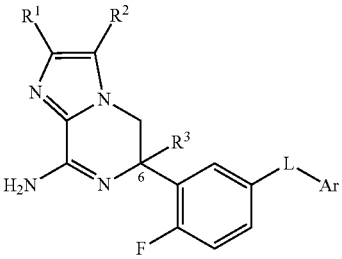
| Co. No. | Ex. No. | R¹ | R² | R³ | —L—Ar | C₆-stereochemistry |
|---|---|---|---|---|---|---|
| 38 | B8 | CF₃ | H | Me | 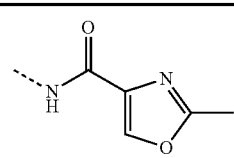 | R |
| 39 | B8 | CF₃ | H | Me | 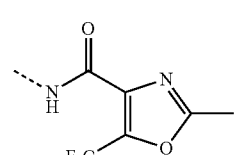 | R |
| 40 | B8 | CF₃ | H | Me | 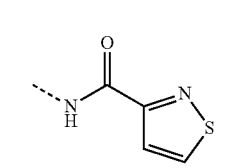 | R |
| 41 | B8 | CF₃ | H | Me | 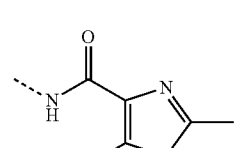 | R |
| 42 | B9 | H | H | Me | 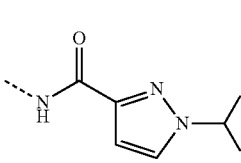 | R |
| 43 | B9 | H | H | Me | 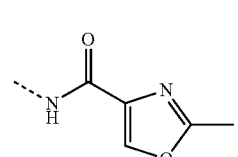 | R |
| 44 | B9 | H | H | Me | 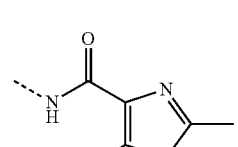 | R |
| 45 | B9 | H | H | Me | 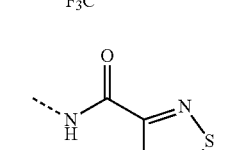 | R |

TABLE 2-continued
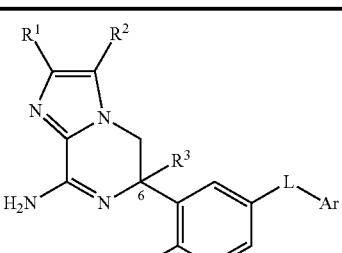
| Co. No. | Ex. No. | R¹ | R² | R³ | —L—Ar | C₆-stereochemistry |
|---|---|---|---|---|---|---|
| 46 | B9 | H | H | Me | 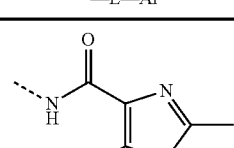 | R |
| 47 | B9 | CHF₂ | H | Me | 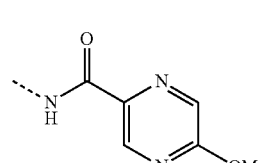 | R |
| 48 | B9 | CHF₂ | H | Me | 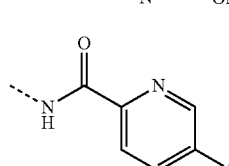 | R |
| 49 | B9 | CHF₂ | H | Me | 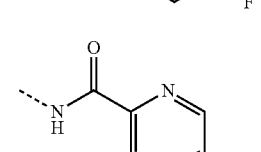 | R |
| 50 | B9 | CHF₂ | H | Me | 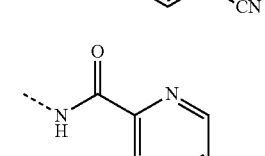 | R |
| 51 | B9 | CHF₂ | H | Me | 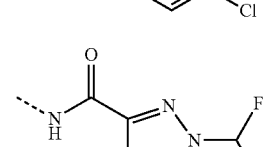 | R |
| 52 | B9 | Cl | H | Me | 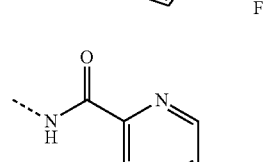 | R |
| 53 | B9 | Cl | H | Me | 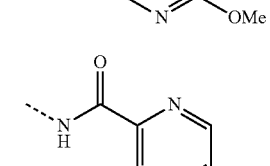 | R |

TABLE 2-continued
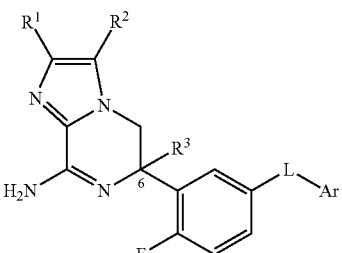
| Co. No. | Ex. No. | R¹ | R² | R³ | —L—Ar | C₆-stereochemistry |
|---|---|---|---|---|---|---|
| 54 | B9 | Br | H | Me | 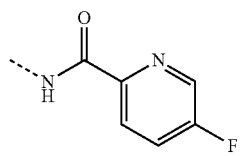 | R |
| 55 | B9 | Br | H | Me | 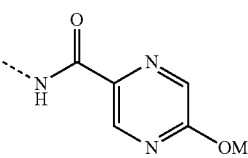 | R |
| 56 | B13 | CN | H | Me | 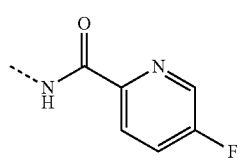 | R |
| 57 | B8 | H | Cl | Me | 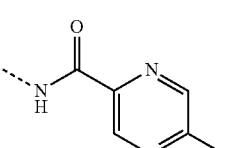 | R |
| 58 | B8 | H | Cl | Me | 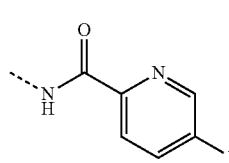 | R |
| 59 | B14 | Cl | CN | Me | 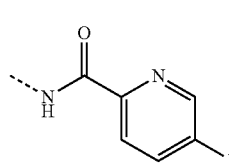 | R |
| 60 | B14 | Cl | CN | Me | 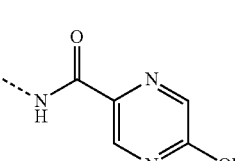 | R |
| 61 | B14 | Cl | CN | Me | 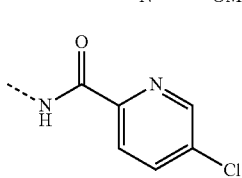 | R |

TABLE 2-continued
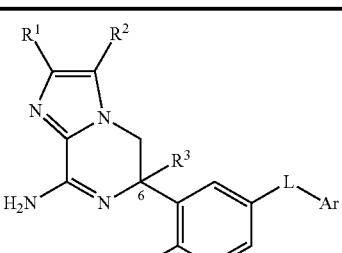
| Co. No. | Ex. No. | R¹ | R² | R³ | —L—Ar | C₆-stereochemistry |
|---|---|---|---|---|---|---|
| 62 | B14 | Cl | CN | Me | 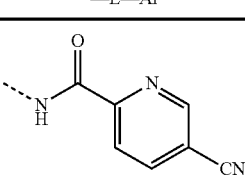 | R |
| 63 | B14 | Cl | CN | Me | 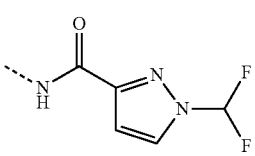 | R |
| 64 | B15 | H | CN | Me | 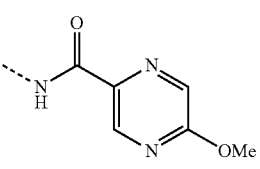 | R |
| 65 | B15 | H | CN | Me | 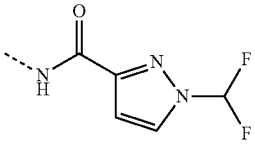 | R |
| 66 | B15 | H | CN | Me | 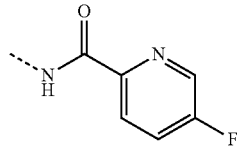 | R |
| 67 | B15 | H | CN | Me | 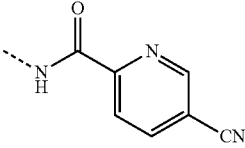 | R |
| 68 | B15 | H | CN | Me | 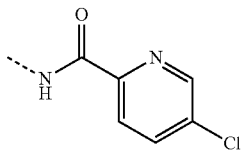 | R |
| 69 | B16 | Cl | Cl | Me | 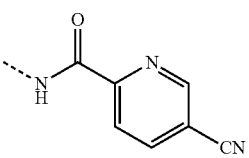 | R |

TABLE 2-continued
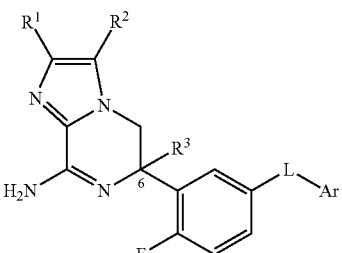
| Co. No. | Ex. No. | R¹ | R² | R³ | —L—Ar | C₆-stereochemistry |
|---|---|---|---|---|---|---|
| 70 | B16 | Cl | Cl | Me | 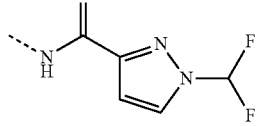 | R |
| 71 | B16 | Cl | Cl | Me | 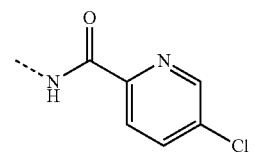 | R |
| 72 | B16 | Cl | Cl | Me | 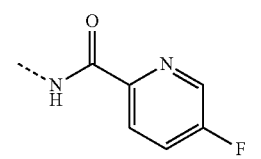 | R |
| 73 | B16 | Cl | Cl | Me | 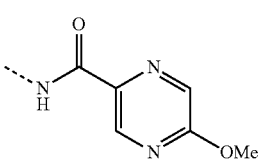 | R |
| 74 | B17 | H | CHF₂ | Me | 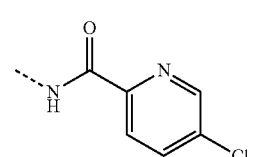 | R |
| 75 | B17 | H | CHF₂ | Me | 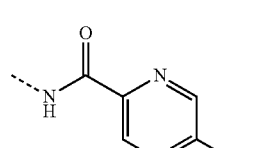 | R |
| 76 | B17 | H | CHF₂ | Me | 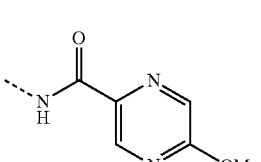 | R |
| 77 | B17 | H | CHF₂ | Me | 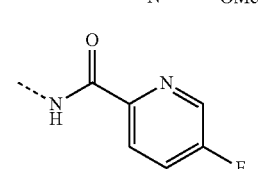 | R |

TABLE 2-continued

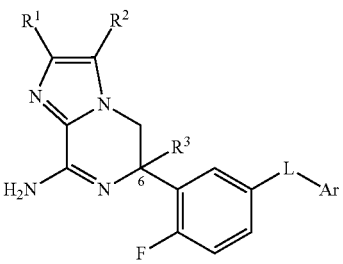

| Co. No. | Ex. No. | R¹ | R² | R³ | —L—Ar | C₆-stereochemistry |
|---|---|---|---|---|---|---|
| 78 | B17 | H | CHF₂ | Me | 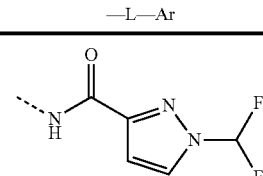 | R |
| 79 | B18 | CN | H | Me | 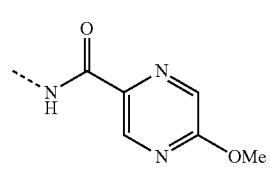 | R |
| 80 | B18 | CN | H | Me | 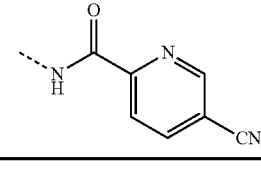 | R |

C. Analytical Part

LCMS

For (LC)MS-characterization of the compounds of the present invention, the following methods were used.

General Procedure A

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods. Flow from the column was brought to the MS spectrometer. The MS detector was configured with an electrospray ionization source. Mass spectra were acquired on a single quadrupole SQD detector by scanning from 100 to 1000 in 0.1 second using an inter-channel delay of 0.08 second. The capillary needle voltage was 3.0 kV. The cone voltage was 25 V for positive ionization mode and 30 V for negative ionization mode. Nitrogen was used as the nebulizer gas. The source temperature was maintained at 140° C. Data acquisition was performed with MassLynx-Openlynx software.

Method 1

In addition to the general procedure: Reversed phase UPLC was carried out on a BEH-C18 column (1.7 μm, 2.1×50 mm) from Waters, with a flow rate of 1.0 ml/min, at 50° C. without split to the MS detector. The gradient conditions used are: 95% A (6.5 mM ammonium acetate in H₂O/acetonitrile 95/5), 5% B (acetonitrile), to 40% A, 60% B in 3.8 minutes, to 5% A, 95% B in 4.6 minutes, kept till 5.0 minutes. Injection volume 2 μl.

Method 2

In addition to the general procedure: Reversed phase UPLC was carried out on a RRHD Eclipse Plus-C18 (1.8 μm, 2.1×50 mm) from Agilent, with a flow rate of 1.0 ml/min, at 50° C. without split to the MS detector. The gradient conditions used are: 95% A (6.5 mM ammonium acetate in H₂O/acetonitrile 95/5), 5% B (acetonitrile), to 40% A, 60% B in 7.0 minutes, to 5% A, 95% B in 8.6 minutes, kept till 9.0 minutes. Injection volume 2.0 μl.

Method 3

Same RP gradient used as in method 1 using a RRHD Eclipse Plus-C18 (1.8 μm, 2.1×50 mm) column, from Agilent, instead of BEH column.

General Procedure B

The HPLC measurement was performed using an HP 1100 (Agilent Technologies) system comprising a binary pump with degasser, an autosampler, a column oven, a diode-array detector (DAD) and a column as specified in the respective methods below. Flow from the column was split to the MS spectrometer. The MS detector (either SQD or TOF) was configured with an electrospray ionization source. The source temperature was maintained at 140° C. Nitrogen was used as the nebulizer gas. Data acquisition was performed with MassLynx-Openlynx software.

B1: Mass spectra were acquired on a single quadrupole SQD detector by scanning from 100 to 1000 in 0.1 second using an inter-channel delay of 0.08 second. The capillary needle voltage was 3.0 kV.

B2: Mass spectra were acquired on a Time of Flight (TOF) detector by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration Method 4

In addition to the general procedure B1: Reversed phase HPLC was carried out on an Eclipse Plus-C18 column (3.5 μm, 2.1×30 mm) from Agilent, with a flow rate of 1.0 ml/min, at 60° C. without split to the MS detector. The gradient conditions used are: 95% A (6.5 mM ammonium acetate in H$_2$O/acetonitrile 95/5), 5% B (mixture of acetonitrile/methanol, 1/1), to 100% B in 5.0 minutes, kept till 5.15 minutes and equilibrated to initial conditions at 5.30 minutes until 7.0 minutes. Injection volume 2 μl. The cone voltage was 20 V for positive ionization mode and 30 V for negative ionization mode.

Method 5

In addition to the general procedure B1: Reversed phase HPLC was carried out on an Eclipse Plus-C18 column (3.5 μm, 2.1×30 mm) from Agilent, with a flow rate of 1.0 ml/min, at 60° C. without split to the MS detector. The gradient conditions used are: 95% A (6.5 mM ammonium acetate in H$_2$O/acetonitrile 95/5), 5% B (acetonitrile/methanol, 1/1), kept 0.2 minutes, to 100% B in 3.0 minutes, kept till 3.15 minutes and equilibrated to initial conditions at 3.30 minutes until 5.0 minutes. Injection volume 2 μl. The cone voltage was 20 V and 50 V for positive ionization mode and 30 V for negative ionization mode.

General Procedure C

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Cone voltage was 10 V for positive ionization mode and 20 V for negative ionization mode. Nitrogen was used as the nebulizer gas. Data acquisition was performed with a Waters-Micromass MassLynx-Openlynx data system.

Method 6

In addition to the general procedure C, Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (10 mM ammonium acetate in H$_2$O/acetonitrile 95/5; mobile phase B: acetonitrile) were used to run a gradient condition from 95% A and 5% B to 5% A and 95% B in 1.3 minutes and hold for 0.7 minutes. An injection volume of 0.75 ml was used.

General Procedure D

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. Mass spectra were acquired on a Quattro detector (triple quadrupole mass spectrometer from Waters) by scanning from 100 to 1000 in 0.2 seconds using an inter-scan delay of 0.1 seconds. The capillary needle voltage was 3 kV and the source temperature was maintained at 130° C. Cone voltage was 20V for positive and negative ionization mode. Nitrogen was used as the nebulizer gas. Data acquisition was performed with MassLynx-Openlynx software (Waters).

Method 7

In addition to the general procedure D: Reversed phase UPLC was carried out on a Waters Acquity BEH (bridged ethylsiloxane/silica hybrid) Phenyl-Hexyl column (1.7 μm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 ml was used.

Melting Points

Values are either peak values or melt ranges, and are obtained with experimental uncertainties that are commonly associated with this analytical method.

Mettler FP 81HT/FP90 Apparatus (Indicated by FP90 in Table 3)

For a number of compounds, melting points were determined in open capillary tubes either on a Mettler FP62 or a Mettler FP81HT/FP90 apparatus. Melting points were measured with a temperature gradient of 1, 3, 5 or 10° C./minute. Maximum temperature was 300° C. The melting point was read from a digital display.

DSC823e (Indicated by DSC in Table 3)

For a number of compounds, melting points were determined with a DSC823e (Mettler-Toledo). Melting points were measured with a temperature gradient of 30 C/minute. Maximum temperature was 400° C.

TABLE 3

Analytical data

| Co. Nr. | $R_t$ | $[M + H]^+$ | Method | Melting Point |
|---|---|---|---|---|
| 1 | 0.56 | 305 | 1 | 208.7° C. (FP90) |
| 2 | 1.05 | 334 | 1 | 203.1° C. (FP90) |
| 3 | 2.60 | 371 | 1 | 221.9° C. (FP90) |
| 4 | 0.60 | 305 | 3 | 191.9° C. (FP 90) |
| 5 | 4.07 | 371 | 2 | n.d |
| 6 | 1.54 | 381 | 3 | 222.7° C. (FP 90) |
| 7 | 0.87 | 323 | 3 | n.d |
| 8 | 1.72 | 399 | 3 | 105.7° C. (FP 62) |
| 9 | 1.43 | 396 | 3 | 117.8° C. (FP 62) |
| 10 | 1.43 | 383 | 3 | 211.2° C. (FP 62) |
| 11 | 1.07 | 341 | 3 | 126.2° C. (FP 90) |
| 12 | 1.89 | 374 | 3 | 112.2° C. (FP 90) |
| 13 | 2.48 | 372 | 4 | 140.0° C. (FP 90) |
| 14 | 1.49 | 381 | 3 | 114.5° C. (FP 90) |
| 15 | 1.57 | 415 | 3 | n.d. |
| 16 | 1.23 | 378 | 3 | n.d. |
| 17 | 2.61 | 395 | 4 | 102.2° C. (FP 90) |
| 18 | 1.33 | 390 | 3 | 229.5° C. (FP 90) |
| 19 | 1.68 | 433 | 3 | 139.4° C. (FP 90) |
| 20 | 2.39 | 417 | 5 | 92.2° C. (FP 90) |
| 21 | 1.38 | 424 | 3 | n.d. |
| 22 | 2.08 | 408 | 4 | n.d. |
| 23 | 1.72 | 410 | 3 | 99.0° C. (FP 90) |
| 24 | 0.95 | 451 | 6 | 120.05° C. (DSC) |
| 25 | 1.00 | 501 | 6 | X° C. (DSC) |
| 26 | 0.92 | 464 | 6 | X° C. (DSC) |
| 27 | 1.91 | 419 | 3 | n.d. |
| 28 | 2.42 | 419 | 7 | n.d. |
| 29 | 2.42 | 419 | 7 | n.d. |
| 30 | 2.21 | 469 | 3 | n.d. |
| 31 | 2.58 | 469 | 7 | n.d. |
| 32 | 2.58 | 469 | 7 | n.d. |
| 33 | 2.04 | 453 | 3 | >300° C. (FP 90) |
| 34 | 1.87 | 432 | 3 | >300° C. (FP 90) |
| 35 | 2.39 | 432 | 7 | n.d. |

TABLE 3-continued

Analytical data

| Co. Nr. | $R_t$ | $[M + H]^+$ | Method | Melting Point |
|---|---|---|---|---|
| 36 | 2.39 | 432 | 7 | n.d. |
| 37 | 0.89 | 472 | 6 | n.d. |
| 38 | 0.84 | 437 | 6 | n.d. |
| 39 | 1.03 | 505 | 6 | n.d. |
| 40 | 0.87 | 439 | 6 | n.d. |
| 41 | 0.92 | 451 | 6 | 145.06° C. (DSC) |
| 42 | 1.24 | 404 | 3 | 94.0° C. (FP 90) |
| 43 | 1.92 | 369 | 4 | 103.7° C. (FP 90) |
| 44 | 2.48 | 437 | 5 | 157.1° C. (FP 90) |
| 45 | 2.05 | 371 | 4 | 138.2° C. (FP 90) |
| 46 | 2.53 | 383 | 4 | 102.3° C. (FP 90) |
| 47 | 1.99 | 446 | 3 | 141.2° C. (FP 90) |
| 48 | 2.03 | 433 | 3 | 179.9° C. (FP 90) |
| 49 | 1.95 | 440 | 3 | 181.5° C. (FP 90) |
| 50 | 2.33 | 449 | 3 | 100.2° C. (FP 90) |
| 51 | 1.87 | 454 | 3 | 93.8° C. (FP 90) |
| 52 | 0.83 | 430 | 6 | n.d. |
| 53 | 0.85 | 417 | 6 | 207.96° C. (DSC) |
| 54 | 0.88 | 461 | 6 | n.d. |
| 55 | 0.9 | 474 | 6 | n.d. |
| 56 | 0.85 | 408 | 6 | n.d. |
| 57 | 0.91 | 430 | 6 | n.d. |
| 58 | 0.92 | 417 | 6 | n.d. |
| 59 | 1 | 442 | 6 | n.d. |
| 60 | 0.99 | 455 | 6 | n.d. |
| 61 | 1.07 | 458 | 6 | n.d. |
| 62 | 0.97 | 449 | 6 | n.d. |
| 63 | 0.95 | 463 | 6 | n.d. |
| 64 | 0.86 | 421 | 6 | n.d. |
| 65 | 0.83 | 429 | 6 | n.d. |
| 66 | 0.87 | 408 | 6 | n.d. |
| 67 | 0.85 | 415 | 6 | n.d. |
| 68 | 0.94 | 424 | 6 | n.d. |
| 69 | 1.03 | 458 | 6 | n.d. |
| 70 | 1.00 | 472 | 6 | n.d. |
| 71 | 1.08 | 467 | 6 | n.d. |
| 72 | 1.05 | 451 | 6 | n.d. |
| 73 | 1.04 | 464 | 6 | n.d. |
| 74 | 0.94 | 449 | 6 | n.d. |
| 75 | 0.85 | 440 | 6 | 247.82° C. (DSC) |
| 76 | 0.86 | 446 | 6 | n.d. |
| 77 | 0.87 | 433 | 6 | n.d. |
| 78 | 0.83 | 454 | 6 | n.d. |
| 79 | 0.79 | 421 | 6 | n.d. |
| 80 | 0.77 | 415 | 6 | n.d. | n.d. means not determined $R_t$ means retention time (in minutes), $[M + H]^+$ means the protonated mass of the compound, method refers to the method used for (LC)MS.

SFC/MS-Methods:

General Procedure A for SFC-MS:

The SFC measurement was performed using Analytical system from Berger instrument comprises a FCM-1200 dual pump fluid control module for delivering carbon dioxide ($CO_2$) and modifier, a CTC Analytics automatic liquid sampler, a TCM-20000 thermal control module for column heating from room temperature to 80° C. An Agilent 1100 UV photodiode array detector equipped with a high-pressure flow cell standing up to 400 bars was used. Flow from the column was split to a MS spectrometer. The MS detector was configured with an atmospheric pressure ionization source. The following ionization parameters for the Waters ZQ mass spectrophotometer are: corona: 9 μa, source temp: 140° C., cone: 30 V, probe temp 450° C., extractor 3 V, desolvatation gas 400 L/hr, cone gas 70 L/hr. Nitrogen was used as the nebulizer gas. Data acquisition was performed with a Waters-Micromass MassLynx-Openlynx data system.

Method 1

In addition to the general procedure A: The chiral separation in SFC was carried out on a CHIRALCEL OJ DAICEL column (5 μm, 4.6×250 mm) at 35° C. with a flow rate of 3.0 ml/min. The mobile phase is CO2, 30% iPrOH (containing 0.3% iPrNH2) in isocratic mode.

Method 2

In addition to the general procedure A: The chiral separation in SFC was carried out on a CHIRALPAK IC DAICEL column (5 μm, 4.6×250 mm) with a flow rate of 3.0 ml/min. The mobile phase is CO2, 50% iPrOH (containing 0.3% iPrNH2) in isocratic mode.

General Procedure B for SFC-MS:

Analytical SFC system from Berger Instruments (Newark, Del., USA) comprising a dual pump control module (FCM-1200) for delivery of carbon dioxide ($CO_2$) and modifier, a thermal control module for column heating (TCM2100) with temperature control in the range 1-150° C. and column selection valves (Valco, VICI, Houston, Tex., USA) for six different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

Method 3

In addition to the general procedure B: The chiral separation in SFC was carried out on a CHIRALCEL OD-H column (4.6×250 mm) at 30° C. with a flow rate of 3.0 ml/min. The mobile phase is 10-40% MeOH (containing 0.2% iPrNH2)/CO2 at 1.6%/min. rate, then from 40-50% MeOH/CO2 at 5% rate and hold 3.60 min. at 50%.

Method 4

Same gradient as method 3 but using CHIRALPAK AS-H column (4.6×250 mm) instead.

Method 5

In addition to the general procedure B: The chiral separation in SFC was carried out on a CHIRALCEL OJ-H column (4.6×250 mm) at 30° C. with a flow rate of 3.0 ml/min. The mobile phase is 15% EtOH (containing 0.2% iPrNH2)/CO2 and hold 15 min.

Method 6

In addition to the general procedure B: The chiral separation in SFC was carried out on a CHIRALPAK AS-H column (4.6×250 mm) at 30° C. with a flow rate of 3.0 ml/min. The mobile phase is 5% MeOH (containing 0.2% iPrNH2)/CO2 hold 16.16 min, then from 5-40% MeOH/CO2 at 10% rate and hold 3.34 min. at 50%.

TABLE 4

Analytical SFC data

| Co. Nr. | $R_t$ | $[M + H]^+$ | UV Area % | Method | Isomer Elution Order |
|---|---|---|---|---|---|
| 28 | 1.84 | 419 | 100 | 1 | A |
| 29 | 4.02 | 419 | 100 | 1 | B |
| 31 | 2.45 | 469 | 100 | 1 | A |
| 32 | 3.79 | 469 | 100 | 1 | B |
| 35 | 3.08 | 432 | 100 | 2 | A |
| 36 | 3.70 | 432 | 100 | 2 | B |
| 37 | 6.62 | 472 | 97.6 | 6 | — |
| 38 | 2.51 | 437 | 100 | 5 | A |
| 42 | 6.60 | 404 | 98.5 | 3 | — |

TABLE 4-continued

Analytical SFC data

| Co. Nr. | $R_t$ | $[M + H]^+$ | UV Area % | Method | Isomer Elution Order |
|---|---|---|---|---|---|
| 43 | 7.14 | 369 | 100 | 3 | — |
| 46 | 4.06 | 383 | 97.4 | 4 | — |

Isomer Elution Order: A means first eluting isomer; B means second eluting isomer.
$R_t$ means retention time (in minutes), $[M + H]^+$ means the protonated mass of the compound, method refers to the method used for SFC/MS analysis of enantiomerically pure compounds.

Optical Rotations:

Optical rotations were measured on a Perkin-Elmer 341 polarimeter with a sodium lamp and reported as follows: $[\alpha]°$ ($\lambda$, c g/100 ml, solvent, T° C.).

$[\alpha]_\lambda^T = (100\alpha)/(l \times c)$: where l is the path length in dm and c is the concentration in g/100 ml for a sample at a temperature T (° C.) and a wavelength $\lambda$ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

TABLE 5

Analytical data—Optical rotation values for enantiomerically pure compounds

| Co. Nr. | $\alpha_D$ (°) | Wavelength (nm) | Concentration w/v % | Solvent | Temp. (° C.) |
|---|---|---|---|---|---|
| 4 | −81.5 | 589 | 0.5 | DMF | 20 |
| 8 | +86.8 | 589 | 0.5 | DMF | 20 |
| 10 | +66.4 | 589 | 0.62 | DMF | 20 |
| 11 | +21.6 | 589 | 0.62 | DMF | 20 |
| 12 | +95.8 | 589 | 0.62 | MeOH | 20 |
| 13 | −2.8 | 589 | 0.58 | DMF | 20 |
| 14 | −47.0 | 589 | 0.65 | DMF | 20 |
| 17 | +104.8 | 589 | 0.55 | DMF | 20 |
| 18 | +120.0 | 589 | 0.55 | DMF | 20 |
| 19 | +88.5 | 589 | 0.59 | DMF | 20 |
| 21 | −28.6 | 589 | 0.50 | DMF | 20 |
| 23 | +90.8 | 589 | 0.52 | DMF | 20 |
| 24 | +84.1 | 589 | 0.44 | DMF | 20 |
| 25 | +81.0 | 589 | 0.36 | DMF | 20 |
| 26 | +97.9 | 589 | 0.26 | DMF | 20 |
| 28 | +150.8 | 589 | 0.52 | DMF | 20 |
| 29 | −156.8 | 589 | 0.50 | DMF | 20 |
| 31 | +131.6 | 589 | 0.50 | DMF | 20 |
| 32 | −125.3 | 589 | 0.52 | DMF | 20 |
| 35 | +171.0 | 589 | 0.50 | DMF | 20 |
| 36 | −158.8 | 589 | 0.53 | DMF | 20 |
| 37 | +80.4 | 589 | 0.21 | DMF | 20 |
| 38 | +76.4 | 589 | 0.39 | DMF | 20 |
| 39 | +48.3 | 589 | 0.26 | DMF | 20 |
| 40 | +93.6 | 589 | 0.38 | DMF | 20 |
| 44 | +60.8 | 589 | 0.51 | DMF | 20 |
| 45 | +81.9 | 589 | 0.53 | DMF | 20 |
| 47 | +105.2 | 589 | 0.50 | DMF | 20 |
| 48 | +88.9 | 589 | 0.58 | DMF | 20 |
| 49 | +121.7 | 589 | 0.46 | DMF | 20 |
| 50 | +103.8 | 589 | 0.54 | DMF | 20 |

NMR

For a number of compounds, $^1$H NMR spectra were recorded on a Bruker DPX-360, on a Bruker DPX-400 or on a Bruker AV-500 spectrometer with standard pulse sequences, operating at 360 MHz, 400 MHz and 600 MHz respectively, using CHLOROFORM-d (deuterated chloroform, $CDCl_3$) or DMSO-$d_6$ (deuterated DMSO, dimethyl-d6 sulfoxide) as solvents. Chemical shifts ($\delta$) are reported in parts per million (ppm) relative to tetramethylsilane (TMS), which was used as internal standard.

TABLE 6

| Co. Nr. | NMR result |
|---|---|
| 42 | $^1$H NMR (400 MHz, $CDCl_3$) δ ppm 1.98 (s, 3 H), 4.41 (d, J = 13.6 Hz, 1 H), 5.04 (dd, J = 13.5, 1.5 Hz, 1 H), 7.03 (d, J = 2.8 Hz, 1 H), 7.10 (dd, J = 12.0, 9.0 Hz, 1 H), 7.25 (t, J = 59.9 Hz, 1 H), 7.18 (s, 1 H), 7.24-7.27 (m, 1 H), 7.29 (s, 1 H), 7.36 (dd, J = 7.4, 2.5 Hz, 1 H), 7.88 (d, J = 2.5 Hz, 1 H), 7.96 (ddd, J = 8.9, 4.0, 2.5 Hz, 1 H), 8.72 (s, 1 H), 12.31 (br. s., 1 H), 13.25 (br. s., 1 H). |
| 49 | $^1$H NMR (500 MHz, $CDCl_3$) δ ppm 1.63 (s, 3 H), 4.38 (d, J = 13.0 Hz, 1 H), 4.48 (d, J = 12.7 Hz, 1 H), 5.33 (br. s., 2 H), 6.65 (t, J = 55.8 Hz, 1 H), 7.11 (dd, J = 11.7, 8.8 Hz, 1 H), 7.24 (s, 1 H), 7.85 (dd, J = 7.1, 2.6 Hz, 1 H), 7.98-8.03 (m, 1 H), 8.20 (dd, J = 8.1, 1.7 Hz, 1 H), 8.41 (d, J = 8.1 Hz, 1 H), 8.88 (s, 1 H), 9.86 (br. s., 1 H). |
| 51 | $^1$H NMR (500 MHz, $CDCl_3$) δ ppm 1.62 (s, 3 H), 4.37 (d, J = 13.0 Hz, 1 H), 4.46 (d, J = 13.0 Hz, 1 H), 5.29 (br. s., 2 H), 6.65 (t, J = 55.8 Hz, 1 H), 7.03 (d, J = 2.6 Hz, 1 H), 7.07 (dd, J = 11.6, 9.0 Hz, 1 H), 7.20 (t, J = 60.4 Hz, 1 H), 7.23 (br. s, 1 H), 7.76 (dd, J = 6.9, 2.9 Hz, 1 H), 7.87 (d, J = 2.6 Hz, 1 H), 7.92 (ddd, J = 8.8, 4.2, 2.9 Hz, 1 H), 8.66 (s, 1 H). |
| 52 | $^1$H NMR (360 MHz, $CDCl_3$) δ ppm 1.62 (s, 3 H) 4.07 (s, 3 H) 4.25-4.43 (m, 2 H) 5.23 (br. s., 2 H) 6.90 (s, 1 H) 7.08 (dd, J = 11.9, 9.0 Hz, 1 H) 7.76 (dd, J = 7.0, 2.6 Hz, 1 H) 8.00 (ddd, J = 8.7, 4.3, 2.7 Hz, 1 H) 8.15 (d, J = 1.1 Hz, 1 H) 9.00 (d, J = 1.1 Hz, 1 H) 9.51 (s, 1 H). |
| 53 | $^1$H NMR (360 MHz, $CDCl_3$) δ ppm 1.63 (s, 3 H) 4.26-4.43 (m, 2 H) 6.90 (s, 1 H) 7.08 (dd, J = 11.9, 9.0 Hz, 1 H) 7.59 (td, J = 8.3, 2.7 Hz, 1 H) 7.79 (dd, J = 7.0, 2.6 Hz, 1 H) 8.00 (dt, J = 8.8, 3.5 Hz, 1 H) 8.32 (dd, J = 8.6, 4.6 Hz, 1 H) 8.45 (d, J = 2.9 Hz, 1 H) 9.81 (s, 1 H). |
| 56 | $^1$H NMR (360 MHz, $CDCl_3$) δ ppm 1.63 (s, 3 H) 3.33 (br. s., 2 H) 4.46 (q, J = 13.1 Hz, 2 H) 7.09 (dd, J = 11.9, 8.6 Hz, 1 H) 7.52 (s, 1 H) 7.59 (td, J = 8.3, 2.7 Hz, 1 H) 7.82-7.96 (m, 2 H) 8.30 (dd, J = 8.6, 4.6 Hz, 1 H) 8.42 (d, J = 2.6 Hz, 1 H) 9.82 (s, 1 H). |
| 57 | $^1$H NMR (360 MHz, $CDCl_3$) δ ppm 1.65 (s, 3 H) 4.07 (s, 3 H) 4.21-4.44 (m, 2 H) 7.01 (s, 1 H) 7.10 (dd, J = 11.7, 9.1 Hz, 1 H) 7.75 (dd, J = 7.0, 2.6 Hz, 1 H) 7.91-8.06 (m, 1 H) 8.16 (d, J = 0.7 Hz, 1 H) 9.01 (s, 1 H) 9.51 (s, 1 H). |
| 58 | $^1$H NMR (360 MHz, $CDCl_3$) δ ppm 1.65 (s, 3 H) 4.32 (q, J = 13.2 Hz, 2 H) 7.01 (s, 1 H) 7.10 (dd, J = 11.7, 8.8 Hz, 1 H) 7.59 (td, J = 8.4, 2.9 Hz, 1 H) 7.78 (dd, J = 7.1, 2.7 Hz, 1 H) 8.01 (ddd, J = 8.9, 4.1, 2.7 Hz, 1 H) 8.32 (dd, J = 8.6, 4.6 Hz, 1 H) 8.45 (d, J = 2.6 Hz, 1 H) 9.81 (s, 1 H). |
| 64 | $^1$H NMR (360 MHz, DMSO-$d_6$) δ ppm 1.52 (s, 3 H) 4.02 (s, 3 H) 4.46 (q, J = 13.2 Hz, 2 H) 6.70 (br. s., 2 H) 7.20 (dd, J = 12.1, 8.8 Hz, 1 H) 7.73 (ddd, J = 8.3, 3.8, 3.6 Hz, 1 H) 7.94 (s, 1 H) 8.10 (dd, J = 7.7, 2.6 Hz, 1 H) 8.41 (d, J = 1.1 Hz, 1 H) 8.87 (d, J = 1.1 Hz, 1 H) 10.50 (s, 1 H). |
| 65 | $^1$H NMR (360 MHz, DMSO-$d_6$) δ ppm 1.51 (s, 3 H) 4.45 (q, J = 13.2 Hz, 2 H) 6.69 (br. s., 2 H) 7.00 (d, J = 2.6 Hz, 1 H) 7.19 (dd, J = 12.3, 9.0 Hz, 1 H) 7.61-7.72 (m, 1 H) 7.91 (t, J = 58.7 Hz, 1 H) 7.94 (s, 1 H) 8.01 (dd, J = 7.5, 2.7 Hz, 1 H) 8.40 (d, J = 2.9 Hz, 1 H) 10.40 (s, 1 H). |
| 66 | $^1$H NMR (360 MHz, DMSO-$d_6$) δ ppm 1.52 (s, 3 H) 4.36-4.55 (m, 2 H) 6.72 (br. s., 2 H) 7.21 (dd, J = 12.1, 8.8 Hz, 1 H) 7.72-7.80 (m, 1 H) 7.93-8.02 (m, 1 H) 7.95 (s, 1 H) 8.10 (dd, J = 7.3, 2.6 Hz, 1 H) 8.22 (dd, J = 8.8, 4.8 Hz, 1 H) 8.73 (d, J = 2.6 Hz, 1 H) 10.61 (s, 1 H). |
| 67 | $^1$H NMR (360 MHz, DMSO-$d_6$) δ ppm 1.52 (s, 3 H) 4.46 (q, J = 13.2 Hz, 2 H) 6.71 (br. s., 2 H) 7.23 (dd, J = 12.1, 8.8 Hz, 1 H) 7.71-7.83 (m, 1 H) 7.95 (s, 1 H) 8.12 (dd, J = 7.7, 2.6 Hz, 1 H) 8.27 (d, J = 8.1 Hz, 1 H) 8.58 (dd, J = 8.1, 1.8 Hz, 1 H) 9.20 (d, J = 1.1 Hz, 1 H) 10.84 (s, 1 H). |

Pharmacological Examples

The compounds provided in the present invention are inhibitors of the β-site APP-cleaving enzyme 1 (BACE1)

Inhibition of BACE1, an aspartic protease, is believed to be relevant for treatment of Alzheimer's Disease (AD). The production and accumulation of β-amyloid peptides (Aβ) from the β-amyloid precursor protein (APP) is believed to play a key role in the onset and progression of AD. Aβ is produced from the amyloid precursor protein (APP) by sequential cleavage at the N- and C-termini of the Aβ domain by β-secretase and γ-secretase, respectively.

Compounds of Formula (I) are expected to have their effect substantially at BACE1 by virtue of their ability to inhibit the enzymatic activity. The behaviour of such inhibitors tested using a biochemical Fluorescence Resonance Energy Transfer (FRET) based assay and a cellular αlisa assay in SKNBE2 cells described below and which are suitable for the identification of such compounds, and more particularly the compounds according to Formula (I), are shown in Table 7.

Biochemical FRET Based Assay

This assay is a Fluorescence Resonance Energy Transfer Assay (FRET) based assay. The substrate for this assay is an APP derived 13 amino acids peptide that contains the 'Swedish' Lys-Met/Asn-Leu mutation of the amyloid precursor protein (APP) β-secretase cleavage site. This substrate also contains two fluorophores: (7-methoxycoumarin-4-yl) acetic acid (Mca) is a fluorescent donor with excitation wavelength at 320 nm and emission at 405 nm and 2,4-Dinitrophenyl (Dnp) is a proprietary quencher acceptor. The distance between those two groups has been selected so that upon light excitation, the donor fluorescence energy is significantly quenched by the acceptor, through resonance energy transfer. Upon cleavage by BACE1, the fluorophore Mca is separated from the quenching group Dnp, restoring the full fluorescence yield of the donor. The increase in fluorescence is linearly related to the rate of proteolysis (Koike H et al. *J. Biochem.* 1999, 126, 235-242).

Briefly in a 384-well format recombinant BACE1 protein in a final concentration of 1 μg/ml is incubated for 120 minutes at room temperature with 10 μm substrate in incubation buffer (40 mM Citrate buffer pH 5.0, 0.04% PEG, 4% DMSO) in the absence or presence of compound. Next the amount of proteolysis is directly measured by fluorescence measurement at T=0 and T=120 (excitation at 320 nm and emission at 405 nm). Results are expressed in RFU, as difference between T120 and T0 A best-fit curve is fitted by a minimum sum of squares method to the plot of % Controlmin versus compound concentration. From this an $IC_{50}$ value (inhibitory concentration causing 50% inhibition of activity) can be obtained.

LC=Median of the low control values
 =Low control: Reaction without enzyme
HC=Median of the High control values
 =High Control: Reaction with enzyme % Effect=100−[(sample−*LC*)/(*HC*−*LC*)*100]

% Control=(sample/*HC*)*100%

% Controlmin=(sample−*LC*)/(*HC*−*LC*)*100

The following exemplified compounds were tested essentially as described above and exhibited the following the activity:

TABLE 7

| Co. Nr. | Biochemical FRET based assay $pIC_{50}$ |
|---|---|
| 1 | 5.01 |
| 2 | >4.52 |
| 3 | 4.57 |
| 4 | >4.52 |
| 5 | 4.85 |
| 6 | 6.48 |
| 7 | 4.70 |
| 8 | 7.19 |
| 9 | 6.83 |
| 10 | 6.67 |
| 11 | 4.78 |
| 12 | 4.73 |
| 13 | 6.78 |
| 14 | 6.76 |
| 15 | 6.95 |
| 16 | 6.14 |
| 17 | 6.97 |
| 18 | 7.27 |
| 19 | 7.31 |
| 20 | 7.12 |
| 21 | 7.31 |
| 22 | 7.02 |
| 23 | 6.34 |
| 24 | 6.88 |
| 25 | 7.33 |
| 26 | 6.63 |
| 27 | 6.23 |
| 28 | 6.53 |
| 29 | <4.52 |
| 30 | 6.72 |
| 31 | 7.26 |
| 32 | 4.68 |
| 33 | 6.65 |
| 34 | 6.43 |
| 35 | 6.82 |
| 36 | 4.62 |
| 37 | 7.33 |
| 38 | 7.00 |
| 39 | 6.57 |
| 40 | 6.64 |
| 41 | 6.75 |
| 42 | 6.94 |
| 43 | 6.73 |
| 44 | 6.42 |
| 45 | 6.37 |
| 46 | 6.42 |
| 47 | 6.63 |
| 48 | 6.88 |
| 49 | 7.01 |
| 50 | 7.23 |
| 51 | 6.79 |
| 52 | 7.01 |
| 53 | 7.21 |
| 54 | 7.12 |
| 55 | 6.95 |
| 56 | 7.08 |
| 57 | 7.18 |
| 58 | 7.12 |
| 59 | n.d. |
| 60 | n.d. |
| 61 | n.d. |
| 62 | n.d. |
| 63 | n.d. |
| 64 | 7.33 |
| 65 | 7.35 |
| 66 | 7.20 |
| 67 | 7.41 |
| 68 | 7.29 |
| 69 | n.d. |
| 70 | n.d. |
| 71 | n.d. |
| 72 | n.d. |
| 73 | n.d. |
| 74 | n.d. |
| 75 | n.d. |
| 76 | n.d. |
| 77 | n.d. |
| 78 | n.d. |

TABLE 7-continued

| Co. Nr. | Biochemical FRET based assay pIC$_{50}$ |
|---|---|
| 79 | n.d. |
| 80 | n.d. | n.d. means not determined

Cellular αlisa Assay in SKNBE2 Cells

In two αlisa assays the levels of Aβtotal and Aβ42 produced and secreted into the medium of human neuroblastoma SKNBE2 cells are quantified. The assay is based on the human neuroblastoma SKNBE2 expressing the wild type Amyloid Precursor Protein (hAPP695). The compounds are diluted and added to these cells, incubated for 18 hours and then measurements of Aβ42 and Aβtotal are taken. Aβtotal and Aβ42 are measured by sandwich αlisa. αlisa is a sandwich assay using biotinylated antibody AbN/25 attached to streptavidin coated beads and antibody Ab4G8 or cAb42/26 conjugated acceptor beads for the detection of Aβtotal and Aβ42 respectively. In the presence of Aβtotal or Aβ42, the beads come into close proximity. The excitation of the Donor beads provokes the release of singlet oxygen molecules that triggers a cascade of energy transfer in the Acceptor beads, resulting in light emission. Light emission is measured after 1 hour incubation (excitation at 650 nm and emission at 615 nm).

A best-fit curve is fitted by a minimum sum of squares method to the plot of % Controlmin versus compound concentration. From this an IC$_{50}$ value (inhibitory concentration causing 50% inhibition of activity) can be obtained.
LC=Median of the low control values
=Low control: cells preincubated without compound, without biotinylated Ab in the αlisa
HC=Median of the High control values
=High Control: cells preincubated without compound % Effect=100−[(sample−LC)/(HC−LC)*100]

% Control=(sample/HC)*100%

% Controlmin=(sample−LC)/(HC−LC)*100

The following exemplified compounds were tested essentially as described above and exhibited the following the activity:

TABLE 8

| Co. Nr. | Cellular αlisa assay in SKNBE2 cells Aβ42 pIC$_{50}$ | Cellular αlisa assay in SKNBE2 cells Aβtotal pIC$_{50}$ |
|---|---|---|
| 1 | 6.72 | 6.76 |
| 2 | 5.67 | 5.63 |
| 3 | 5.10 | 5.15 |
| 4 | 5.11 | 5.11 |
| 5 | 5.23 | 5.30 |
| 6 | 7.15 | 7.16 |
| 7 | 5.56 | 5.62 |
| 8 | 7.91 | 7.96 |
| 9 | 7.45 | 7.50 |
| 10 | 7.23 | 7.30 |
| 11 | 5.63 | 5.71 |
| 12 | 5.63 | 5.66 |
| 13 | 7.68 | 7.67 |
| 14 | 7.60 | 7.60 |
| 15 | 7.65 | 7.67 |
| 16 | 7.09 | 7.08 |
| 17 | 7.76 | 7.78 |
| 18 | 8.20 | 8.25 |
| 19 | 7.96 | 8.01 |
| 20 | 7.76 | 7.75 |
| 21 | 8.03 | 8.02 |
| 22 | 8.02 | 8.07 |
| 23 | 7.60 | 7.43 |
| 24 | 7.41 | 7.47 |
| 25 | 7.66 | 7.77 |
| 26 | 7.07 | 7.14 |
| 27 | 6.05 | 6.11 |
| 28 | 6.17 | 6.19 |
| 29 | <5 | <5 |
| 30 | 6.99 | 7.03 |
| 31 | 6.54 | 6.57 |
| 32 | <5 | <5 |
| 33 | 6.45 | 6.56 |
| 34 | 6.12 | 6.22 |
| 35 | 6.35 | 6.39 |
| 36 | <5 | <5 |
| 37 | 7.80 | 7.78 |
| 38 | 7.37 | 7.38 |
| 39 | 6.80 | 6.80 |
| 40 | 7.06 | 7.04 |
| 41 | 6.92 | 6.93 |
| 42 | 7.72 | 7.70 |
| 43 | 7.42 | 7.37 |
| 44 | 7.02 | 7.03 |
| 45 | 7.18 | 7.17 |
| 46 | 7.05 | 7.08 |
| 47 | 7.39 | 7.36 |
| 48 | 7.43 | 7.44 |
| 49 | 8.07 | 8.03 |
| 50 | 8.13 | 8.09 |
| 51 | n.d. | n.d. |
| 52 | 7.39 | 7.42 |
| 53 | 7.44 | 7.45 |
| 54 | 7.49 | 7.45 |
| 55 | 7.50 | 7.49 |
| 56 | 7.68 | 7.66 |
| 57 | 7.87 | 7.83 |
| 58 | 7.70 | 7.70 |
| 59 | n.d. | n.d. |
| 60 | n.d. | n.d. |
| 61 | n.d. | n.d. |
| 62 | n.d. | n.d. |
| 63 | n.d. | n.d. |
| 64 | n.d. | n.d. |
| 65 | n.d. | n.d. |
| 66 | n.d. | n.d. |
| 67 | n.d. | n.d. |
| 68 | n.d. | n.d. |
| 69 | n.d. | n.d. |
| 70 | n.d. | n.d. |
| 71 | n.d. | n.d. |
| 72 | n.d. | n.d. |
| 73 | n.d. | n.d. |
| 74 | n.d. | n.d. |
| 75 | n.d. | n.d. |
| 76 | n.d. | n.d. |
| 77 | n.d. | n.d. |
| 78 | n.d. | n.d. |
| 79 | n.d. | n.d. |
| 80 | n.d. | n.d. |

Demonstration of In Vivo Efficacy

Aβ peptide lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ peptide lowering agents can be administered in any standard form using any standard method. For example, but not limited to, Aβ peptide lowering agents can be in the form of liquid, tablets or capsules that are taken orally or by injection. Aβ peptide lowering agents can be administered at any dose that is sufficient to significantly reduce levels of Aβ peptides in the blood, blood plasma, serum, cerebrospinal fluid (CSF), or brain.

To determine whether acute administration of an Aβ42 peptide lowering agent would reduce Aβ peptide levels in vivo, non-transgenic rodents, e.g. mice or rats were used. Animals treated with the Aβ peptide lowering agent were examined and compared to those untreated or treated with vehicle and brain levels of soluble Aβ42 and total Aβ were quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβpeptide lowering compounds were formulated in 20% hydroxypropyl β cyclodextrin. The Aβ peptide lowering agents were administered as a single oral dose (p.o.) or a single subcutaneous dose (s.c.) to overnight fasted animals. After a certain time, usually 2 or 4 h (as indicated in Table 19), the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβtotal and Aβ42.

To quantify the amount of Aβtotal and Aβ42 in the soluble fraction of the brain homogenates, Enzyme-Linked-Immunosorbent-Assays were used. Briefly, the standards (a dilution of synthetic Aβ1-40 and Aβ1-42, Bachem) were prepared in 1.5 ml Eppendorf tube in Ultraculture, with final concentrations ranging from 10000 to 0.3 pg/ml. The samples and standards were co-incubated with HRPO-labelled N-terminal antibody for Aβ42 detection and with the biotinylated mid-domain antibody 4G8 for Aβtotal detection. 50 µl of conjugate/sample or conjugate/standards mixtures were then added to the antibody-coated plate (the capture antibodies selectively recognize the C-terminal end of Aβ42, antibody JRF/cAβ42/26, for Aβ42 detection and the N-terminus of Aβ, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ42 quantification was finished by addition of Quanta Blu fluorogenic peroxidase substrate according to the manufacturer's instructions (Pierce Corp., Rockford, Il). A reading was performed after 10 to 15 min (excitation 320 nm/emission 420 nm).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Il). A reading was performed after 10 to 15 min (excitation 320 nm/emission 420 nm).

In this model at least 20% Aβ42 lowering compared to untreated animals would be advantageous.

The following exemplified compounds were tested essentially as described above and exhibited the following the activity:

TABLE 9

| Co. No. | Aβ42 (% Ctrl)_Mean | Aβtotal (% Ctrl)_Mean | Dose | Route of administration | Time after administration |
|---|---|---|---|---|---|
| 10 | 45 | 53 | 30 mpk | s.c. | 2 h |
| 9 | 57 | 49 | 30 mpk | s.c. | 2 h |
| 9 | 40 | 63 | 30 mpk | p.o. | 2 h |
| 18 | 38 | 52 | 30 mpk | p.o. | 2 h |
| 21 | 33 | 7 | 30 mpk | s.c. | 2 h |
| 24 | 50 | 67 | 30 mpk | s.c. | 4 h |

We claim:
1. A compound of Formula (I)

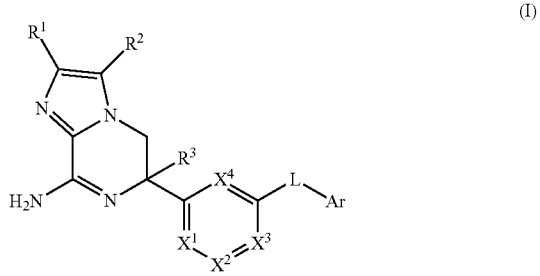

or a tautomer or a stereoisomeric form thereof, wherein
$R^1$ and $R^2$ are independently selected from the group consisting of hydrogen, halo, cyano, $C_{1-3}$alkyl, monohalo-$C_{1-3}$alkyl, polyhalo-$C_{1-3}$alkyl, and $C_{3-6}$cycloalkyl;
$R^3$ is selected from the group consisting of hydrogen, $C_{1-3}$alkyl, $C_{3-6}$cycloalkyl, monohalo-$C_{1-3}$alkyl, polyhalo-$C_{1-3}$alkyl, homoaryl and heteroaryl;
$X^1$, $X^2$, $X^3$, $X^4$ are independently $C(R^4)$ or N, provided that no more than two thereof represent N; each $R^4$ is selected from the group consisting of hydrogen, halo, $C_{1-3}$alkyl, monohalo-$C_{1-3}$alkyl, polyhalo-$C_{1-3}$alkyl, cyano, $C_{1-3}$alkyloxy, monohalo-$C_{1-3}$alkoxy, polyhalo-$C_{1-3}$alkyloxy;
L is a bond or —N($R^5$)CO—, wherein $R^5$ is hydrogen or $C_{1-3}$alkyl;
Ar is homoaryl or heteroaryl;
wherein homoaryl is phenyl or phenyl substituted with one, two or three substituents selected from the group consisting of halo, cyano, $C_{1-3}$alkyl, $C_{1-3}$alkyloxy, monohalo-$C_{1-3}$alkyl, polyhalo-$C_{1-3}$alkyl; heteroaryl is selected from the group consisting of pyridyl, pyrimidyl, pyrazyl, pyridazyl, furanyl, thienyl, pyrrolyl, pyrazolyl, imidazolyl, triazolyl, thiazolyl, isothiazolyl, thiadiazolyl, oxazolyl, and oxadiazolyl, each optionally substituted with one, two or three substituents selected from the group consisting of halo, cyano, $C_{1-3}$alkyl, $C_{1-3}$alkyloxy, monohalo-$C_{1-3}$alkyl, polyhalo-$C_{1-3}$alkyl; or an addition salt thereof.

2. The compound of claim 1 wherein,
$R^1$ and $R^2$ are independently selected from the group consisting of hydrogen, $CH_2F$, $CHF_2$, $CF_3$, chloro, bromo and cyano;
$R^3$ is $C_{1-3}$alkyl, $CH_2F$, $CHF_2$, or $CF_3$;
$X^1$ and $X^3$ are independently CH or CF; $X^2$ and $X^4$ are CH;
L is —N($R^5$)CO—, wherein $R^5$ is hydrogen;
Ar is homoaryl or heteroaryl;
wherein homoaryl is phenyl substituted with one or two substituents selected from the group consisting of halo, cyano, $C_{1-3}$alkyl, and $C_{1-3}$alkyloxy;
heteroaryl is selected from the group consisting of pyridyl, pyrimidyl, pyridazyl, pyrazolyl, oxazolyl and isothiazolyl, each optionally substituted with one or two substituents selected from the group consisting of halo, cyano, $C_{1-3}$alkyl, $C_{1-3}$alkyloxy, $CH_2F$, $CHF_2$, and $CF_3$; or an addition salt thereof.

3. The compound of claim 1 wherein,
$R^1$ is hydrogen, $CH_2F$, $CHF_2$, $CF_3$, chloro, bromo or cyano;
$R^2$ is hydrogen, chloro, cyano, $CH_2F$, $CHF_2$, or $CF_3$;
$R^3$ is methyl, $CH_2F$, $CHF_2$, or $CF_3$;
$X^1$ is CF; $X^2$, $X^3$, and $X^4$ are CH;
L is —N($R^5$)CO—, wherein $R^5$ is hydrogen;
Ar is heteroaryl;
wherein heteroaryl is selected from the group consisting of pyridyl, pyrazyl and pyrazolyl, each substituted with one or two substituents selected from the group consisting of chloro, fluoro, cyano, methyl, methoxy, ethoxy, $CH_2F$, $CHF_2$, and $CF_3$; or an addition salt thereof.

4. The compound of claim 1 wherein the carbon atom substituted with $R^3$ has the R-configuration.

5. A pharmaceutical composition comprising a therapeutically effective amount of a compound as defined in any one of claims 1 to 4 and a pharmaceutically acceptable carrier.

6. A process for preparing a pharmaceutical composition as defined in claim 5, characterized in that a pharmaceutically acceptable carrier is intimately mixed with a therapeutically effective amount of a compound as defined in any one of claims 1 to 4.

7. A method of inhibiting beta-site APP-cleaving enzyme 1 activity in a subject, comprising administering to said subject in need thereof, a therapeutically effective amount of a compound as defined in any one of claims 1 to 4 or a pharmaceutical composition as defined in claim 5.

* * * * *